US008318766B2

(12) United States Patent
Sui et al.

(10) Patent No.: US 8,318,766 B2
(45) Date of Patent: Nov. 27, 2012

(54) TETRACYCLIC HETEROATOM CONTAINING DERIVATIVES USEFUL AS SEX STEROID HORMONE RECEPTOR MODULATORS

(75) Inventors: Zhihua Sui, Raritan, NJ (US); Xuqing Zhang, Raritan, NJ (US); Xiaojie Li, Raritan, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 60 days.

(21) Appl. No.: 12/698,499

(22) Filed: Feb. 2, 2010

(65) Prior Publication Data

US 2010/0204239 A1  Aug. 12, 2010

Related U.S. Application Data

(62) Division of application No. 11/228,585, filed on Sep. 16, 2005, now Pat. No. 7,759,498.

(60) Provisional application No. 60/611,476, filed on Sep. 20, 2004.

(51) Int. Cl.
*A01N 43/42* (2006.01)
*A61K 31/44* (2006.01)
*C07D 487/00* (2006.01)

(52) U.S. Cl. .......................................... 514/285; 546/70

(58) Field of Classification Search .................... None
See application file for complete search history.

(56) References Cited

U.S. PATENT DOCUMENTS 5,688,808 A  11/1997  Jones et al.

FOREIGN PATENT DOCUMENTS

| JP | 11322756 | 11/1999 |
|---|---|---|
| WO | WO 9928300 A1 | 6/1999 |
| WO | WO 99/58524 A1 | 11/1999 |
| WO | WO 0006167 A1 | 2/2000 |
| WO | WO 03/053977 A1 | 7/2003 |
| WO | WO 2005/094833 A1 | 10/2005 |

OTHER PUBLICATIONS

Dorwald F. A. Side Reactions in Organic Synthesis, 2005, Wiley: VCH, Weinheim p. IX of Preface.*
Kidwai, et. al., Indian Journal of Chemistry, Section B: Organic Chemistry Including Medicinal Chemistry (1988), 27B(10), 962.*
Dorwald F.A., "Side Reactions in Organic Synthesis", (2005), Wiley: VCH, Weinheim, p. IX of Preface.
Kiang, et al., "The Structure and Properties of Certain Polycyclic Indolo- and Quinolino-derivatives. Part IV.* Derivatives of 1-Thiochroman-4-one and of 2-Thioisochroman-4-one", Journal of the Chemical Society, (1951), pp. 1909-1914.
McOmie, J., "Protective Groups in Organic Chemistry", (1973) Title Page and Table of Contents.
T.W. Greene & P.G.M. Wutz (eds.), Protective Groups in Organic Synthesis, $2^{nd}$ edition, Wiley Interscience, (1991), pp. 473.
Bundgaard, H., "Design of Prodrugs", (1985), Table of Contents.
PCT International Search Report for International application No. PCT/US2005/033330 dated Mar. 2, 2006.
Albright, J.D. et al.: Synthesis of 1,4,5,6-Tetrahydropyrazolo[3,4-*d* ]pyrido[3,2-*b* ]azepine; J. of Heterocyclic Chem. (2000) 37, pp. 41-46.
Allan, G.F. et al.: An Ultrhigh-Throughput Screening Assay for Estrogen Receptor Ligands; Anal. Biochem. (1999), 275(2), pp. 243-247.
Basaria, S. et al.: Anabolic-Androgenic Steroid Therapy in the Treatment of Chronic Diseases; The J. of Clin. Endocrinology & Metab (2001), 86(11), pp. 5108-5117.
Camps, F. et al.: Synthesis of 6-Methoxy-2,2-dimethyl-2*H*-1-benzothiopyran and 6,7-Dimethoxy-2,2-dimethyl-2*H*-1-benzothiopyran, Sulfur Analogues of Precocene I and Precocene II; J. of Heterocyclic Chem. (1983) 20, pp. 1115-1117.
Cook, C.E. et al.: Reversal of Activity Profile in Analogs of the Antiprogestin RU 486: Effect of a 16α-Subvstituent on Progestational (Agonist) Activity; Life Sciences (1993) 52, pp. 155-162.
Da Settimo, A. et al.: Synthesis of Novel 5*H*, 11*H* - Pyrido[2',3':2,3]thiopyrano[4,3-*b* ]-indoles by Fischer-Indole Cyclization; J. of Heterocyclic Chem. (2000) 37, pp. 379-382.
Newling, D.W.: Anti-androgens in the treatment of prostate cancer; Br. J. Urology (1996) 77(6), pp. 776-784.
Schenone, P. et al.: Reaction of 2-Dimethylaminomethylene-1,3-diones with Dinucleophiles. I. Synthesis of 1,5-Disubstituted 4-Acylpyrazoles; J. of Heterocyclic Chem. (1982) 19, pp. 1355-1361.
Shahidi, N. T.: A Review of the Chemistry, Biological Action, and Clinical Applications of Anabolic-Androgenic Steroids; Clin. Therapeutics (2001), 23(9), pp. 1355-1390.
Speckamp, W.N. et al.: Heterocyclic Steroids—XII[1] : Synthesis of N-Methyl- and N-Ethyl-6-Aza-8(14)-Dehydroestrone Methyl Ether; Tetrahedron (1968) 24, pp. 5881-5891.
Speckamp, W.N. et al.: Heterocyclic Steroids—XVII[1] : Total Synthesis of 6-Thia-Estrogens; Tetrahedron (1970) 26, pp. 2353-2363.
Wagner, B.L. et al.: 16α-substituted analogs of the antiprogestin RU486 induce a unique conformation in the human progesterone receptor resulting in mixed agonist activity; Proc. Natl. Acad. Sci., (1996) 93, pp. 8739-8744.
Batulin, Yu M., et al., "Pharmacology of some condensed indole systems", Farmakologiya I Toksikologiya, (1966), vol. 29, No. 5, pp. 590-594 (translation provided upon request).
Chunyan, Ou, "Summarization on Bioisosterism and Its Application in Design of New Drug", Journal of Zhanjiang Ocean University, (2004), vol. 24, No. 4, pp. 82-86 (translation provided).

* cited by examiner

*Primary Examiner* — Jeffrey Murray

(57) ABSTRACT

The present invention is directed to novel tetracyclic heteroatom containing derivatives, pharmaceutical compositions containing them, their use in the treatment of disorders mediated by one or more sex steroid hormone receptors and processes for their preparation.

2 Claims, No Drawings

TETRACYCLIC HETEROATOM CONTAINING DERIVATIVES USEFUL AS SEX STEROID HORMONE RECEPTOR MODULATORS

CROSS REFERENCE TO RELATED APPLICATIONS

This Application is a divisional of application Ser. No. 11/228,585 filed Sep. 16, 2005, now issued as U.S. Pat. No. 7,759,498 on Jul. 20, 2010, which in turn claims priority to U.S. Provisional Patent Application No. 60/611,476, filed Sep. 20, 2004, now abandoned, which are hereby incorporated by reference in their entirety.

FIELD OF THE INVENTION

The present invention is directed to novel tetracyclic heteroatom containing derivatives, pharmaceutical compositions containing them and their use in the treatment of disorders mediated by one or more sex steroid hormone receptors. The compounds of the present invention are selective estrogen, selective androgen and/or progestin receptor modulators.

BACKGROUND OF THE INVENTION

Estrogens are a group of female hormones essential for the reproductive process and for the development of the uterus, breasts, and other physical changes associated with puberty. Estrogens have an effect on various tissues throughout a woman's body, not only those involved in the reproductive process, such as the uterus, breasts, and external genitalia, but also tissues in the central nervous system, bones, the liver, skin, and the urinary tract. The ovaries produce most of the estrogens in a woman's body.

Menopause is defined as the permanent cessation of menses due to loss of ovarian follicular function and the near complete termination of estrogen production. The midlife transition of menopause is characterized by a decrease in estrogen that provokes both short-term and long-term symptoms with the vasomotor, urogenital, cardiovascular, skeletal and central nervous systems, such as hot flushes, urogenital atrophy, increased risk of cardiovascular disease, osteoporosis, cognitive and psychological impairment, including an increased risk of cognitive disorders and Alzheimer's disease (AD).

Seventy-five percent of all women experience some occurrence of vasomotor symptoms associated with the onset of menopause such as body sweating and hot flushes. These complaints may begin several years before menopause and in some women may continue for more than 10 years, either relatively constant, or as instant attacks without a definable, provoking cause.

Urogenital symptoms associated with the onset of menopause involving the vagina include a sensation of dryness, burning, itching, pain during intercourse, superficial bleeding and discharge, along with atrophy and stenosis. Symptoms involving the urinary tract include a burning sensation during urination, frequent urgency, recurrent urinary tract infections, and urinary incontinence. These symptoms have been reported to occur in up to 50% of all women near the time of menopause and are more frequent a few years after menopause. If left untreated, the problems can become permanent.

Heart attack and stroke are major causes of morbidity and mortality among senior women. Female morbidity from these diseases increases rapidly after menopause. Women who undergo premature menopause are at greater coronary risk than menstruating women of similar age. The presence of serum estrogen has a positive effect on serum lipids. The hormone promotes vasodilation of blood vessels, and enhances the formation of new blood vessels. Thus the decrease in serum estrogen levels in postmenopausal women results in an adverse cardiovascular effect. Additionally, it is theorized that differences in the ability of blood to coagulate may account for the observed difference in the occurrence of heart disease before and after menopause.

The skeleton is under a continuous process of bone degeneration and regeneration in a carefully regulated interaction among the bone cells. These cells are directly affected by estrogen. Estrogen deficiency results in a loss of bone structure, and decrease in bone strength. Rapid loss of bone mass during the year immediately following menopause leads to postmenopausal osteoporosis and increased risk of fracture.

Estrogen deficiency is also one of the causes for the degenerative changes in the central nervous system and may lead to Alzheimer's disease (AD) and a decline of cognition. Recent evidence suggests an association between estrogen, menopause and cognition. More particularly, it has been reported that estrogen replacement therapy and the use of estrogen in women may prevent the development of AD and improve cognitive function.

Hormone replacement therapy (HRT)—more specifically estrogen replacement therapy (ERT)—is commonly prescribed to address the medical problems associated with menopause, and also to help hinder osteoporosis and primary cardiovascular complications (such as coronary artery disease) in both a preventive and therapeutical manner. As such, HRT is considered a medical therapy for prolonging the average life span of postmenopausal women and providing a better quality of life.

ERT effectively relieves the climacteric symptoms and urogenital symptoms and has shown some benefits in the prevention and treatment of heart disease in postmenopausal women. Clinical reports have shown that ERT lowered heart attack rates and mortality rates in populations that received ERT versus similar populations not on ERT. ERT initiated soon after menopause may also help maintain bone mass for several years. Controlled investigations have shown that treatment with ERT has a positive effect even in older women up to 75 years of age.

However, there are numerous undesirable effects associated with ERT that reduce patient compliance. Venous thromboembolism, gallbladder disease, resumption of menses, mastodynia, and a possible increased risk of developing uterine and/or breast cancer are the risks associated with ERT. Up to 30% of women who are prescribed ERT do not fill the prescription, and the discontinuation rate for ERT is between 38% and 70%, with safety concerns, and adverse effects (bloating and break-through bleeding) the most important reasons for discontinuation.

A new class of pharmacological agents known as Selective Estrogen Receptor Modulators or SERMs have been designed and developed as alternatives for HRT. Raloxifene, a nonsteroidal benzothiophere SERM is marketed in the US and Europe for the prevention and treatment of osteoporosis under the trademark of Evista®. Raloxifene has been shown to reduce bone loss and prevent fracture without adversely stimulating endometrial and mammary tissue, though raloxifene is somewhat less efficacious than ERT for protecting against bone loss. Raloxifene is unique and differs significantly from ERT in that it does not stimulate the endometrium and has the potential for preventing breast cancer. Raloxifene has also demonstrated beneficial estrogen agonist effects on cardiovascular risk factors, more specifically through a rapid and sustained decrease in total and low-density lipoprotein cholesterol levels in patients treated with raloxifene. In addition, raloxifene has been shown to reduce plasma concentration of homocysteine, an independent risk factor for atherosclerosis and thromboembolic disease.

However, raloxifene has been reported to exacerbate symptoms associated with menopause such as hot flushes and vaginal dryness, and does not improve cognitive function in senior patients. Patients taking raloxifene have reported higher rates of hot flashes compared with either placebo or ERT users and more leg cramps than placebo users, although women who took ERT had a higher incidence of vaginal bleeding and breast discomfort than raloxifene or placebo users.

As yet, neither raloxifene nor any of the other currently available SERM compounds has been shown to have the ability to provide all the benefits of currently available ERT, such as controlling postmenopausal syndrome and preventing AD, without causing adverse side effects such as increasing risk of endometrial and breast cancer and bleeding. Thus there exists a need for compounds which are selective estrogen receptor modulators and which provide all of the benefits of ERT while also addressing the vasomotor, urogenital and cognitive disorders or conditions associated with the decrease in systemic estrogen associated with menopause.

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, agonists of the androgen receptor could be employed in the treatment of prostate cancer, benign prostatic hyperplasia, hirsutism in women, alopecia, anorexia nervosa, breast cancer and acne. Antagonists of the androgen receptor could be employed in male contraception, male performance enhancement, as well as in the treatment of cancer, AIDS, cachexia, and other disorders.

Progesterone plays a major role in reproductive health and functioning. Its effects on, for example, the uterus, breast, cervix and hypothalamic-pituitary unit are well established. The actions of progesterone as well as progesterone antagonists are mediated by the progesterone receptor (PR). In the target cell, progesterone produces a dramatic change in confirmation of the PR that is associated with transforming the PR from a non-DNA binding form to one that will bind to DNA. This transformation is accompanied by a loss of associated heat shock proteins and dimerization. The activated PR dimmer then binds to specific DNA sequences within the promotor region of progesterone responsive genes. The agonist-bound PR is believed to activate transcription by associating with coactivators, which act as bridging factors between the receptor and the general transcription machinery. This is followed by increases in the rate of transcription producing agonist effects at the cellular and tissue levels. These progesterone receptor ligands exhibit a spectrum of activity ranging from pure antagonists to mixed agonists/antagonists.

In 1982, the discovery of compounds that bind to the progesterone receptor, antagonize the effects of progesterone receptor and antagonize the effects of progesterone was announced. Although compounds such as estrogens and certain enzyme inhibitors can prevent the physiological effects of endogenous progesterone, the term "antiprogestin" is confined to those compounds that bind to the progestin receptor. A report from the Institute of Medicine (Donaldson, Molly S.; Dorflinger, L.; Brown, Sarah S.; Benet, Leslie Z., Editors, *Clinical Applications of Mifepristone (RU 486) and Other antiprogestins*, Committee on antiprogestins: Assessing the science, Institute of medicine, National Academy Press, 1993) summarized a number of medical conditions related to the effect of antiprogestins. In view of the pivotal role that progesterone plays in reproduction, it is not surprising that antiprogestins could play a part in fertility control, including contraception, menses induction and medical termination of pregnancy, but there are many other potential uses that have been supported by small clinical or preclinical studies, such as labor and delivery; treatment of uterine leiomyomas (fibroids), treatment of endometriosis; HRT; breast cancers; male contraception, etc.

The effects and uses of progesterone agonists have been well established. In addition, it has been recently shown that certain compounds structurally related to the known antiprogestins have agonist activity in certain biological systems (e.g., the classical progestin effects I the estrogen-primed immature rabbit uterus; cf. C. E. Cook et al., Life Sciences, 52, 155-162 (1993)). Such compounds are partial agonists in human cell-derived receptor systems, where they bind to a site distinct from both the progestin and antiprogestin sites (Wagner et al., Proc. Natl. Acad. Sci., 93, 8739-8744 (1996)). Thus the general class of antiprogestins can have subclasses, which may vary in their clinical profiles.

Compounds which mimic some of the effects of progesterone (agonists), antagonize these effects (antagonists, antiprogestins) or exhibit mixed effects (partial agonists or mixed agonist/antagonist), known as progesterone receptor modulators (PRMs) can be useful in treating a variety of disease states and conditions. PR agonists have been used in female contraceptives and in postmenopausal hormone therapy.

Recent studies in women and non-human primates show that PR antagonists may also have potential as contraceptive agents and for the treatment of various gynecological and obstetric diseases, including fibroids, endometriosis and, possibly, hormone-dependent cancers. Clinically available PR agonists and antagonists are steroidal compounds and often cause various side effects due to their functional interaction with other steroid receptors. Recently, numerous receptor-selective non-steroidal PR agonists and antagonists have emerged. Non-steroidal PR antagonists, being structurally distinct from the steroid class, may have greater potential for selectivity against other steroid receptors.

SUMMARY OF THE INVENTION

The present invention is directed to a compound of formula (I)

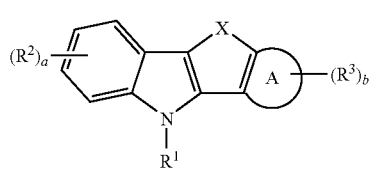

wherein

X is selected from the group consisting of —O—, —S and $NR^A$—; wherein $R^A$ is selected from the group consisting of hydrogen, $C_{1-6}$alkyl, —C(O)—$C_{1-6}$alkyl, —$C_{1-4}$alkyl-$NR^C R^D$ and -$L^1$-$R^4$-$(L^2)_c$-$R^5$;

$R^1$ is selected from the group consisting of hydrogen, hydroxy, $C_{1-6}$alkyl, —C(O)—$C_{1-6}$alkyl, —$C_{1-4}$alkyl-$NR^C R^D$ and -$L^1$-$R^4$-$(L^2)_c$-$R^5$;

is a five to seven membered aromatic, partially unsaturated or saturated ring structure, optionally containing one to two heteroatoms independently selected from O, N or S; wherein the heteroatom(s) are not the bridge atom(s);

a is an integer selected from 0 to 2;

$R^2$ is selected from the group consisting of halogen, hydroxy, carboxy, oxo, cyano, nitro, amino, $C_{1-4}$alkylamino, di($C_{1-4}$alkyl)amino, $C_{1-4}$alkyl, $C_{1-4}$alkoxy, halogenated $C_{1-4}$alkyl, —O-aralkyl, —C(O)—$C_{1-4}$alkyl, —C(O)O—$C_{1-4}$alkyl, —OC(O)—$C_{1-4}$alkyl, —O—$SO_2$—$C_{1-4}$alkyl, —O—$SO_2$-(halogenated $C_{1-4}$alkyl) and —O—Si($CH_3)_2$(t-butyl);

b is an integer selected from 0 to 2;

$R^3$ is selected from the group consisting of halogen, hydroxy, carboxy, oxo, cyano, nitro, amino, $C_{1-4}$alkylamino, di($C_{1-4}$alkyl)amino, $C_{1-4}$alkyl, $C_{1-4}$alkoxy, halogenated $C_{1-4}$alkyl, —O-aralkyl, —C(O)—$C_{1-4}$alkyl, —C(O)O—$C_{1-4}$alkyl, —OC(O)—$C_{1-4}$alkyl, —O—$SO_2$—$C_{1-4}$alkyl, —O—$SO_2$-(halogenated $C_{1-4}$alkyl) and O—Si($CH_3)_2$(t-butyl);

$L^1$ is selected from the group consisting of —$CH_2$— and —C(O)—;

$R^4$ is selected from the group consisting of a five to six membered aryl and a five to six membered heteroaryl;

c is an integer selected from 0 to 1;

$L^2$ is selected from the group consisting of —$C_{1-4}$alkyl-, —$C_{2-4}$alkenyl-, —O—$C_{1-3}$alkyl-, —S—$C_{1-3}$alkyl- and —$NR^B$—$C_{1-3}$alkyl-; wherein $R^B$ is selected from hydrogen or $C_{1-4}$alkyl;

$R^5$ is selected from the group consisting of —$NR^C R^D$, —C(O)—$C_{1-4}$alkyl, —$CO_2H$, —C(O)O—$C_{1-4}$alkyl and —OC(O)—$C_{1-4}$alkyl;

wherein $R^C$ and $R^D$ are independently selected from hydrogen or $C_{1-4}$alkyl; alternatively, $R^C$ and $R^D$ are taken together with the nitrogen atom to which they are bound to form a five to seven membered aromatic, partially aromatic or saturated ring structure; wherein the ring structure optionally contains one to two additional heteroatoms selected from O, N or S;

provided further that $R^A$ and $R^1$ are not each -$L^1$-$R^4$-$(L^2)_c$-$R^5$;

provided further that when a is 0 and b is 0; then one of $R^A$ or $R^1$ is -$L^1$-$R^4$-$(L^2)_c$-$R^5$;

provided further that when $R^1$ is hydrogen; and

is phenyl; then at least one of a or b is other than 0;

provided further that when X is —NH— or —N($C_{1-6}$alkyl)-; $R^1$ is hydrogen or $C_{1-6}$alkyl; a is 0 to 1; $R^2$ is halogen or —C(O)O—$C_{1-4}$alkyl; b is 1; and $R^3$ is halogen or —C(O)O—$C_{1-4}$alkyl; then

is other than phenyl;

provided further that when X is —O—; $R^1$ is hydrogen or $C_{1-4}$alkyl;

is phenyl; a is 0 to 1; b is 0 to 1; and at least one of a or b is 1; then at least one of $R^2$ or $R^3$ is other than halogen, cyano, nitro, carboxy or —C(O)O—$C_{1-4}$alkyl;

provided further that when X is —O—;

is phenyl; a is 0; and b is 0; then $R^1$ is other than —$C_{1-4}$alkyl-N($C_{1-4}$alkyl)$_2$ or —$C_{1-4}$alkyl-piperidinyl;

provided further that when X is —O—; $R^1$ is hydrogen;

is pyridyl or thienyl; a is 0; and b is 1 to 2; then $R^2$ is other than oxo, halogen or —C(O)O—$C_{1-4}$alkyl;

provided further that when X is —O—; $R^1$ is hydrogen or $C_{1-4}$alkyl;

is pyrrolyl; a is 0; and b is 1 or 2; then $R^2$ is other than $C_{1-4}$alkyl or —C(O)O—$C_{1-4}$alkyl;

provided further that when X is —S—; $R^1$ is hydrogen, $C_{1-4}$alkyl, —$C_{1-4}$alkyl-N($C_{1-4}$alkyl)$_2$, —$C_{1-4}$alkyl-piperidinyl, —$C_{1-4}$alkyl-pyrrolidinyl or —$C_{1-4}$alkyl-morpholinyl;

is phenyl; a is 0 to 2; and b is 0 to 2; then at least one of $R^2$ or $R^3$ is other than halogen, $C_{1-4}$alkyl, $C_{1-4}$alkoxy, cyano, nitro, amino or —C(O)O—$C_{1-4}$alkyl;

or a pharmaceutically acceptable salt thereof.

The present invention is further directed to compounds of formula (II)

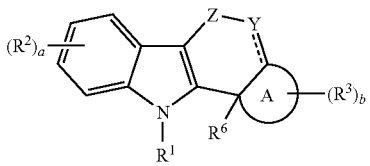

(II)

wherein

Y is selected from the group consisting of —O—, —S—, —SO—, —SO$_2$—, —N=, —NH— and —N(CH$_3$)—; and Z is selected from the group consisting of —CH$_2$—, —CH(CH$_3$)—, —C(CH$_3$)$_2$— and —CH(OH)—;

alternatively, Y is —CH$_2$—; and Z is selected from the group consisting of —O—, —S—, —SO— and —SO$_2$—;

alternatively, Y is —CH=; and Z is selected from the group consisting of —CH$_2$—, —O—, —S—, —SO— and —SO$_2$—;

alternatively, Y is selected from the group consisting of —CH$_2$—, —O—, —S—, —SO— and —SO$_2$—; and Z is selected from the group consisting of —CH$_2$CH$_2$— and —CH=CH—; ----represents an optional double bond;

$R^1$ is selected from the group consisting of hydrogen, hydroxy, $C_{1-6}$alkyl, —C(O)—$C_{1-6}$alkyl, —$C_{1-4}$alkyl-NR$^C$R$^D$ and -L$^1$-R$^4$-(L$^2$)$_c$-R$^5$;

is a five to seven membered aromatic, partially unsaturated or saturated ring structure, optionally containing one to two heteroatoms independently selected from O, N or S; wherein the heteroatom(s) are not the bridge atom(s);

$R^6$ is selected from the group consisting of hydrogen, $C_{1-3}$alkyl and CF$_3$;

a is an integer selected from 0 to 2;

$R^2$ is selected from the group consisting of halogen, hydroxy, carboxy, oxo, cyano, nitro, amino, $C_{1-4}$alkylamino, di($C_{1-4}$alkyl)amino, $C_{1-4}$alkyl, $C_{1-4}$alkoxy, halogenated $C_{1-4}$alkyl, —O-aralkyl, —C(O)—$C_{1-4}$alkyl, —C(O)O—$C_{1-4}$alkyl, —OC(O)—$C_{1-4}$alkyl, —O—SO$_2$—$C_{1-4}$alkyl, —O—SO$_2$-(halogenated $C_{1-4}$alkyl) and —O—Si(CH$_3$)$_2$(t-butyl);

b is an integer selected from 0 to 2;

$R^3$ is selected from the group consisting of halogen, hydroxy, carboxy, oxo, cyano, nitro, amino, $C_{1-4}$alkylamino, di($C_{1-4}$alkyl)amino, $C_{1-4}$alkyl, $C_{1-4}$alkoxy, halogenated $C_{1-4}$alkyl, —O-aralkyl, —C(O)—$C_{1-4}$alkyl, —C(O)O—$C_{1-4}$alkyl, —OC(O)—$C_{1-4}$alkyl, —O—SO$_2$—$C_{1-4}$alkyl, —O—SO$_2$-(halogenated $C_{1-4}$alkyl) and —O—Si(CH$_3$)$_2$(t-butyl);

$L^1$ is selected from the group consisting of —CH$_2$— and —C(O)—;

$R^4$ is selected from the group consisting of a five to six membered aryl and a five to six membered heteroaryl;

c is an integer selected from 0 to 1;

$L^2$ is selected from the group consisting of —$C_{1-4}$alkyl-, —$C_{2-4}$alkenyl-, —O—$C_{1-3}$alkyl-, —S—$C_{1-3}$alkyl- and —NR$^B$—$C_{1-3}$alkyl-; wherein R$^B$ is selected from hydrogen or $C_{1-4}$alkyl;

$R^5$ is selected from the group consisting of —NR$^C$R$^D$, —C(O)—$C_{1-4}$alkyl, —CO$_2$H, —C(O)O—$C_{1-4}$alkyl and —OC(O)—$C_{1-4}$alkyl;

wherein R$^C$ and R$^D$ are independently selected from hydrogen or $C_{1-4}$alkyl; alternatively, R$^C$ and R$^D$ are taken together with the nitrogen atom to which they are bound to form a five to seven membered aromatic, partially aromatic or saturated ring structure; wherein the ring structure optionally contains one to two additional heteroatoms selected from O, N or S;

provided that when $R^1$ is hydrogen or methyl; $R^6$ is hydrogen; and

is phenyl, pyridyl or thienyl; then at least one of a or b is other than 0;

provided further that when Y is —NH—; Z is —CH$_2$—; $R^1$ is hydrogen, $R^6$ is hydrogen, a is 1, $R^2$ is methyl; b is 0 to 1; and $R^3$ is halogen or methoxy; then

is other than 2-pyridyl;

provided further that when Y is —N(CH$_3$)—; Z is —C(CH$_3$)$_2$—; $R^1$ is methyl, $R^6$ is hydrogen; a is 0; b is 1; and $R^3$ is hydroxy; then

is other than phenyl;

provided further that when Y is —CH$_2$—; Z is —O—; R$^6$ is hydrogen; a is 0; b is 0; and (A)

is phenyl; then R$^1$ is other than C$_{1-4}$alkyl or —C(O)—C$_{1-3}$alkyl;

provided further that when Y is —CH$_2$—; Z is —O—; R$^1$ is hydrogen; R$^6$ is hydrogen;

(A)

is phenyl; a is 1; and b is 0; then R$^2$ is other than halogen, nitro or C$_{1-4}$alkoxy;

provided further that when Y is —CH$_2$—; Z is —CH$_2$CH$_2$—; R$^1$ is hydrogen, R$^6$ is hydrogen, (A)

is phenyl; a is 1; and b is 0; then R$^2$ is other than halogen;

provided further that when Y is —CH$_2$—; Z is —CH$_2$CH$_2$—; R$^1$ is hydrogen, R$^6$ is hydrogen;

(A)

is pyrazolyl; a is 1; and b is 0; then R$^2$ is other than C$_{1-4}$alkoxy;

provided further that when Y is —CH$_2$—; Z is —CH$_2$CH$_2$—; R$^1$ is hydrogen, R$^6$ is hydrogen;

(A)

is thienyl; a is 0; and b is 1; then R$^3$ is other than C$_{1-4}$alkyl;

provided further that when Y is —CH$_2$—; Z is —CH$_2$CH$_2$—; R$^1$ is hydrogen or C$_{1-4}$alkyl-N(C$_{1-4}$alkyl)$_2$; R$^6$ is hydrogen;

(A)

is phenyl; a is 1; R$^2$ is nitro; and b is 2; then at least one R$^3$ is other than C$_{1-4}$alkoxy;

provided further that when Y is —O—; Z is —CH$_2$CH$_2$—; R$^1$ is hydrogen; R$^6$ is hydrogen; a is 1; R$^2$ is methyl; b is 1; and R$^3$ is methyl; then (A)

is other than phenyl;

provided further that when Y is —O—; Z is —CH$_2$CH$_2$—; R$^1$ is hydrogen; R$^6$ is hydrogen;

(A)

is phenyl; a is o to 1; and b is 0; then R$^2$ is other than halogen, nitro, amino, —C$_{1-4}$alkoxy or —C(O)O—C$_{1-4}$alkyl;

provided further that when Y is —O—; Z is —CH$_2$CH$_2$—; R$^6$ is hydrogen;

(A)

is phenyl; a is 1; R$^2$ is methyl; and b is 0; then R$^1$ is other than —C$_{1-4}$alkyl-N(CH$_3$)$_2$ or —C$_{1-4}$alkyl-(4-methyl-piperidinyl);

provided further that when Y is —S—, —SO— or —SO$_2$—; Z is —CH$_2$CH$_2$—; R$^1$ is hydrogen or C$_{1-4}$alkyl; R$^6$ is hydrogen, (A)

is phenyl; a is 1; and b is 0; then R$^2$ is other than C$_{1-4}$alkyl, carboxy or —C(O)O—C$_{1-4}$alkyl;

provided further that when Y is —S—; Z is —CH$_2$CH$_2$; R$^6$ is hydrogen;

(A)

is phenyl; a is 0; and b is 0; then R$^1$ is other than —C$_{1-4}$alkyl-N(CH$_3$)$_2$;

provided further that when Y is —O—; Z is —CH$_2$—; R$^1$ is hydrogen; R$^6$ is hydrogen;

(A)

is phenyl; a is 1; b is 0; then R$^2$ is other than C$_{1-4}$alkyl or C$_{1-4}$alkoxy;

provided further that when Y is —O—; Z is —CH$_2$—; R$^1$ is C$_{1-4}$alkyl; R$^6$ is hydrogen;

(A)

is phenyl; a is 1; b is 0; then $R^2$ is other than —C(O)O—$C_{1-4}$ alkyl;

provided further that when Y is —O—; Z is —CH$_2$—; $R^1$ is hydrogen; $R^6$ is hydrogen;

(A)

is phenyl; a is 0; b is 1; then $R^3$ is other than halogen or $C_{1-4}$alkyl;

provided further that when Y is —O—; Z is CH$_2$—; $R^6$ is hydrogen;

(A)

is phenyl; a is 0; and b is 0; then $R^1$ is other than —$C_{1-4}$alkyl-N(CH$_3$)$_2$;

provided further that when Y is —S—; Z is —C(CH$_3$)$_2$—; $R^1$ is hydrogen; $R^6$ is hydrogen, (A)

is phenyl; a is 0; and b is 1; then $R^3$ is other than halogen;

provided further that when Y is —S—; Z is —CH$_2$—; $R^1$ is hydrogen; $R^6$ is hydrogen;

(A)

is phenyl; a is 1; and b is 0; then $R^2$ is other than halogen, $C_{1-4}$alkyl, $C_{1-4}$alkoxy, carboxy, trifluoromethyl or —C(O)O—$C_{1-4}$alkyl;

provided further that when Y is —S—; Z is —CH$_2$—; $R^1$ is hydrogen; $R^6$ is hydrogen;

(A)

is phenyl; a is 2; and b is 0; then the two $R^2$ groups are selected to be other than (halogen and $C_{1-4}$alkyl), (hydroxy and $C_{1-4}$alkyl), ($C_{1-4}$alkyl and $C_{1-4}$alkyl), ($C_{1-4}$alkyl and $C_{1-4}$alkoxy) or (halogen and halogen);

provided further than when Y is —S—, —SO— or —SO$_2$—; Z is —CH$_2$—; $R^1$ is hydrogen; $R^6$ is hydrogen;

(A)

is phenyl; a is 0; and b is 1; then $R^3$ is other than halogen, $C_{1-4}$alkyl, $C_{1-4}$alkoxy, trifluoromethyl, nitro or amino;

provided further than when Y is —S—; Z is —CH$_2$—; $R^1$ is hydrogen; $R^6$ is hydrogen;

(A)

is phenyl; a is 1; $R^2$ is $C_{1-4}$alkyl or halogen; and b is 1; then $R^3$ is other than halogen or $C_{1-4}$alkyl;

provided further than when Y is —S—; Z is —CH$_2$—; $R^1$ is hydrogen; $R^6$ is hydrogen;

(A)

is phenyl; a is 1; $R^2$ is —C(O)O—$C_{1-4}$alkyl; and b is 1; then $R^3$ is other than $C_{1-4}$alkyl;

provided further that when Y is —SO$_2$—; Z is —CH$_2$—; $R^1$ is hydrogen; $R^6$ is hydrogen;

(A)

is phenyl; a is 1; and b is 0; then $R^2$ is other than carboxy, $C_{1-4}$alkoxy or —C(O)O—$C_{1-4}$alkyl;

provided further that when Y is —S—, —SO— or —SO$_2$—; Z is —CH$_2$—; $R^1$ is $C_{1-4}$alkyl; $R^6$ is hydrogen, (A)

is phenyl; a is 1; and b is 0; then $R^2$ is other than carboxy or —C(O)O—$C_{1-4}$alkyl;

provided further that when Y is —S—, —SO— or —SO$_2$—; Z is —CH$_2$—; $R^6$ is hydrogen;

(A)

is phenyl, a is 0; and b is 0; then $R^1$ is other than —$C_{1-4}$alkyl-N(CH$_3$)$_2$;

provided further that when Y is —S—; Z —CH$_2$—; $R^1$ is hydrogen; $R^6$ is hydrogen; a is 1; $R^2$ is halogen or $C_{1-4}$alkoxy; b is 1; and $R^3$ is $C_{1-4}$alkyl; then (A)

is other than cyclopentyl or 2-pyridyl;

provided further that when Y is —S—; Z —CH₂—; R¹ is hydrogen; R⁶ is hydrogen; a is 0; b is 1; and R³ is C₁₋₄alkyl; then (A)

is other than 2-pyridyl;

provided further that when Y is —S—; Z —CH₂—; R¹ is hydrogen; R⁶ is hydrogen; a is 1; R² is halogen or C₁₋₄alkoxy; then (A)

is other than 2-pyridyl;

provided further that when Y is —S—; Z —CH₂—; R¹ is hydrogen; R⁶ is hydrogen; a is 0; b is 2; and each R³ is C₁₋₄alkyl; then (A)

is other than 2-thienyl;

provided further that when Y is —S—; Z is —C(CH₃)₂—; R¹ is hydrogen; R⁶ is hydrogen; a is 0; b is 2; one R³ is C₁₋₄alkyl and the other R³ is oxo; then (A)

is other than 3-pyrrolidinyl;

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by one or more sex steroid hormone receptors, in a subject in need thereof, comprising administering to the subject a therapeutically effective amount of any of the compounds or pharmaceutical compositions described above.

Further exemplifying the invention are methods of treating a disorder mediated by one or more estrogen, androgen or progestin receptors, in a subject in need thereof, comprising administering to the subject a therapeutically effective amount of any of the compounds or pharmaceutical compositions described above.

An example of the invention is a method for treating a disorder or condition selected from the group consisting of hot flashes, vaginal dryness, osteopenia, osteoporosis, hyperlipidemia, loss of cognitive function, degenerative brain diseases, cardiovascular diseases, cerebrovascular diseases, hormone sensitive cancers and hyperplasia (in tissues including breast, endometrium, and cervix in women and prostate in men), endometriosis, uterine fibroids, osteoarthritis, prostate carcinoma, benign prostatic hyperplasia (BPH), hirsitutism, alopecia, anorexia nervosa, breast cancer, acne, AIDS, cachexia, endometriosis (preferably, without associated bone loss and/or hypoestrogenism), myoma (preferably, without associated bone loss and/or hypoestrogenism), dysfunctional bleeding, tumors containing steroid receptors, male contraception, female contraception, male performance enhancement, and hormone replacement, in a subject in need thereof, comprising administering to the subject an effective amount of any of the compounds or pharmaceutical compositions described above.

Another example of the invention is the use of any of the compounds described herein in the preparation of a medicament for treating: (a) hot flashes, (b) vaginal dryness, (c) osteopenia, (d) osteoporosis, (e) hyperlipidemia, (f) loss of cognitive function, (g) degenerative brain diseases, (h) cardiovascular diseases, (i) cerebrovascular diseases, (j) hormone sensitive cancers, (k) hormone sensitive hyperplasia, (l) endometriosis, (m) uterine fibroids, (n) osteoarthritis, (O) prostate carcinoma, (p) benign prostatic hyperplasia, (q) hirsitutism, (r) alopecia, (s) anorexia nervosa, (t) breast cancer, (u) acne, (v) AIDS, (w) cachexia, (x) endometriosis, (y) myoma, (z) dysfunctional bleeding, (aa) tumors containing steroid receptors, (bb) for male contraception, (cc) for female contraception, (dd) for male performance enhancement or (dd) for hormone replacement in a subject in need thereof.

DETAILED DESCRIPTION OF THE INVENTION

The present invention is directed to compounds of formula (I) and compounds of formula (II)

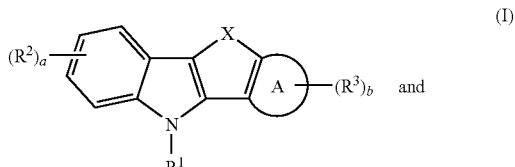

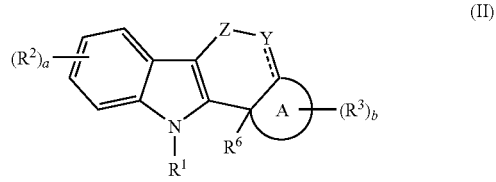

wherein X, Y, Z, a, b, R¹, R², R³, R⁶, ----and (A)

are as herein defined, useful for the treatment and/or prevention of disorders or conditions mediated by one or more sex steroid hormone receptors, more particularly, one or more estrogen, androgen and/or progestin receptors.

In an embodiment, the compounds of the present invention are useful for the treatment of estrogen receptor modulated disorders. In another embodiment, the compounds of the present invention are useful for the treatment of disorders mediated by the estrogen-α and/or estrogen-β receptor. In yet another embodiment, the compounds of the present invention are useful for the treatment of an estrogen mediated disorder selected from the group consisting of the treatment and/or prevention of disorders associated with the depletion of estrogen, hormone sensitive cancers and hyperplasia, endometriosis, uterine fibroids, osteoarthritis and as contraceptive agents, alone or in combination with a progestogen or progestogen antagonist.

More particularly, the compounds of the present invention are useful for the treatment and/or prevention of a condition or disorder selected from the group consisting of hot flashes, vaginal dryness, osteopenia, osteoporosis, hyperlipidemia, loss of cognitive function, degenerative brain diseases, cardiovascular diseases, cerebrovascular diseases, cancer or hyperplasia of the breast tissue, cancer or hyperplasia of the endometrium, cancer or hyperplasia of the cervix, cancer or hyperplasia of the prostate, endometriosis, uterine fibroids and osteoarthritis; and as a contraceptive agent. Preferably, the disorder is selected from the group consisting of osteoporosis, hot flashes, vaginal dryness, breast cancer, and endometriosis.

In an embodiment, the compounds of the present invention are useful for the treatment of androgen receptor modulated disorders. In another embodiment, the compounds of the present invention are useful for the treatment of an androgen receptor modulated disorder selected from the group consisting of prostate carcinoma, benign prostatic hyperplasia, hirsutism, or for male contraception. In yet another embodiment, the compounds of the present invention are useful for the treatment of prostate carcinoma, benign prostatic hyperplasia, hirsutism, alopecia, anorexia nervosa, breast cancer, acne, AIDS, cachexia, for male contraception, and/or for male performance enhancement.

In an embodiment, the compounds of the present invention are useful in the treatment of progestin modulated disorders. More particularly, the compounds of the present invention are useful as contraceptives, for the treatment of endometriosis (preferably without associated bone loss and/or hypoestrogenism), myoma (preferably, without associated bone loss and/or hypoestrogenism), dysfunctional bleeding, tumors containing steroid receptors and/or as an adjunct to estrogens in hormone replacement therapy.

In an embodiment of the present invention are compounds of formula (I) which are useful in the treatment of estrogen receptor modulated disorders and diseases. In an embodiment of the present invention are compounds of formula (II) which are useful in the treatment of estrogen receptor modulated disorders and diseases.

In an embodiment of the present invention are compounds of formula (I) which are useful in the treatment of androgen receptor modulated disorders and diseases. In an embodiment of the present invention are compounds of formula (II) which are useful in the treatment of androgen receptor modulated disorders and diseases.

In an embodiment of the present invention are compounds of formula (I) which are useful in the treatment of progestin receptor modulated disorders and diseases. In an embodiment of the present invention are compounds of formula (I) which are useful in the treatment of progestin receptor modulated disorders and diseases.

In an embodiment of the present invention Y is selected from the group consisting of —O—, —S—, —SO— and —$SO_2$—; and Z is selected from the group consisting of —$CH_2$—, —$CH(CH_3)$—, $C(CH_3)_2$— and —CH(OH)—. In another embodiment of the present invention Y is selected from the group consisting of —N=, —NH— and —N($CH_3$)—; and Z is selected from the group consisting of —$CH_2$—, —$CH(CH_3)$—, $C(CH_3)_2$— and —CH(OH)—.

In an embodiment of the present invention Y is —$CH_2$—; and Z is selected from the group consisting of —O—, —S—, —SO— and —$SO_2$—. In another embodiment of the present invention, Y is —CH=; and Z is of —$CH_2$—. In yet another embodiment of the present invention, Y is —CH=; and Z is selected from the group consisting of —O—, —S—, —SO— and —$SO_2$—.

In an embodiment of the present invention Y is —$CH_2$—; and Z is selected from the group consisting of —$CH_2CH_2$— and —CH=CH—. In another embodiment of the present invention, Y is selected from the group consisting of —O—, —S—, —SO— and —$SO_2$; and Z is selected from the group consisting of —$CH_2CH_2$— and —CH=CH—.

In an embodiment of the present invention Y is selected from the group consisting of —O—, —S—, —SO—, —$SO_2$—, —NH— and —N($CH_3$)—; and Z is selected from the group consisting of —$CH_2$—, —$C(CH_3)_2$— and —CH(OH)—.

In an embodiment of the present invention, Y is —$CH_2$—; and Z is selected from the group consisting of —S—, —SO— and —$SO_2$—. In another embodiment of the present invention, Y is —$CH_2$—; and Z is —S—.

In an embodiment of the present invention, Y is —CH=; and Z is —$CH_2$—.

In an embodiment of the present invention, Y is selected from the group consisting of —$CH_2$—, —S—, —SO— and —$SO_2$—; and Z is selected from the group consisting of —$CH_2CH_2$— and —CH=CH—. In another embodiment of the present invention, Y is selected from the group consisting of —$CH_2$—, —S— and —SO—; and Z is selected from the group consisting of —$CH_2CH_2$— and —CH=CH—.

In an embodiment of the present invention X is O.

In an embodiment of the present invention a is an integer from 0 to 1. In another embodiment of the present invention b is and integer from 0 to 1. In yet another embodiment of the present invention a is 1 and b is 1. In yet another embodiment of the present invention c is 1.

In an embodiment of the present invention $R^1$ is selected from the group consisting of hydrogen and -$L^1$-$R^4$-$(L^2)_c$-$R^5$. Preferably, $R^1$ is selected from the group consisting of hydrogen and —$CH_2$-phenyl-O—$C_{1-3}$alkyl-$NR^BR^C$. More preferably, $R^1$ is selected from the group consisting of hydrogen and 4-(diethylamino-ethoxy)-benzyl.

In an embodiment of the present invention, $R^1$ is selected from the group consisting of hydrogen, hydroxy, $C_{1-4}$alkyl, —C(O)—$C_{1-4}$alkyl, —$C_{1-4}$alkyl-$NR^CR^D$ and -$L^1$-$R^4$-$(L^2)_c$-$R^5$. In another embodiment of the present invention, $R^1$ is selected from the group consisting of hydrogen, hydroxy, methyl, ethyl, methylcarbonyl-, dimethylamino-ethyl, 4-(diethylamino-ethoxy)-benzyl, 4-(piperidinyl-ethoxy)-benzyl, 4-(pyrrolidinyl-ethoxy)-benzyl, 4-(piperidinyl-ethoxy)-phenyl-carbonyl and 4-(methyl-carbonyloxy)-phenyl-carbonyl.

In an embodiment of the present invention, $R^1$ is selected from the group consisting of hydrogen, hydroxy, $C_{1-4}$alkyl, —C(O)—$C_{1-4}$alkyl, —$C_{1-4}$alkyl-$NR^CR^D$ and -$L^1$-$R^4$-$(L^2)_c$-$R^5$. In another embodiment of the present invention, $R^1$ is selected from the group consisting of hydrogen, hydroxy, methyl, ethyl, methylcarbonyl-, dimethylamino-ethyl, 4-(diethylamino-ethoxy)-benzyl, 4-(piperidinyl-ethoxy)-benzyl, 4-(piperidinyl-ethoxy)-phenyl-carbonyl and 4-(methyl-carbonyloxy)-phenyl-carbonyl.

In an embodiment of the present invention, $R^1$ is selected from the group consisting of hydrogen, $C_{1-4}$alkyl, and -$L^1$-$R^4$-$(L^2)_c$-$R^5$. In an embodiment of the present invention, R¹ is selected from the group consisting of hydrogen, methyl, 4-(piperidinyl-ethoxy)-benzyl and 4-(pyrrolidinyl-ethoxy)-benzyl.

In an embodiment of the present invention, R¹ is selected from the group consisting of hydrogen, hydroxy, $C_{1-6}$alkyl, —C(O)—$C_{1-6}$alkyl, —$C_{1-4}$alkyl-NR$^C$R$^D$ and -L$^1$-R$^4$-(L$^2$)$_c$-R$^5$. In another embodiment of the present invention, R¹ is selected from the group consisting of hydrogen, hydroxy, $C_{1-4}$alkyl, —C(O)—$C_{1-4}$alkyl, —$C_{1-4}$alkyl-NR$^C$R$^D$ and -L$^1$-R$^4$-(L$^2$)$_c$-R$^5$. In another embodiment of the present invention, R¹ is selected from the group consisting of hydrogen, hydroxy, methyl, ethyl, methylcarbonyl-, diethylamino-ethyl-, 4-(piperidinyl-ethoxy)-benzyl-, 4-(pyrrolidinyl-ethoxy)-benzyl-, 4-(diethylamino-ethoxy)-benzyl-, 4-(piperidinyl-ethoxy)-phenyl-carbonyl- and 4-(methyl-carbonyloxy)-phenyl-carbonyl.

In an embodiment of the present invention, R¹ is selected from the group consisting of hydrogen, $C_{1-2}$alkyl and -L$^1$-R$^4$-(L$^2$)$_c$-R$^5$. In another embodiment of the present invention, R¹ is selected from the group consisting of —$C_{1-4}$alkyl-NR$^C$R$^D$ and -L$^1$-R$^4$-(L$^2$)$_c$-R$^5$. In another embodiment of the present invention, R¹ is -L$^1$-R$^4$-(L$_2$)$_c$-R$^5$. In yet another embodiment of the present invention, R¹ is —$C_{1-4}$alkyl-NR$^C$R$^D$.

In an embodiment of the present invention, when R¹ is other than $C_{1-6}$alkyl. In another embodiment of the present invention, R¹ is other than hydrogen of $C_{1-6}$alkyl.

In an embodiment of the present invention, (A)

is a five to six membered aromatic, partially unsaturated or saturated ring structure, optionally containing one to two heteroatoms independently selected from O or N; wherein the heteroatom(s) are not the bridge atom(s). In another embodiment of the present invention, (A)

is a five to six membered aromatic ring structure, optionally containing one to two heteroatoms independently selected from O or N; wherein the heteroatom(s) are not the bridge atom(s). In another embodiment of the present invention (A)

is a six membered aromatic, partially unsaturated or saturated ring structure, optionally containing one to two heteroatoms independently selected from O, N or S; wherein the heteroatom(s) are not the bridge atom(s). In another embodiment of the present invention (A)

is a six membered aromatic or saturated ring structure, optionally containing one to two heteroatoms independently selected from O, N or S; wherein the heteroatom(s) are not the bridge atom(s). In another embodiment of the present invention, (A)

is phenyl. In yet another embodiment of the present invention (A)

selected from the group consisting of phenyl, pyrrolyl, thienyl, pyridyl, pyrazinyl, pyrazolyl, piperidinyl and cyclohexen-1-yl (i.e.

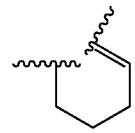

). In yet another embodiment of the present invention, (A)

is selected from the group consisting of phenyl, 2-pyridyl and piperidinyl.

In an embodiment of the present invention R⁶ is selected from the group consisting of hydrogen and $C_{1-3}$alkyl. Preferably, R⁶ is selected from the group consisting of hydrogen and methyl. In another embodiment of the present invention R⁶ is selected from the group consisting of hydrogen, methyl and $CF_3$.

In an embodiment of the present invention R² is $C_{1-4}$alkoxy. Preferably, R² is methoxy.

In an embodiment of the present invention, R² is selected from the group consisting of halogen, hydroxy, carboxy, oxo, cyano, nitro, amino, $C_{1-4}$alkylamino, di($C_{1-4}$alkyl)amino, $C_{1-4}$alkoxy, halogenated $C_{1-4}$alkyl, —C(O)—$C_{1-4}$alkyl, —C(O)O—$C_{1-4}$alkyl, —OC(O)—$C_{1-4}$alkyl, —O—$SO_2$—$C_{1-4}$alkyl, —O—$SO_2$— (halogenated $C_{1-4}$alkyl) and —O—Si($CH_3$)$_2$(t-butyl).

In an embodiment of the present invention, R² is selected from the group consisting of hydroxy, carboxy, halogen, $C_{1-4}$alkoxy, cyano, —C(O)O—$C_{1-4}$alkyl, —OC(O)—$C_{1-4}$alkyl, —O—$SO_2$—$C_{1-4}$alkyl, —O—$SO_2$-(halogenated $C_{1-4}$alkyl) and —O—Si($CH_3$)$_2$(t-butyl). In another embodiment of the present invention, R² is selected from the group consisting of hydroxy, carboxy, chloro, fluoro, bromo, methoxy, cyano, methoxy-carbonyl-, methyl-carbonyloxy-, methyl-sulfonyloxy-, trifluoromethyl-sulfonyloxy-, 1,1,2,2,3,3,4,4,4-nonafluorobutyl-sulfonyloxy-, t-butyl-carbonyloxy- and t-butyl-dimethyl-silyloxy-.

In an embodiment of the present invention, R² is selected from the group consisting of hydroxy, carboxy, halogen, $C_{1-4}$alkoxy, cyano, —C(O)O—$C_{1-4}$alkyl, —OC(O)—$C_{1-4}$alkyl, —O—SO$_2$—$C_{1-4}$alkyl, —O—SO$_2$-(halogenated $C_{1-4}$alkyl) and —O—Si(CH$_3$)$_2$(t-butyl). In another embodiment of the present invention, $R^2$ is selected from the group consisting of hydroxy, carboxy, chloro, fluoro, bromo, methoxy, cyano, methoxy-carbonyl-, methyl-carbonyloxy-, methyl-sulfonyloxy-, trifluoromethyl-sulfonyloxy-, 1,1,2,2,3,3,4,4,4-nonafluorobutyl-sulfonyloxy-, t-butyl-carbonyloxy- and t-butyl-dimethyl-silyloxy-.

In an embodiment of the present invention, $R^2$ is selected from the group consisting of hydroxy and $C_{1-4}$alkoxy. In another embodiment of the present invention, $R^2$ is selected from the group consisting of hydroxy and methoxy.

In an embodiment of the present invention, $R^2$ is selected from the group consisting of halogen, hydroxy, carboxy, cyano, nitro, amino, $C_{1-4}$alkylamino, di($C_{1-4}$alkyl)amino, $C_{1-4}$alkoxy, —O-aralkyl, —C(O)O—$C_{1-4}$alkyl, —OC(O)—$C_{1-4}$alkyl, —O—SO$_2$—$C_{1-4}$alkyl, —O—SO$_2$-(halogenated $C_{1-4}$alkyl) and —O—Si(CH$_3$)$_2$(t-butyl). In another embodiment of the present invention, $R^2$ is selected from the group consisting of halogen, hydroxy, carboxy, cyano, $C_{1-4}$alkoxy, —C(O)O—$C_{1-4}$alkyl, —OC(O)—$C_{1-4}$alkyl, —O—SO$_2$-(halogenated $C_{1-4}$alkyl) and —O—Si(CH$_3$)$_2$(t-butyl). In another embodiment of the present invention, $R^2$ is selected from the group consisting of hydroxy, carboxy, chloro, fluoro, bromo, methoxy, cyano, methoxy-carbonyl-, methyl-carbonyloxy-, t-butyl-carbonyloxy-, trifluoromethyl-sulfonyloxy-, (1,1,2,2,3,3,4,4,4-nonafluorobutyl)-sulfonyloxy- and (t-butyl-dimethyl-silyloxy)-.

In an embodiment of the present invention, $R^3$ is selected from the group consisting of hydroxy and —O-aralkyl. Preferably, $R^3$ is selected from the group consisting of hydroxy and benzyloxy.

In an embodiment of the present invention, $R^3$ is selected from the group consisting of halogen, hydroxy, carboxy, oxo, cyano, nitro, amino, $C_{1-4}$alkylamino, di($C_{1-4}$alkyl)amino, $C_{1-4}$alkyl, $C_{1-4}$alkoxy, halogenated $C_{1-4}$alkyl, —O-aralkyl, —C(O)—$C_{1-4}$alkyl, —C(O)O—$C_{1-4}$alkyl, —OC(O)—$C_{1-4}$alkyl, —O—SO$_2$—$C_{1-4}$alkyl, —O—SO$_2$-(halogenated $C_{1-4}$alkyl) and —O—Si(CH$_3$)$_2$(t-butyl).

In an embodiment of the present invention, $R^3$ is selected from the group consisting of halogen, hydroxy, carboxy, oxo, amino, $C_{1-4}$alkyl, $C_{1-4}$alkoxy, halogenated $C_{1-4}$alkyl, —O-aralkyl and —O—Si(CH$_3$)$_2$(t-butyl). In another embodiment of the present invention, $R^3$ is selected from the group consisting of hydroxy, carboxy, oxo, bromo, fluoro, methyl, methoxy, trifluoromethyl, benzyloxy, amino and t-butyl-dimethyl-silyloxy-.

In an embodiment of the present invention, $R^3$ is selected from the group consisting of halogen, hydroxy, carboxy, oxo, amino, $C_{1-4}$alkyl, $C_{1-4}$alkoxy, halogenated $C_{1-4}$alkyl, —O-aralkyl and —O—Si(CH$_3$)$_2$(t-butyl). In another embodiment of the present invention, $R^3$ is selected from the group consisting of hydroxy, carboxy, oxo, bromo, fluoro, methyl, methoxy, trifluoromethyl, benzyloxy, amino and t-butyl-dimethyl-silyloxy-.

In an embodiment of the present invention, $R^3$ is selected from the group consisting of hydroxy and $C_{1-4}$alkoxy. In another embodiment of the present invention, $R^3$ is selected from the group consisting of hydroxy and methoxy.

In an embodiment of the present invention, $R^3$ is selected from the group consisting of halogen, hydroxy, carboxy, oxo, $C_{1-4}$alkyl, $C_{1-4}$alkoxy, halogenated $C_{1-4}$alkyl, —O-aralkyl, —OC(O)—$C_{1-4}$alkyl, —O—SO$_2$—$C_{1-4}$alkyl, —O—SO$_2$-(halogenated $C_{1-4}$alkyl) and —O—Si(CH$_3$)$_2$(t-butyl). In another embodiment of the present invention, $R^3$ is selected from the group consisting of hydroxy, carboxy, oxo, $C_{1-4}$alkyl, $C_{1-4}$alkoxy, halogenated $C_{1-4}$alkyl, —O-aralkyl, and —O—Si(CH$_3$)$_2$(t-butyl). In another embodiment of the present invention, $R^3$ is selected from the group consisting of hydroxy, carboxy, oxo, methyl, methoxy, benzyloxy, bromo, fluoro, trifluoromethyl and (t-butyl-dimethyl-silyloxy)-.

In an embodiment of the present invention, $L^1$ is —CH$_2$—.

In an embodiment of the present invention, $R^4$ is selected from the group consisting of six membered aryl and six membered heteroaryl. In another embodiment of the present invention, $R^4$ is phenyl.

In an embodiment of the present invention, $L^2$ is selected from the group consisting of $C_{1-4}$alkyl- and —O—$C_{1-3}$alkyl-. In another embodiment of the present invention, $L^2$ is —O—$C_{1-3}$alkyl. In another embodiment of the present invention, $L^2$ is selected from the group consisting of —O—$C_{1-3}$alkyl-, —S—$C_{1-3}$alkyl- and —NR$^B$—$C_{1-3}$alkyl; wherein R$^B$ is selected from hydrogen or $C_{1-4}$alkyl.

In an embodiment of the present invention, $R^5$ is selected from the group consisting of —NR$^B$R$^C$, —CO$_2$H and —CO$_2$—$C_{1-4}$alkyl. In another embodiment of the present invention, $R^5$ is selected from the group consisting of —CO$_2$—$C_{1-4}$alkyl and —NR$^C$R$^D$; wherein R$^C$ and R$^D$ are independently selected from hydrogen or $C_{1-4}$alkyl; alternatively, R$^C$ and R$^D$ are taken together with the nitrogen atom to which they are bound to form a five to seven membered aromatic, partially aromatic or saturated ring structure; wherein the ring structure optionally contains one to two additional heteroatoms selected from O, N or S.

In an embodiment of the present invention, $R^5$ is —NR$^C$R$^D$; wherein R$^C$ and R$^D$ are independently selected from hydrogen or $C_{1-4}$alkyl; alternatively, R$^C$ and R$^D$ are taken together with the nitrogen atom to which they are bound to form a five to seven membered aromatic, partially aromatic or saturated ring structure; wherein the ring structure optionally contains one to two additional heteroatoms selected from O, N or S.

In an embodiment of the present invention Y is —CH$_2$—; Z is —CH$_2$—; $R^1$ is selected from the group consisting of hydrogen, $C_{1-4}$alkyl and —$C_{1-4}$alkyl-NR$^C$R$^D$; $R^6$ is hydrogen; a is 1; $R^2$ is selected from the group consisting of hydroxy and $C_{1-4}$alkoxy; b is an integer from 0 to 1; $R^3$ is selected from the group consisting of oxo, $C_{1-4}$alkyl, amino, $C_{1-4}$alkylamino and di($C_{1-4}$alkyl)amino;

(A)

is selected from the group consisting of cyclohexenyl, phenyl, thienyl, pyrrolyl, pyridyl, pyrazinyl and pyrazolyl; wherein R$^C$ and R$^D$ are independently selected from hydrogen and $C_{1-4}$alkyl; alternatively, R$^C$ and R$^D$ are taken together with the nitrogen atom to which they are bound to form a five to seven membered aromatic, partially aromatic or saturated ring structure; wherein the ring structure optionally contains one to two additional heteroatoms selected from O, N or S.

In another embodiment of the present invention, Y is —CH$_2$—; Z is —CH$_2$—; $R^1$ is selected from the group consisting of hydrogen, methyl and —$C_{1-4}$alkyl-NR$^C$R$^D$; $R^6$ is hydrogen; a is 1; $R^2$ is selected from the group consisting of hydroxy and methoxy; b is an integer from 0 to 1; $R^3$ is selected from the group consisting of oxo, methyl and amino;

is selected from the group consisting of cyclohexenyl, phenyl, thienyl, pyrrolyl, pyridyl, pyrazinyl and pyrazolyl.

Additional embodiments of the present invention, include those wherein the substituents selected for one or more of the variables defined herein (i.e. X, Y, Z, a, b, $R^1$, $R^2$, $R^3$, $R^6$, ----and

) are independently selected to be any individual substituent or any subset of substituents selected from the complete list as defined herein.

In an embodiment of the present invention, are compounds selected from those listed in any of the individual Tables below. In another embodiment of the present invention, are compounds selected from any of those listed in Table 3-6 below. In another embodiment of the present invention, are compounds selected from any of those listed in Table 2 below.

In an embodiment of the present invention are compounds selected from the group listed in Table 1. In another embodiment of the present invention are compounds selected from the group listed in Table 3. In another embodiment of the present invention are compounds selected from the group listed in Table 4. In another embodiment of the present invention are compounds selected from the group listed in Table 5.

In another embodiment of the present invention are compounds selected from the group listed in Table 6.

Representative compounds of the present invention are as listed in Table 1 to 6 below. Unless otherwise noted, the compounds were prepared as mixtures of stereo-configuration (where applicable). In Tables 1, 2, 3 and 4, wherein a structure is drawn for the

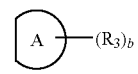

group, the symbol "∿∿" is used to denote the position of bridging atoms. In Tables 4 and 6, the " ==== " symbol is used to denote the presence of an optional double bond (i.e. used to denote optional unsaturation of the designated bond).

TABLE 1

Compounds of Formula (I)

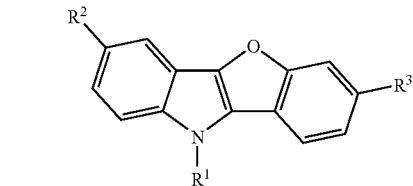

| ID No | $R^1$ | $R^2$ | $R^3$ |
|---|---|---|---|
| 1 | hydrogen | methoxy | benzyloxy |
| 2 | 4-(diethylamino-ethoxy)-benzyl- | methoxy | benzyloxy |
| 3 | 4-(diethylamino-ethoxy)-benzyl- | methoxy | hydroxy |

TABLE 2

Compound of Formula (II)

| ID No. | Z | Y | $R^1$ | $(R^2)_a$ | 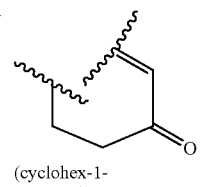 |
|---|---|---|---|---|---|
| 4 | —CH$_2$— | —CH$_2$— | methyl | 4-hydroxy | 2-thienyl |
| 5 | —CH2- | —CH$_2$— | methyl | 4-hydroxy | 2-(N-methyl-pyrrolyl) |
| 6 | —CH$_2$— | —CH$_2$— | methyl | 4-hydroxy | 2-pyridyl |
| 65 | —CH$_2$— | —CH$_2$— | methyl | 3-methoxy | (cyclohex-1-en-3-one) |
| 75 | —CH$_2$— | —CH$_2$— | methyl | 4-hydroxy | 2-thienyl |
| 76 | —CH$_2$— | —CH$_2$— | methyl | 4-hydroxy | 2-N-(methyl-pyrrolyl) |
| 80 | —CH$_2$— | —CH$_2$— | methyl | 4-hydroxy | 2-pyridyl |

TABLE 2-continued

Compound of Formula (II)

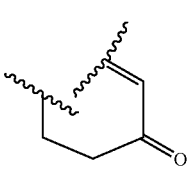

| ID No. | Z | Y | R¹ | (R²)ₐ | A—(R₃)ᵦ |
|---|---|---|---|---|---|
| 91 | —CH₂— | —CH₂— | methyl | 4-methoxy | (cyclohex-1-en-3-one) |
| 93 | —CH₂— | —CH₂— | methyl | 4-hydroxy | (cyclohex-1-en-3-one) |
| 104 | —CH₂— | —CH₂— | methyl | 4-methoxy | phenyl |
| 105 | —CH₂— | —CH₂— | methyl | 4-hydroxy | phenyl |
| 109 | —CH₂— | —CH₁— | methyl | 3-hydroxy | 2-pyridyl |
| 110 | —CH₂— | —CH₂— | methyl | 4-hydroxy | 4-pyridyl |
| 111 | —CH₂— | —CH₂— | methyl | 4-hydroxy | 2-pyrazinyl |
| 112 | —CH₂— | —CH₂— | dimethylamino-ethyl- | 4-hydroxy | 2-pyridyl |
| 113 | —CH₂— | —CH₂— | H | 4-methoxy | 2-(2-methyl-pyrazolyl) |
| 114 | —CH₂— | —CH₂— | methyl | 4-methoxy | 2-(2-methyl-pyrazolyl) |
| 116 | —CH₂— | —CH₂— | H | 4-methoxy | 2-(3-amino-pyrazinyl) |

TABLE 3

Compounds of Formula (II)

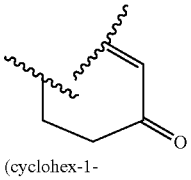

| ID No. | Z | Y | R¹ | (R²)ₐ | A—(R₃)ᵦ |
|---|---|---|---|---|---|
| 7 | —CH₂— | —S— | H | a = 0 | phenyl |
| 8 | —CH₂— | —S— | ethyl | 4-hydroxy | phenyl |
| 9 | —CH₂— | —S— | ethyl | 4-methyl-carbonyl-oxy- | phenyl |
| 10 | —CH₂— | —S— | ethyl | 4-methyl-sulfonyl-oxy- | phenyl |
| 11 | —CH₂— | —S— | methyl | 4-trifluoro-methyl-sulfonyl-oxy- | phenyl |
| 12 | —CH₂— | —S— | methyl | 4-chloro | phenyl |

TABLE 3-continued

Compounds of Formula (II)

| ID No. | Z | Y | R¹ | (R²)ₐ | A—(R₃)ᵦ |
|---|---|---|---|---|---|
| 13 | —CH₂— | —S— | methylcarbonyl- | 4-(t-butyl-dimethyl-silyloxy)- | phenyl |
| 14 | —CH₂— | —S— | methylcarbonyl- | 4-hydroxy | phenyl |
| 15 | —CH₂— | —S— | H | 4-chloro | phenyl |
| 16 | —CH₂— | —S— | H | 4-fluoro | phenyl |
| 17 | —CH₂— | —S— | methyl | 4-(t-butyl-carbonyl-oxy)- | phenyl |
| 18 | —CH₂— | —S— | methyl | 4-(t-butyl-dimethyl-silyloxy)- | phenyl |
| 19 | —CH₂— | —CO₂— | methyl | 4-(5-butyl-dimethyl-silyloxy)- | phenyl |
| 20 | —CH₂— | —S— | methyl | 4-(1,1,2,2,3,3,4,4,4-Nonafluorobutyl-sulfonyl-oxy)- | phenyl |
| 21 | —CH₂— | —S— | ethyl | 4-methoxy | phenyl |
| 22 | —CH₂— | —SO₂— | methyl | 4-methoxy | phenyl |
| 23 | —CH₂— | —SO₂— | methyl | 4-hydroxy | phenyl |
| 24 | —CH₂— | —S— | 4-(piperidinyl-ethoxy)-benzyl- | 4-hydroxy | phenyl |
| 25 | —CH₂— | —S— | 4-(diethylamino-ethoxy)-benzyl- | 4-(t-butyl-dimethyl-silyloxy)- | phenyl |
| 26 | —CH₂— | —S— | 4-(piperidinyl-ethoxy)-benzyl | 4-(t-butyl-dimethyl-silyloxy)- | phenyl |
| 27 | —CH₂— | —S— | H | 4-methoxy | phenyl |
| 28 | —CH₂— | —O— | H | 4-methoxy | phenyl |
| 29 | —CH₂— | —S— | methyl | 4-methoxy | phenyl |
| 30 | —CH₂— | —O— | methyl | 4-methoxy | phenyl |
| 32 | —CH₂— | —S— | H | 4-hdroxy | phenyl |
| 33 | —CH₂ | —S— | H | 4-(t-butyl-dimethyl-silyloxy)- | phenyl |
| 34 | —CH₂ | —S— | methyl | 4-hydroxy | phenyl |
| 35 | —CH₂ | —O— | methylcarbonyl- | 4-methoxy | phenyl |
| 38 | —CH₂— | —O— | H | 4-methoxy | 3-(benzyloxy)-phenyl |
| 39 | —CH₂— | —S— | 4-(diethylamino-ethoxy)-benzyl | 4-methoxy | phenyl |
| 40 | —CH₂— | —O— | 4-(diethylamino-ethoxy)-benzyl | 4-methoxy | phenyl |
| 41 | —CH₂— | —S— | hydroxy | 4-methoxy | phenyl |
| 42 | —CH₂— | —S— | methyl | 4-methyl | phenyl |
| 43 | —CH₂— | —S— | methyl | a = 0 | phenyl |
| 44 | —CH₂— | —S— | methyl | 4-fluoro | phenyl |
| 45 | —CH₂— | —S— | H | 4-methoxy | 3-(methoxy)-phenyl |
| 46 | —CH₂— | —S— | methyl | 4-methoxy | 3-(methoxy)-phenyl |
| 47 | —CH₂— | —S— | methyl | 4-methoxy | 3-(hydroxy)-phenyl |
| 48 | —CH₂— | —S— | methyl | 4-hydroxy | 3-(hydroxy)-phenyl |
| 49 | —CH₂— | —S— | H | 4-hydroxy | 3-(hydroxy)-phenyl |
| 50 | —CH₂— | —S— | 4-(diethylamino-ethoxy)-benzyl | 4-hydroxy | phenyl |
| 51 | —CH₂— | —SO— | methyl | 4-(t-butyl-dimethyl-silyloxy)- | phenyl |
| 52 | —CH₂— | —SO— | methyl | 4-hydroxy | phenyl |
| 53 | —CH(OH)— | —S— | methyl | 4-hydroxy | phenyl |
| 54 | —CH₂— | —SO— | methyl | 4-methoxy | phenyl |
| 55 | —CH₂— | —SO— | H | 4-methoxy | phenyl |
| 57 | —CH₂— | —S— | methyl | 4-bromo | phenyl |
| 59 | —CH₂— | —O— | 4-(methyl-carbonyloxy)-phenyl-carbonyl- | 4-methoxy | phenyl |

TABLE 3-continued

Compounds of Formula (II)

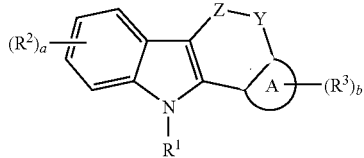

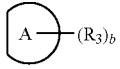

| ID No. | Z | Y | R¹ | (R²)ₐ | A—(R₃)ᵦ |
|---|---|---|---|---|---|
| 61 | —CH₂— | —S— | 4-(piperidinyl-ethoxy)-benzyl | 4-methoxy | phenyl |
| 63 | —CH(OH)— | —O— | methyl | 4-methoxy | phenyl |
| 66 | —CH₂— | —O— | H | 4-fluoro | phenyl |
| 67 | —CH₂— | —O— | H | 4-bromo | phenyl |
| 68 | —CH₂— | —O— | methyl | 4-fluoro | phenyl |
| 69 | —CH₂— | —O— | methyl | 4-bromo | phenyl |
| 70 | —C(CH₃)₂— | —O— | methyl | 4-hydroxy | 3-(hydroxy)-phenyl |
| 72 | —CH₂— | —S— | methyl | 4-hydroxy | 3-(carboxy)-phenyl |
| 73 | —CH₂— | —O— | methyl | a = 0 | phenyl |
| 74 | —CH₂— | —O— | methyl | 4-carboxy | phenyl |
| 77 | —CH₂— | —S— | methyl | 4-cyano | phenyl |
| 78 | —CH₂— | —S— | methyl | 4-hydroxy | 4-(bromo)-phenyl |
| 79 | —CH₂— | —S— | methyl | 4-hydroxy | phenyl |
| 81 | —CH₂— | —S— | methyl | 4-methoxy | 2-pyridyl |
| 82 | —CH₂— | —S— | methyl | 4-hydroxy | 2-pyridyl |
| 83 | —CH₂— | —S— | methyl | 2-hydroxy | 3-(fluoro)-phenyl |
| 84 | —CH₂— | —S— | methyl | 4-hydroxy | 3-(bromo)-phenyl |
| 85 | —CH₂— | —S— | methyl | 4-hydroxy | 3-(fluoro)-phenyl |
| 86 | —CH₂— | —S— | methyl | 4-hydroxy | 3-(trifluoro-methyl)-phenyl |
| 87 | —CH₂— | —S— | 4-(diethylamino-ethoxy)-benzyl | 4-(t-butyl-carbonyl-oxy)- | phenyl |
| 88 | —CH₂— | —S— | dimethylamino-ethyl- | 4-hydroxy | phenyl |
| 89 | —CH₂— | —S— | methyl | 4-fluoro | 3-(fluoro)-phenyl |
| 94 | —CH₂— | —S— | methyl | 4-methoxy-carbonyl | phenyl |
| 95 | —CH₂— | —S— | methyl | 4-carboxy | phenyl |
| 96 | —C(CH₃)₂— | —S— | H | 4-methoxy | 3-(methoxy)-phenyl |
| 97 | —C(CH₃)₂— | —S— | methyl | 4-methoxy | 3-(methoxy)-phenyl |
| 98 | —CH₂— | —S— | H | 4-(t-butyl-dimethyl-silyloxy)- | 3-(t-butyl-dimethyl-silyloxy)-phenyl |
| 99 | —CH₂— | —S— | H | 4-(t-butoxy-carbonyl-oxy)- | phenyl |
| 100 | —CH₂— | —S— | methyl | 3-hydroxy | phenyl |
| 101 | —CH₂— | —S— | H | 4-hydroxy | 2-pyridyl |
| 102 | —CH₂— | —S— | H | 4-methoxy | 2-pyridyl |
| 103 | —CH₂— | —S— | methyl | 4-methoxy | 2-(2-methyl-pyridyl) |
| 36 | —S | —CH₂— | methyl | 4-methoxy | phenyl |
| 37 | —S | —CH₂— | methyl | 4-hydroxy | phenyl |
| 62 | —S— | —CH₂— | 4-(piperidinyl-ethoxy)-phenyl-carbonyl- | 4-methoxy | phenyl |

TABLE 4

Compounds of formula (II)

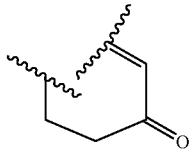

| ID NO | Z | Y | R⁶ | (R²)ₐ | A—(R³)ᵦ |
|---|---|---|---|---|---|
| 71 | —CH₂— | —CH₂— | methyl | 3-hydroxy | (cyclohex-1-en-3-one) |
| 106 | —CH₂— | —CH= | methyl | 4-methoxy | (3-(3-methyl-pieridin-4-one)) |
| 134 | —CH₂— | —CH= | methyl | 4-hydroxy | (3-(3-methyl-pieridin-4-one)) |

For compound #71, ----- represents a single bond; for compounds #106 and #134, ----- represents a double bond; as indicated by the designation of the Y substituent group in the table above.

TABLE 5

Compounds of Formula (II)

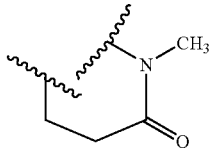

| ID No | R¹ | Y | (R²)ₐ | (R³)ᵦ |
|---|---|---|---|---|
| 136 | H | —NH— | 4-methoxy | b = 0 |
| 137 | H | —N(CH₃)— | 4-methoxy | 9-methoxy |
| 138 | methyl | —N(CH₃)— | 4-methoxy | b = 0 |
| 139 | methyl | —N(CH₃)— | 4-hydroxy | 10-hydroxy |
| 140 | methyl | —N(CH₃)— | 4-hydroxy | 10-methoxy |
| 141 | methyl | —N(CH₃)— | 4-hydroxy | b = 0 |

TABLE 6

Compounds of formula (II)

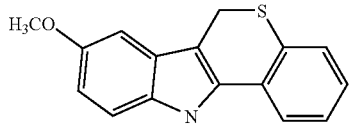

| ID No | Y | ==== | R¹ | (R²)$_a$ | A—(R₃)$_b$ |
|---|---|---|---|---|---|
| 126 | —CH₂— | single | methyl | 4-hydroxy | phenyl |
| 127 | —CH₂— | single | H | 4-methoxy | phenyl |
| 128 | —CH₂— | single | methyl | 4-methoxy | phenyl |
| 120 | —S— | double | H | 4-methoxy | phenyl |
| 117 | —S— | single | H | 4-methoxy | phenyl |
| 118 | —S— | single | methyl | 4-hydroxy | 3-(hydroxy)-phenyl |
| 119 | —S— | single | 4-(piperidinyl-ethoxy)-benzyl | 4-hydroxy | phenyl |
| 121 | —S— | single | 4-(piperidinyl-ethoxy)-benzyl | 4-methoxy | phenyl |
| 123 | —S— | single | methyl | 4-methoxy | phenyl |
| 124 | —S— | single | methyl | 4-hydroxy | phenyl |
| 125 | —S— | single | methyl | 4-hydroxy | 3-(methoxy)-phenyl |
| 129 | —S— | single | 4-(pyrrolidinyl-ethoxy)-benzyl | 4-methoxy | phenyl |
| 130 | —SO— | single | H | 4-methoxy | phenyl |

Additional representative intermediates or by-products in the preparation of the compounds of formula (I) and/or compounds of formula (II) are as listed in Table 7.

TABLE 7

Representative Intermediates and/or By-Products

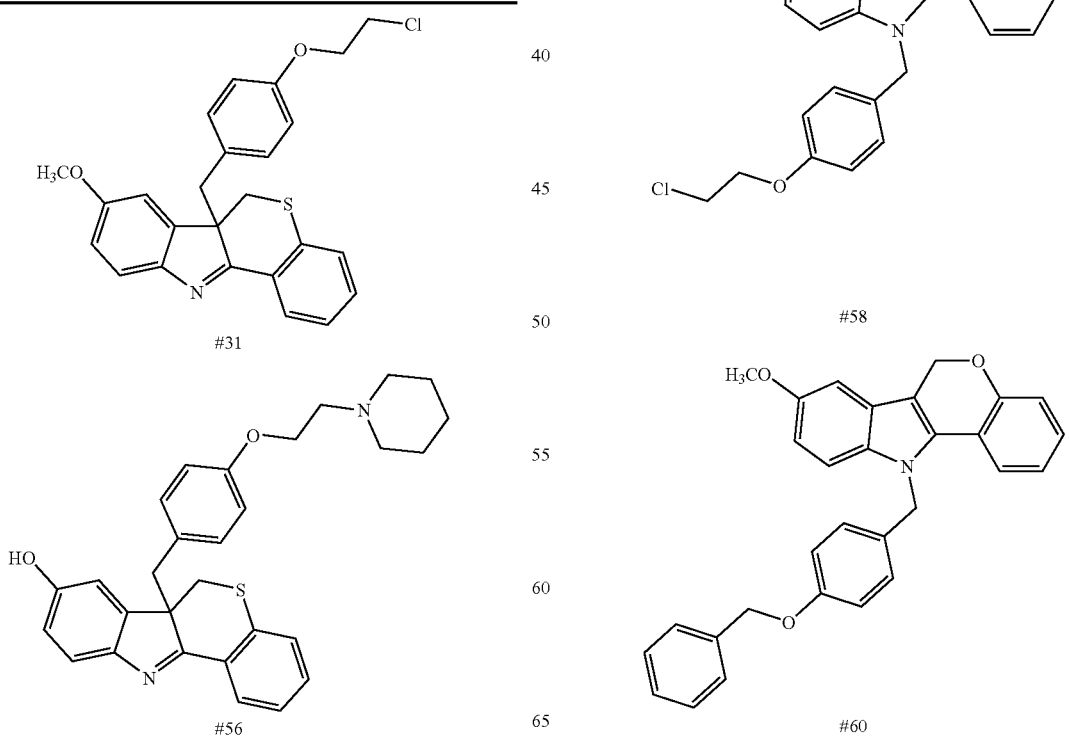

31

56

TABLE 7-continued

Representative Intermediates and/or By-Products

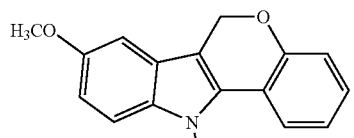

58

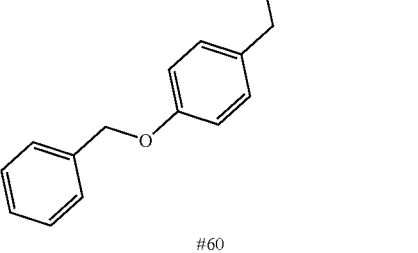

60

TABLE 7-continued

Representative Intermediates and/or By-Products

122

131

133

142

As used herein, the term "degenerative brain disease" shall include cognitive disorder, dementia, regardless of underlying cause, Alzheimer's disease, and the like.

As used herein, the term "cardiovascular disease" shall include elevated blood lipid levels, coronary arthrosclerosis, coronary heart disease, and the like.

As used herein, the term "cerebrovascular disease" shall include abnormal regional cerebral blood flow, ischemic brain damage, and the like.

As used herein, the term "progestogen antagonist" shall include mifepristone (RU-486), J-867 (Jenapharm/TAP Pharmaceuticals), J-956 (Jenapharm/TAP Pharmaceuticals), ORG-31710 (Organon), ORG-32638 (Organon), ORG-31806 (Organon), onapristone (ZK98299) and PRA248 (Wyeth). Further, as used herein, the terms "progestin" and "progesterone" are used interchangeably.

Estrogen receptor modulators are useful in the treatment and/or prevention of disorders and diseases mediated by one or more estrogen receptor(s) including, but not limited to, as hot flashes, vaginal dryness, osteopenia, osteoporosis, hyperlipidemia, loss of cognitive function, degenerative brain diseases, cardiovascular diseases, cerebrovascular diseases, hormone sensitive cancers, hyperplasia (in tissues including breast, endometrium, and cervix in women and prostate in men), endometriosis, uterine fibroids and osteoarthritis. Estrogen receptor modulators are further useful as contraceptive agents either alone or in combination with a progestogen or progestogen antagonist.

Androgen receptor modulators are useful in the treatment and/or prevention of disorders and diseases mediated by one of more androgen receptor(s) including, but not limited to, prostate carcinoma, benign prostatic hyperplasia (BPH), hirsitutism, alopecia, anorexia nervosa, breast cancer, acne, AIDS and cachexia. Androgen receptor modulators are further useful as a male contraceptive and/or as a male performance enhancer Progestin receptor modulators are useful in the treatment and/or prevention of disorders and diseases modulated by the progestin receptor, including, but not limited to, endometriosis (preferably without associated with bone loss and/or hypoestrogenism), myoma (preferably without associated with bone loss and/or hypoestrogenism), dysfunctional bleeding. Progestin receptor modulators are further useful as contraceptives either alone or in combination with one or more estrogen receptor modulator(s). Progestin receptor modulators are further still useful as adjunct to estrogen in hormone replacement therapy in postmenopausal women, as well as in the treatment of tumors containing steroid receptors.

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, pentyl and the like. Similarly, the term "$C_{1-4}$alkyl" whether used alone or as part of a substituent group, include straight and branched chains containing 4 carbon atoms. For example, methyl, ethyl, n-propyl, isopropyl, n-butyl, isobutyl, sec-butyl and t-butyl.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CH_2$—$CF_3$, —$CF_2$—$CF_2$—$CF_2$—$CF_3$, and the like.

As used herein, unless otherwise noted, "alkoxy" whether used alone or as part of a substituent group, shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{1-4}$alkoxy" whether used alone or as part of a substituent group, shall denote an oxygen ether radical of the above described straight or branched chain $C_{1-4}$alkyl groups. For example, methoxy, ethoxy, n-propoxy, sec-butoxy, t-butoxy, and the like.

As used herein, unless otherwise noted, "aryl" shall refer to unsubstituted carbocylic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, the term "partially unsaturated" when referring to a ring structure shall mean any stable ring structure which contains at east one unsaturated bond. Suitable examples include, but are not limited to cyclohexenyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include pyrrolyl, pyridyl, pyrazolyl, pyrazinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like. Preferred heterocycloalkyl groups include piperidinyl, morpholinyl, and the like.

As used herein, the notation "*" shall denote the presence of a stereogenic center.

When a particular group is "substituted" (e.g., aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula

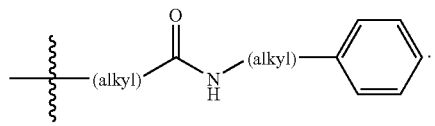

Unless otherwise noted, when naming $R^2$ and $R^3$ substituent groups on the compounds of formula (I) and formula (II), the following numbering of the attachment atoms will be applied:

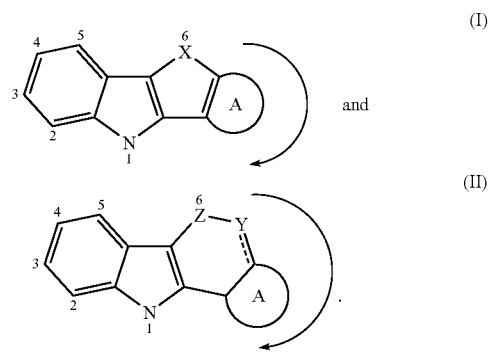

Unless otherwise noted, when naming the

ring, the first bridging carbon atom (counting clockwise as noted above) shall be denoted as in the 1-position with counting continued in a clockwise direction. Thus, for example, wherein the ring is denoted as 4-thienyl, the compound of formula (I) will have the following structure

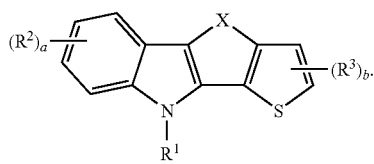

One skilled in the art will recognize that wherein the compound of formula (II) Y is —CH═ or —N═ then the ----symbol represent a double bond. Similarly, wherein the compound of formula (II) Y is other than —CH═ or —N═ then the ----symbol represent a single bond.

Abbreviations used in the specification, particularly the Schemes and Examples, are as follows:
18-Crown-6=1,4,7,10,13,16-hexaoxaxyxlooctadecane
BuLi or n-BuLi=n-Butyl lithium
DIPEA=Diethylisopropylamine
DMF=N,N-Dimethylformamide
DMSO=Dimethylsulfoxide
DTT=Dithiothreitol
EDTA=Ethylene diamine tetraacetic acid
ERT=Estrogen replacement therapy
Et=Ethyl (i.e —CH$_2$CH$_3$)
EtI=Ethyl Iodine
EtOAc=Ethyl acetate
EtOH=Ethanol
EtSH=Ethylthiol
HEPES=4-(2-Hydroxyethyl)-1-Piperizine Ethane Sulfonic Acid
HPLC=High Pressure Liquid Chromatography
HRT=Hormone replacement therapy
KO-t-Bu or t-Bu-OK=Potassium t-butoxide
Me=Methyl (i.e. —CH$_3$)
MeI=Methyl Iodide
MeOH=Methanol
NaBH$_4$=Sodium borohydride
NaOAc=Sodium Acetate
OXONE=Potassium monopersulfate triple salt
PBS=Phosphate buffered solution
Piv=Pivaloyl
PivCl=Pivaloyl Chloride
PPA=Polyphosphoric Acid
Py.HCl=Pyridine Hydrochloride
TBAF=Tetra(n-butyl)ammonium fluoride
TBS=Tert-butyl-dimethyl-silyl
TBSCl=Tert-butyl-dimethyl-silyl chloride
TEA or Et$_3$N=Triethylamine
Tf=Triflate (i.e. —O—SO$_2$—CF$_3$)
Tf$_2$O=Triflic anhydride
THF=Tetrahydrofuran
Tris HCl=Tris[hydroxymethyl]aminomethyl hydrochloride
TsOH=Tosic Acid The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

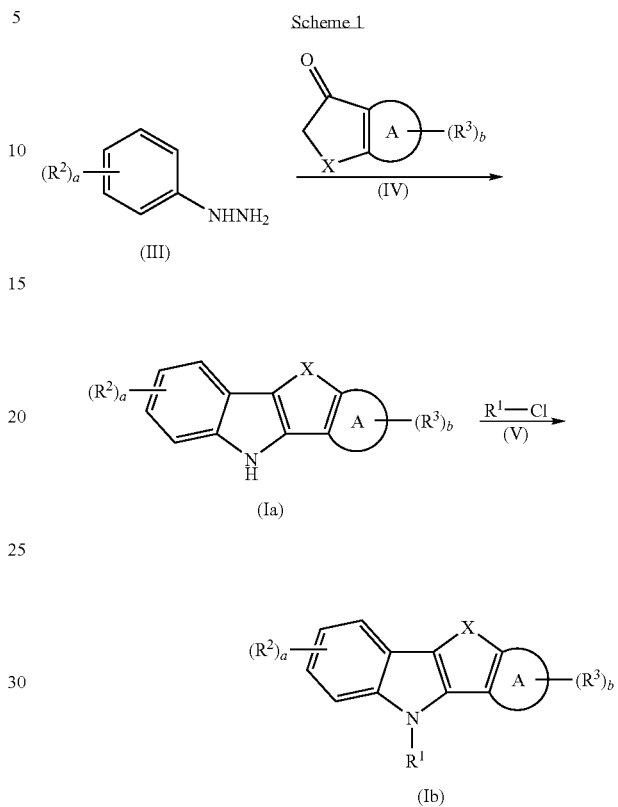

Accordingly, a suitably substituted compound of formula (III), a known compound or compound prepared by known methods is reacted with a suitably substituted compound of formula (IV), a known compound or compound prepared by known methods, in an organic solvent such as ethanol, methanol, isopropanol, t-butanol, and the like, at an elevated temperature in the range of from about 60° to about 150° C., preferably at about reflux temperature, to yield the corresponding compound of formula (Ia).

The compound of formula (Ia) is further, optionally, reacted with a suitably substituted compound of formula (V), a known compound or compound prepared by known methods, in the presence of a base such as NaH, NaHCO$_3$, Na$_2$CO$_3$, K$_2$CO$_3$, Na(C$_{1-4}$alkoxide) (such as sodium methoxide, sodium ethoxide, sodium t-butoxide, and the like), K(C$_{1-4}$ alkoxide) (such as potassium methoxide, potassium ethoxide, potassium t-butoxide, and the like), TEA, DIPEA, pyridine, and the like, in an organic solvent such as DMF, DMSO, THF, and the like, at a temperature in the range of from about 0° C. to about reflux, preferably at a temperature in the range of from about 0° C. to about room temperature, to yield the corresponding compound of formula (Ib).

One skilled in the art will recognize that wherein the compound of formula (I) X is —NR$^A$— and R$^A$ is other then hydrogen (for example, wherein R$^A$ is -L$^1$-R$^4$-(L$^2$)$_c$-R$^5$), the compound of formula (I) may be prepared from the corresponding compound of formula (I) wherein X is —NH— according to the process outlined in Scheme 2.

Scheme 2

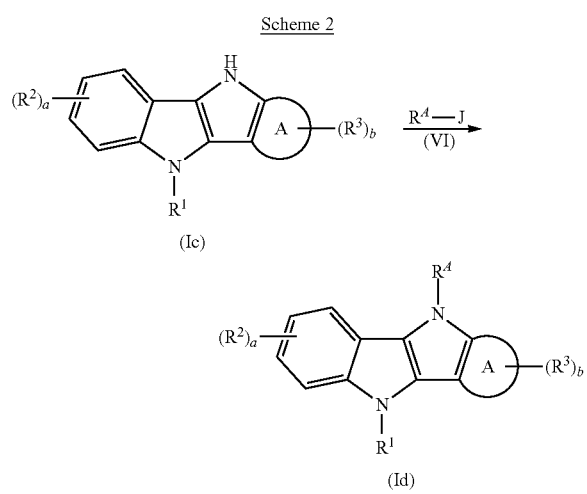

Accordingly, a suitably substituted compound of formula (Ic), is reacted with a suitably substituted compound of formula (VI), wherein J is a leaving group such as halogen, tosyl, mesyl, and the like, a known compound or compound prepared by known methods, in the presence of a base such as NaH, NaHCO$_3$, Na$_2$CO$_3$, K$_2$CO$_3$, Na(C$_{1-4}$alkoxide) (such as sodium methoxide, sodium ethoxide, sodium t-butoxide, and the like), K(C$_{1-4}$alkoxide) (such as potassium methoxide, potassium ethoxide, potassium t-butoxide, and the like), TEA, DIPEA, pyridine, and the like, in an organic solvent such as DMF, DMSO, THF, and the like, at a temperature in the range of from about 0° C. to about reflux, preferably at a temperature in the range of from about 0° C. to about room temperature, to yield the corresponding compound of formula (Id), wherein R$^A$ is other than hydrogen.

One skilled in the art will further recognize that wherein the compound of formula (I) one or more R$^2$ and/R$^3$ groups are OH, said hydroxy groups may be further functionalized to prepare compounds of formula (I) wherein one or more R$^2$ and/or R$^3$ groups are selected from —O-aralkyl, —C(O)—C$_{1-4}$alkyl, —C(O)O—C$_{1-4}$alkyl, —OC(O)—C$_{1-4}$alkyl, —O—SO$_2$—C$_{1-4}$alkyl or —O—SO$_2$-(halogenated C$_{1-4}$alkyl), according to known methods. For example, by reacting one or more of the OH substituent groups with a suitably substituted alkyl halide, acid chloride, sulfonyl chloride, and the like.

Compounds of formula (II) may be similarly prepared according to the process outlined in Scheme 1 above, by selecting and substituting a suitably substituted compound of formula (VII)

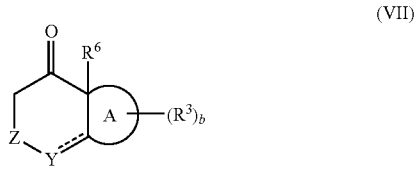

a known compound or compound prepared by known methods, for the compound of formula (II).

The present invention further comprises pharmaceutical compositions containing one or more compounds of formula (I) and/or compounds of formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more of the compounds of the present invention selected as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by one or more sex hormone receptor described in the present invention may also be carried out using a pharmaceutical composition comprising any of the compounds as defined herein and a pharmaceutically acceptable carrier. The pharmaceutical composition may contain between about 0.01 mg and 1000 mg, preferably about 1 to 500 mg, more preferably, 10 to 100 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by one or more sex hormone receptor is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

EXAMPLE 1

7-methoxy-thiochroman-4-one

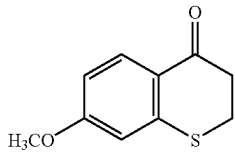

Following the procedure described in Speckamp, Willem N.; Westra, J. G.; Huisman, Henderikus O. *Tetrahedron* 1970, 26, 2353-63 the title compound was prepared as a colorless oil.

EXAMPLE 2

7-Methoxy-1-methyl-2,3-dihydro-1H-quinolin-4-one

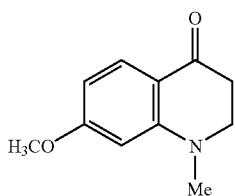

Following the procedure described in Speckamp, Willem N.; Van Velthuysen, J. A.; Pandit, U. K.; Huisman, H. O. *Tetrahedron* 1968, 24, 5881-91 the title compound was prepared as a yellow oil.

EXAMPLE 3

7-methoxy-2,2-dimethyl-thiochroman-4-one

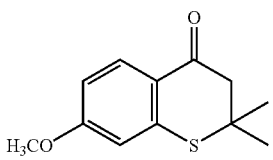

Following the procedure described in Camps, F.; Colomina, O.; Coll, J.; Messeguer, A. *Journal of Heterocyclic Chemistry* 1983, 20, 1115-17 the title compound was prepared as a colorless oil.

EXAMPLE 4

8-methoxy-6,11-dihydro-5-thia-11-aza-benzo[a]fluorene)

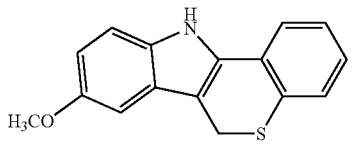

7-methoxy-thiochroman-4-one (700 mg, 4.27 mmol) was stirred with (4-methoxy-phenyl)-hydrazine (818 mg, 4.70 mmol, 1.1 eq.) in EtOH (40 mL, 0.1 M) and refluxed for 2 hours. EtOH was then removed from the mixture and EtOAc and saturated NaHCO$_3$ aqueous solution were added. The organic layer was separated, dried over K$_2$CO$_3$ and concentrated. The residue was purified with flash column chromatography (4:1 Hexane:EtOAc) to yield the title product as a brown solid.

MS (m/z): MH$^-$ (266)
$^1$H NMR (CDCl$_3$) δ 8.18 (broad s, 1H), 7.32-6.85 (m, 7H), 4.14 (s, 2H), 3.89 (s, 3H)

EXAMPLE 5

6,11-dihydro-5-thia-11-aza-benzo[a]fluorene

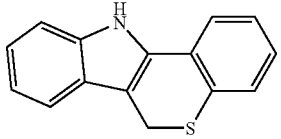

Following the procedure described in Example 4, using Isothiochroman-4-one (1.64 g, 10.0 mmol) as the starting material, the title compound was prepared as a brown solid.

$^1$H NMR (CDCl3) δ 8.25 (br. 1H), 7.55-7.10 (m, 8H), 4.20 (s, 2H)
Ms (m/z): MH$^+$ (236)

EXAMPLE 6

8-methoxy-5,11-dihydro-6-thia-11-aza-benzo[a]fluorene

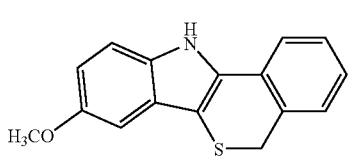

Following the procedure described in Example 4, isothiochroman-4-one (460 mg, 2.805 mmol) was used as the starting material to yield the title compound as a brown solid.
MS (m/z): MH+ (268), MH− (266)
$^1$H NMR (CDCl$_3$) δ 8.26 (broad s, 1H), 7.34-6.86 (m, 7H), 3.99 (s, 2H), 3.83 (s, 3H)

EXAMPLE 7

8-methoxy-6,11-dihydro-5-oxa-11-aza-benzo[a]fluorene

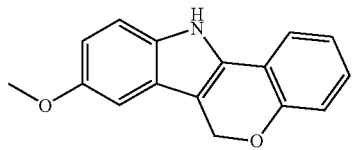

Following the procedure described in Example 4, using chroman-4-one (540 mg, 3.65 mmol) as the starting material, the title compound was prepared as a brown solid.
MS (m/z): MH+ (252), MH− (250)
$^1$H NMR (CDCl$_3$) δ 8.11 (broad s, 1H), 7.21-6.81 (m, 7H), 5.58 (s, 2H), 3.83 (s, 3H)

EXAMPLE 8

9-methoxy-6,7-dihydro-12H-5-thia-12-aza-dibenzo[a,e]azulene

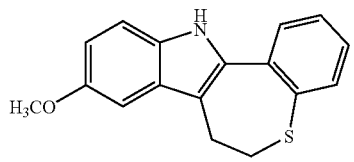

Following the procedure described in Example 4, using 3,4-dihydro-2H-benzo[b]thiepin-5-one (0.5 g, 2.8 mmol) as the starting material, the title compound was prepared as a brown solid.
MS (m/z): MH+ (282)
$^1$H NMR (CDCl$_3$) δ 7.94-6.86 (m, 7H), 3.88 (s, 3H), 3.39 (m, 2H, J=6.6 Hz), 3.21 (m, 2H, J=6.6 Hz)

EXAMPLE 9

8-fluoro-6,11,dihydro-5-thia-11-aza-benzo[a]fluorene

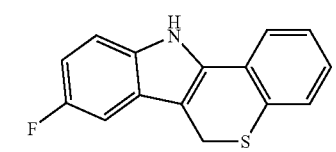

Following the procedure described in Example 4, using (4-fluoro-phenyl)-hydrazine (918 mg, 5.65 mmol) as the starting material, the title compound was prepared as a brown solid.

$^1$H NMR (CDCl$_3$) δ 8.15 (s, 1H), 7.28-6.82 (m, 7H), 4.18 (s, 2H)

EXAMPLE 10

8-methoxy-6,6-dimethyl-6,11-dihydro-5-thia-11-aza-benzo[a]fluorene

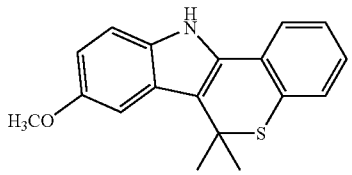

Following the procedure described in Example 4, using 7-methoxy-2,2-dimethyl-thiochroman-4-one (3.0 g, 13.5 mmol) as the starting material, the title compound was prepared as a brown solid.
MS (m/z): MH+ (326), MH− (324)
$^1$H NMR (CDCl$_3$) δ 8.02 (s, 1H), 7.29-6.63 (m, 6H), 3.88 (s, 3H), 3.78 (s, 3H), 1.82 (s, 6H)

EXAMPLE 11

8-chloro-6,11-dihydro-5-thia-11-aza-benzo[a]fluorene

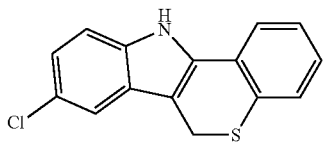

Following the procedure described in Example 4, using (4-chloro-phenyl)-hydrazine (872 mg, 4.871 mmol) as the starting material, the title compound was prepared as a brown solid.
MS (m/z): MH− (270)
$^1$H NMR (CDCl$_3$) δ 8.25 (s, 1H), 7.42-7.08 (m, 7H), 4.16 (s, 2H)

EXAMPLE 12

8-bromo-6,11-dihydro-5-thia-aza-benzo[a]fluorene

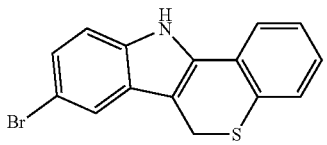

Following the procedure described in Example 4, using (4-bromo-phenyl)-hydrazine (3.2 g, 20.0 mmol) as the starting material, the title compound was prepared as a white solid.
$^1$H NMR (CDCl3) δ 8.55 (br. 1H), 7.60-7.15 (m, 7H), 4.18 (s, 2H)
Ms (m/z): MH+ (316)

EXAMPLE 13

3,8-dimethoxy-6,11-dihydro-5-thia-11-aza-benzo[a]fluorene

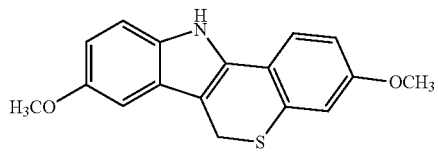

Following the same procedure in Example 4, using 7-methoxy-thiochroman-4-one (1.25 g, 6.44 mmol) as the starting material, the title compound was prepared as a brown solid.
MS (m/z): MH+ (298), MH− (296)
1H NMR (CDCl$_3$) δ 8.05 (broad s, 1H), 7.26-6.69 (m, 6H), 4.18 (s, 2H), 3.81 (s, 3H), 3.76 (s, 3H)

EXAMPLE 14

2-bromo-8-methoxy-6,11-dihydro-5-thia-11-aza-benzo[a]fluorene

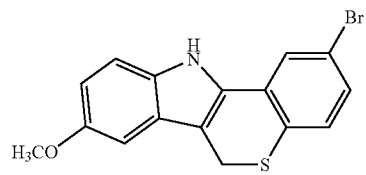

Following the procedure described in Example 4, using 6-bromo-thiochroman-4-one (0.6 g, 2.5 mmol) as the starting material, the title compound was prepared as a white solid.
1H NMR (CDCl3) δ 8.35 (br. 1H), 7.45-6.85 (m, 6H), 3.85 (s, 3H), 3.80 (s, 2H)
Ms (m/z): MH+ (346)

EXAMPLE 15

2-fluoro-8-methoxy-6,11-dihydro-5-thia-11-aza-benzo[a]fluorene

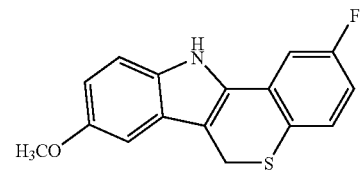

Following the procedure described in Example 4, using 6-fluoro-thiochroman-4-one (1.47 g, 0.8 mmol) as the starting material, the title compound was prepared as a white solid.
1H NMR (CDCl3) δ 8.28 (br. 1H), 7.35-6.85 (m, 6H), 4.15 (s, 2H), 3.85)
Ms (m/z): MH+ (284)

EXAMPLE 16

3-bromo-8-methoxy-6,11-dihydro-5-thia-11-aza-benzo[a]fluorene

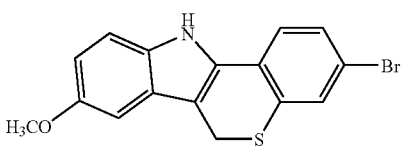

Following the procedure described in Example 4, using 6-bromo-isothiochroman-4-one (1.2 g, 5.0 mmol) as the starting material to yield the title compound as a brown solid.
1H NMR (CDCl3) δ 8.05 (br. 1H), 7.45-6.90 (m, 6H), 4.20 (s, 2H), 3.85 (s, 3H)
Ms (m/z): MH+ (345)

EXAMPLE 17

8-methoxy-3-trifluoromethyl-6,11-dihydro-5-thia-11-aza-benzo[a]fluorene

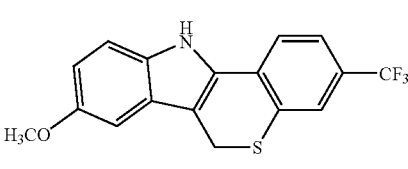

Following the procedure described in Example 4, using 6-trifluoromethyl-isothiochroman-4-one (1.15 g, 5.0 mmol), as the starting material to yield the title compound as a brown solid.
1H NMR (CDCl3) δ 8.25 (br. 1H), 7.55-6.90 (m, 6H), 4.15 (s, 2H), 3.85 (s, 3H)
Ms (m/z): MH+ (335)

EXAMPLE 18

3-fluro-8-methoxy-6,11-dihydro-5-thia-11-aza-benzo[a]fluorene

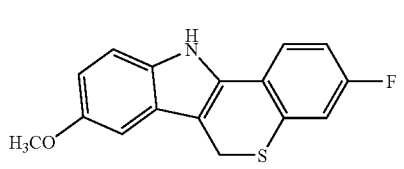

Following the procedure described in Example 4, using 6-fluoro-isothiochroman-4-one (900 mg, 5.0 mmol) as the starting material, the title compound was prepared as a brown solid.
1H NMR (CDCl3) δ 8.05 (br. 1H), 7.40-6.85 (m, 6H), 4.15 (s, 2H), 3.85 (s, 3H)
Ms (m/z): MH+ (284)

EXAMPLE 19

8-fluoro-6,11-dihydro-5-oxa-11-aza-benzo[a]fluorene

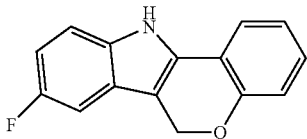

Following the procedure described in Example 4, using 4-fluoro-phenylhydrazine HCl salt (1.23 g, 7.57 mmoL) as the starting material, the title compound was prepared as a brown solid.

$^1$H NMR (CDCl$_3$) δ 8.20 (br, s, 1H), 7.65~6.80 (m, 7H), 5.38 (s, 2H).

MS (m/z): MH+, 240.

EXAMPLE 20

8-bromo-6,11-dihydro-5-oxa-11-aza-benzo[a]fluorene

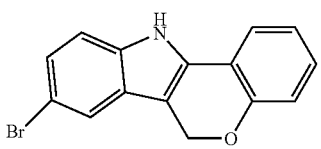

Following the procedure described in Example 4, using chroman-4-one (3.21 g, 21.7 mmoL) and 4-bromo-phenylhydrazine HCl salt (5.33 g, 23.8 mmoL) as the starting material, the title compound was prepared as a brown solid.

$^1$H NMR (CDCl$_3$) δ 8.18 (br, s, 1H), 7.70~6.75 (m, 7H), 5.40 (s, 2H).

MS (m/z): MH+, 300.

EXAMPLE 21

3,8-difluoro-6,11-dihydro-5-thia-11-aza-benzo[a]fluorene

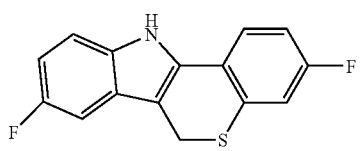

Following the procedure described in Example 4, using 6-fluoro-isothiochroman-4-one (900 mg, 5.0 mmoL) as the starting material, the title compound was prepared as a brown solid.

1H NMR (CDCl3) δ 8.00 (br. 1H), 7.55-6.95 (m, 6H), 4.00 (s, 2H)

Ms (m/z): MH+ (273)

EXAMPLE 22

8-benzyloxy-6,11-dihydro-5-oxa-11-aza-benzo[a]fluorene

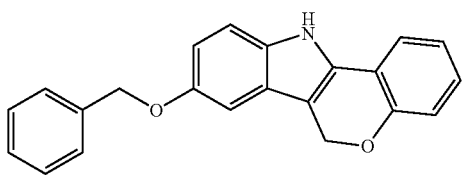

Following the procedure described in Example 4, using (4-benzyloxy-phenyl)-hydrazine hydrochloride salt and Chroman-4-one (2.93 g, 16.84 mmol) as the starting material, the title compound was prepared as a brown solid.

MS (m/z): MH+ (358)

$^1$H NMR (CDCl$_3$) δ 8.05 (broad s, 1H), 7.42-6.58 (m, 11H), 5.54 (s, 2H), 5.05 (s, 2H), 3.86 (s, 3H).

EXAMPLE 23

8-Methoxy-5,11-dihydro-6H-benzo[a]carbazole

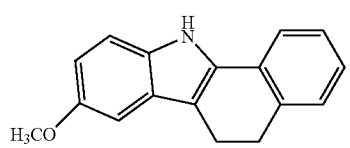

Following the procedure described in Example 4, using 3,4-dihydro-2H-naphthalen-1-one (2.90 g, 20 mmoL) and 4-methoxy-phenylhydrazine HCl salt as the starting material, the title compound was prepared as a brown solid.

$^1$H NMR (CDCl$_3$) δ 8.30 (br, s, 1H), 8.05~6.80 (m, 7H), 3.90 (s, 3H), 3.08 (t, J=10.5 Hz, 2H), 2.75 (t, J=10.5 Hz, 2H).

MS (m/z): MH+, 250.

EXAMPLE 24

9-methoxy-5,6,7,12-tetrahydro-benzo[6,7]cyclohepta[1,2b]indole

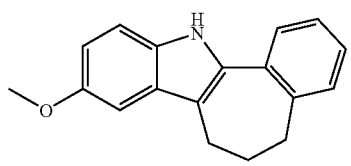

Following the procedure described in Example 4, using 6,7,8,9-tetrahydro-benzocyclohepten-5-one (1.10 g, 6.87 mmoL) and 4-methoxy-phenylhydrazine HCl salt (1.20 g, 6.87 mmoL) as the starting material, the title compound was prepared as a brown solid.

$^1$H NMR (CDCl$_3$) δ 8.20 (br, s, 1H) 7.40~6.80 (m, 7H) 3.95 (s, 3H), 2.75 (m, J=9.5 Hz, 4H), 2.35 (m, J=9.5 Hz, 2H).

MS (m/z): MH+, 264.

EXAMPLE 25

8-fluoro-6,11-dihydro-5-oxa-11-aza-benzo[a]fluorene

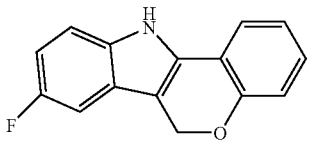

Following the procedure described in Example 4, using (4-fluoro-phenyl)-hydrazine hydrochloride salt and chroman-4-one (2.5 g, 17 mmol) as the starting material, the title compound was prepared as a brown solid.

MS (m/z): MH$^+$ (240)

EXAMPLE 26

8-bromo-6,11-dihydro-5-oxa-11-aza-benzo[a]fluorene

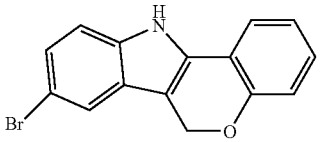

Following the procedure described in Example 4, using (4-bromo-phenyl)-hydrazine hydrochloride salt and chroman-4-one (3.0 g, 20 mmol) as the starting material, the title compound was prepared as a brown solid.

MS (m/z): MH$^+$ (301)

EXAMPLE 27

3-Methoxy-10H-benzo[4,5]furo[3,2-b]indole

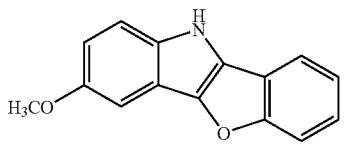

Following the procedure described in Example 4, using benzofuran-3-one (3.0 g, 30 mmol) as the starting material, the title compound was prepared as a brown solid.

MS (m/z): MH$^+$ (238)

EXAMPLE 28

7-Benzyloxy-3-methoxy-10H-benzo[4,5]furo[3,2-b]indole

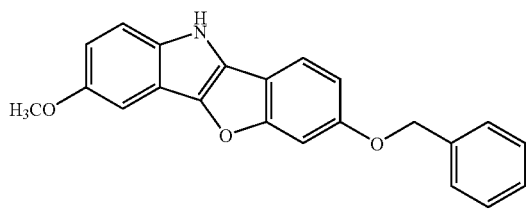

Following the procedure described in Example 4, using 6-benzyloxy-benzofuran-3-one (2.7 g, 11.2 mmol) as the starting material, the title compound was prepared as a brown solid.

MS (m/z): MH$^+$ (344)

EXAMPLE 29

8-methoxy-5,11-dihydro-6H-indolo[3,2-c]quinoline

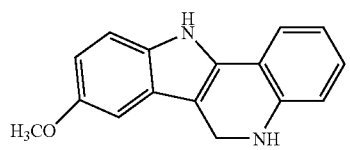

Following the procedure described in Example 4, using 2,3-dihydro-1H-quinolin-4-one (500 mg, 3.4 mmol) as the starting material, the title compound was prepared as a brown solid.

$^1$H NMR (CDCl$_3$) δ 7.85-6.60 (m, 7H), 4.50 (br. 1H), 3.70 (s, 2H), 3.20 (s, 3H)

MS (m/z): MH$^+$ (251)

EXAMPLE 30

3-Fluoro-10-methoxy-6,11-dihydro-5-thia-11-aza-benzo[a]fluorine

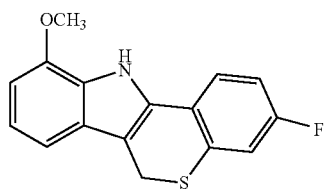

Following the procedure described in Example 4, starting with 6-fluoro-isothiochroman-4-one (900 mg, 5.0 mmol), the title compound was prepared as a brown solid.

1H NMR (CDCl3) δ 8.75 (br. 1H), 7.45-6.85 (m, 6H), 4.15 (s, 2H), 3.85 (s, 3H)

Ms (m/z): MH+ (284)

EXAMPLE 31

9-methoxy-6,11,dihydro-5-thia-11-aza-benzo[a]fluorene

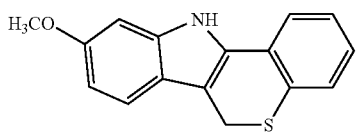

Following the procedure described in Example 4, starting with isothiochroman-4-one (1.64 g, 10.0 mmol), the title compound was prepare as a brown solid.
1H NMR (CDCl3) δ 8.35 (br. 1H), 7.45-6.85 (m, 7H), 3.85 (s, 3H), 3.80)
Ms (m/z): MH+ (267)

EXAMPLE 32

2,8-Dimethoxy-5-methyl-5,11-dihydro-6H-indolo[3,2-c]quinoline

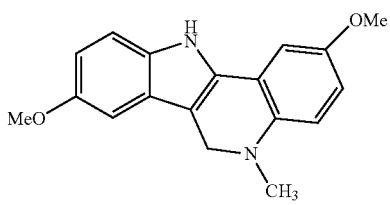

Following the procedure described in Example 19, using 7-methoxy-1-methyl-2,3-dihydro-1H-quinolin-4-one (3.5 g, 18.3 mmol) as the starting material, the title compound was prepared as a white solid.
MS (m/z): MH+ (295)

EXAMPLE 33

3,8-dimethoxy-11-methyl-6,11-dihydro-5-thia-11-aza-benzo[a]fluorene

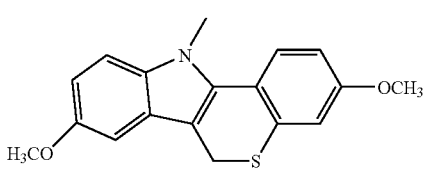

CH$_3$I (108 mg, 0.758 mmol, 1.5 eq.) was added to a mixture of 3,8-dimethoxy-6,11-dihydro-5-thia-11-aza-benzo[a]fluorene (150 mg, 0.505 mmol) and NaH (61 mg, 60% in mineral oil, 1.515 mmol, 3.0 eq.) in DMF. The reaction mixture was then stirred at 25° C. for 2 hours. The reaction mixture was partitioned between EtOAc and saturated NaHCO$_3$ aqueous solution. The aqueous layer was extracted three times with EtOAc. The combined organic layer was washed with brine, dried over anhydrous Na$_2$SO$_4$, filtered and concentrated to yield a crude material. The crude material was purified by silica gel (Hexanes to EtOAc 4:1) to yield the title compound as a brown solid.

MS (m/z): MH+ (312)
$^1$H NMR (CDCl$_3$) δ 7.51~6.78 (m, 6H), 4.05 (s, 2H), 3.87 (s, 3H), 3.85 (s, 3H), 3.78 (s, 3H)

EXAMPLE 34

3,8-dimethoxy-6,6,11-trimethyl-6,11-dihydro-5-thia-11-aza-benzo[a]fluorene

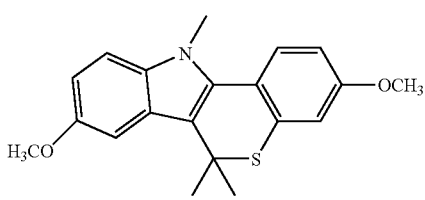

Following the procedure described in Example 33, starting with 8-methoxy-6,6-dimethyl-6,11-dihydro-5-thia-11-aza-benzo[a]fluorene (1.25 g, 3.84 mmoL), the title compound was prepared as a brown solid.
$^1$H NMR (CDCl$_3$) δ 8.01~6.65 (m, 6H), 3.90 (s, 3H), 3.85 (s, 3H), 3.62 (s, 3H), 1.80 (s, 6H).
MS (m/z): MH+, 340

EXAMPLE 35

8-methoxy-11-methyl-6,11-dihydro-5-oxa-11-aza-benzo[a]fluorene

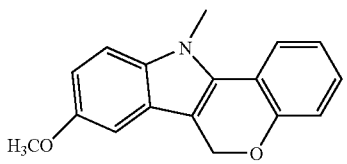

Following the procedure described in Example 33, using 8-methoxy-6,11-dihydro-5-oxa-11-aza-benzo[a]fluorene (250 mg, 0.996 mmol) as the starting material, the title compound was prepared as a white solid.
MS (m/z): MH+ (266)
$^1$H NMR (CDCl$_3$) δ 7.58-6.88 (m, 7H), 5.44 (s, 2H), 3.93 (s, 3H), 3.83 (s, 3H)

EXAMPLE 36

11-methyl-6,11-dihydro-5-thia-11-aza-benzo[a]fluorene

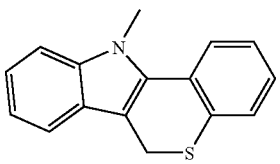

Following the procedure described in Example 33, using 6,11-dihydro-5-thia-11-aza-benzo[a]fluorene (236 mg) as the starting material, the title compound was prepared as a white solid.

¹H NMR (CDCl₃) δ 7.50-7.15 (m, 8H), 4.08 (s, 2H), 3.92 (t, 3H)
MS (m/z): MH⁺ (250)

EXAMPLE 37

8,11-diethyl-6,11-dihydro-5-thia-11-aza-benzo[a]fluorene

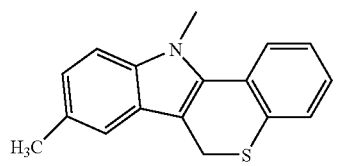

Following the procedure described in Example 33, using 6,11-dihydro-5-thia-11-aza-benzo[a]fluorene (250 mg) as a starting material, the title compound was prepared as a white solid.
¹H NMR (CDCl₃) δ 7.62-7.10 (m, 7H), 4.08 (s, 2H), 3.92 (t, 3H), 2.46)
MS (m/z): MH⁺ (266)

EXAMPLE 38

8-Chloro-11-methyl-6,11-dihydro-5-thia-11-aza-benzo[a]fluorene

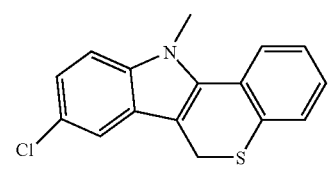

Following the procedure described in Example 33, using 8-chloro-6,11-dihydro-5-thia-11-aza-benzo[a]fluorene (540 mg, 1.99 mmol) as the starting material, the title compound was prepared as a white solid.
¹H NMR (CDCl₃) δ 7.56-7.08 (m, 7H), 4.05 (s, 2H), 3.84 (s, 3H)

EXAMPLE 39

8-bromo-11-methyl-6,11-dihydro-5-thia-11-aza-benzo[a]fluorene

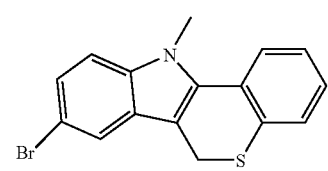

Following the procedure as described in Example 33, using 8-bromo-6,11-dihydro-5-thia-aza-benzo[a]fluorene (600 mg) as the starting material, the title compound was prepared as a white solid.

¹H NMR (CDCl₃) δ 7.65-7.15 (m, 7H), 4.00 (s, 2H), 3.92 (t, 3H)
MS (m/z): MH+ (330)

EXAMPLE 40

8-fluoro-11-methyl-6,11-dihydro-5-oxa-11-aza-benzo[a]fluorene

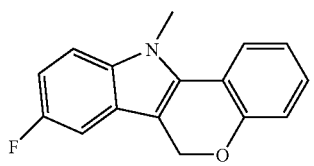

Following the procedure as described in Example 33, using 8-fluoro-6,11-dihydro-5-oxa-11-aza-benzo[a]fluorene (1.02 g, 4.27 mmoL) as the starting material, the title compound was prepared as a white solid.
¹H NMR (CDCl₃) δ 7.62~6.95 (m, 7H), 5.40 (s, 2H), 3.95 (s, 3H).
MS (m/z): MH+, 254.

EXAMPLE 41

8-bromo-11-methyl-6,11-dihydro-5-oxa-11-aza-benzo[a]fluorene)

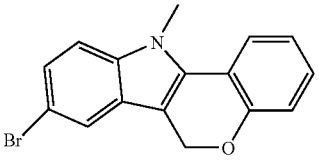

Following the procedure as described in Example 33, using 8-bromo-6,11-dihydro-5-oxa-11-aza-benzo[a]fluorene (1.05 g, 3.50 mmoL) as the starting material, the title compound was prepared as a white solid.
¹H NMR (CDCl₃) δ 7.62~6.95 (m, &H), 5.38 (s, 2H), 3.95 (s, 3H).
MS (m/z): MH+, 314.

EXAMPLE 42

3-Bromo-8-methoxy-11-methyl-6,11-dihydro-5-thia-11-aza-benzo[a]fluorene

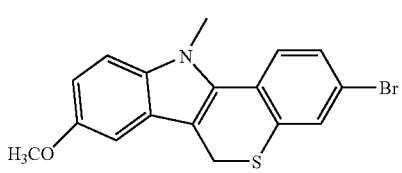

Following the procedure described in Example 33, using 3-bromo-8-methoxy-6,11-dihydro-5-thia-11-aza-benzo[a]fluorene (680 mg, 2.0 mmol) as the starting material, the title compound was prepared as a white solid.

¹H NMR (CDCl₃) δ 7.55-6.65 (m, 6H), 4.10 (s, 3H), 4.00 (s, 2H), 3.90 (s, 3H)
MS (m/z): MH+ (359)

EXAMPLE 43

8-methoxy-11-methyl-5,11-dihydro-6H-benzo[a]carbazole

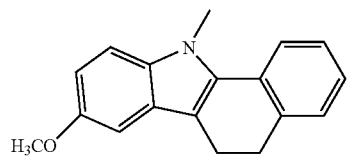

Following the procedure as described in Example 33, using 8-methoxy-5,11-dihydro-6H-benzo[a]carbazole (0.85 g, 3.41 mmoL) as the starting material, the title compound was prepared as a white solid.
¹H NMR (CDCl₃) δ 7.64~6.82 (m, 7H), 4.05 (s, 3H), 3.92 (s, 3H), 3.05 (t, J=11.5 Hz, 2H), 2.90 (t, J=11.5 Hz, 2H).
MS (m/z): MH+, 264.

EXAMPLE 44

9-methoxy-12-methyl-5,6,7,12-tetrahydro-benzo[6,7]cyclohepta[1,2-b]indole

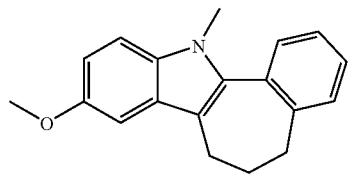

Following the procedure as described in Example 33, using 9-methoxy-5,6,7,12-tetrahydro-benzo[6,7]cyclohepta[1,2-b]indole (1.05 g, 3.99 mmoL) as the starting material, the title compound was prepared as a white solid.
¹H NMR (CDCl₃) δ 7.35~6.85 (m, 7H), 3.92 (s, 3H), 3.84 (s, 3H0, 2.68 (m, J=8.5 Hz, 4H), 2.28 (m, J=8.5 Hz, 2H).
MS (m/z): MH+, 278.

EXAMPLE 45

8-methoxy-11-methyl-3-trifluoromethyl-6,11-dihydro-5-thia-11-aza-benzo[a]fluorine

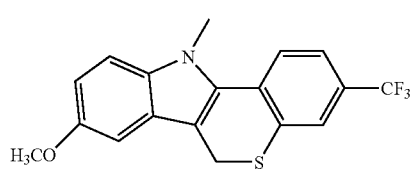

Following the procedure described in Example 33, using with 8-methoxy-3-trifluoromethyl-6,11-dihydro-5-thia-11-aza-benzo[a]fluorene (670 mg, 2.0 mmol) as the starting material, the title compound was prepared as a white solid.

¹H NMR (CDCl₃) δ 7.75-6.95 (m, 6H), 4.10 (s, 2H), 3.85 (s, 3H), 3.80 (s, 3H)
MS (m/z): MH+ (349).

EXAMPLE 46

9-methoxy-11-methyl-6,11-dihydro-5-thia-11-aza-benzo[a]fluorene

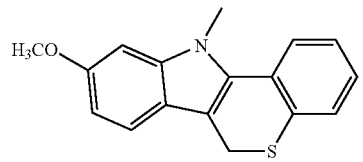

Following the procedure described in Example 33, using 9-methoxy-6,11,dihydro-5-thia-11-aza-benzo[a]fluorene (530 mg, 2.0 mmol) as the starting material, the title compound was prepared as a white solid.
¹H NMR (CDCl₃) δ 7.65-6.80 (m, 7H), 4.08 (s, 2H), 3.85 (s, 6H)
MS (m/z): MH+ (280)

EXAMPLE 47

3-Fluoro-10-methoxy-11-methyl-6,11-dihydro-5-thia-11-aza-benzo[a]fluorine

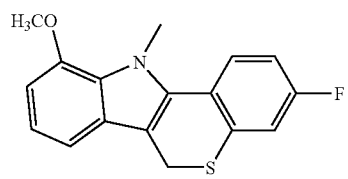

Following the procedure described in Example 33, using 3-Fluoro-10-methoxy-6,11-dihydro-5-thia-11-aza-benzo[a]fluorine (285 mg, 1.0 mmol) as the starting material, the title compound was prepared as a white solid.
¹H NMR (CDCl₃) δ 7.55-6.65 (m, 6H), 4.10 (s, 3H), 4.00 (s, 2H), 3.90 (s, 3H)
MS (m/z): MH+ (299)

EXAMPLE 48

3-fluoro-8-methoxy-11-methyl-6,11-dihydro-5-thia-11-aza-benzo[a]fluorine

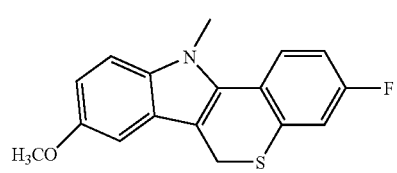

Following the procedure described in Example 33, using 3-fluoro-8-methoxy-6,11-dihydro-5-thia-11-aza-benzo[a]fluorene (285 mg, 1.0 mmol) as the starting material, the title compound was prepared as a white solid.

<sup>1</sup>H NMR (CDCl$_3$) δ 7.55-6.65 (m, 6H), 4.10 (s, 3H), 4.00 (s, 2H), 3.90 (s, 3H)
MS (m/z): MH+ (299)

EXAMPLE 49

3,8-difluoro-11-methyl-6,11-dihydro-5-thia-11-aza-benzo[a]fluorene

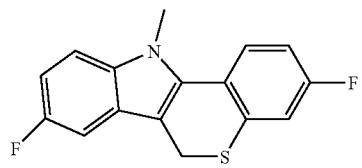

Following the procedure described in Example 33, using 3,8-difluoro-6,11-dihydro-5-thia-11-aza-benzo[a]fluorene (273 mg) as the starting material, the title compound was prepared as a white solid.
<sup>1</sup>H NMR (CDCl$_3$) δ 7.60-6.55 (m, 6H), 4.00 (s, 2H), 3.90 (s, 3H)
MS (m/z): MH+ (288)

EXAMPLE 50

8-fluoro-11-methyl-6,11-dihydro-5-thia-11-aza-benzo[a]fluorene

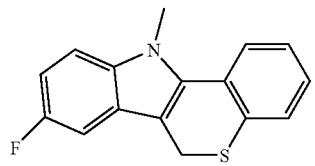

Following the procedure described in Example 33, using 8-fluoro-6,11-dihydro-5-thia-11-aza-benzo[a]fluorene (525 mg, 2.06 mmol) as the starting material, the title compound was prepared as a white solid.
MS (m/z): MH<sup>−</sup> (268)
<sup>1</sup>H NMR (CDCl$_3$) δ 7.58-6.83 (m, 7H), 3.98 (s, 2H), 3.87 (s, 3H)

EXAMPLE 51

8-fluoro-11-methyl-6,11-dihydro-5-oxa-11-aza-benzo[a]fluorene

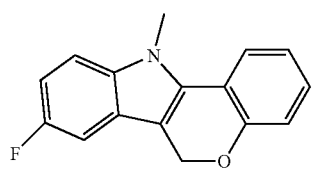

Following the procedure described in Example 33, using 8-fluoro-6,11-dihydro-5-oxa-11-aza-benzo[a]fluorene (1.02 g, 4.26 mmol) as the starting material, the title compound was prepared as a white solid.

<sup>1</sup>H NMR (CDCl$_3$) δ 7.58-6.83 (m, 7H), 5.41 (s, 2H), 3.96 (s, 3H)

EXAMPLE 52

8-methoxy-11-methyl-6,11-dihydro-5-oxa-11-aza-benzo[a]fluorene

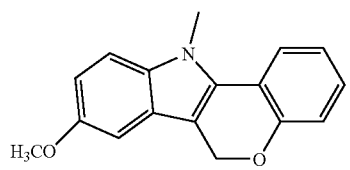

Following the procedure described in Example 33, using 8-methoxy-6,11-dihydro-5-oxa-11-aza-benzo[a]fluorene (9.3 g, 63 mmoL) as the starting material, the title compound was prepared as a white solid.
<sup>1</sup>H NMR (CDCl$_3$) δ 7.65~6.85 (m, 7H), 5.45 (s, 2H), 3.95 (s, 3H), 3.85 (s, 3H).
MS (m/z): MH+, 266.

EXAMPLE 53

8-bromo-11-methyl-6,110-dihydro-5-oxa-11-aza-benzo[a]fluorene

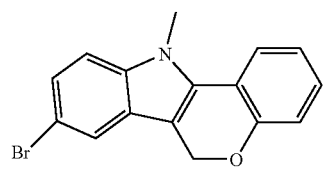

Following the procedure described in Example 33, using 8-bromo-6,11-dihydro-5-oxa-11-aza-benzo[a]fluorine (1.05 g, 3.50 mmol) as the starting material, the title compound was prepared as a white solid.
<sup>1</sup>H NMR (CDCl$_3$) δ 7.58-6.93 (m, 7H), 5.38 (s, 2H), 3.94 (s, 3H)

EXAMPLE 54

8-Methoxy-11-methyl-5,11-dihydro-6-thia-11-aza-benzo[a]fluorene

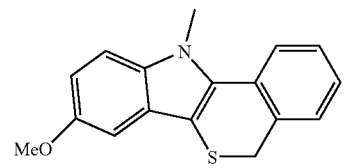

Following the procedure as described in Example 33, using 8-methoxy-6,11-dihydro-5-thia-11-aza-benzo[a]fluorine (240 mg, 0.899 mmol) as the starting material, the title compound was prepared as a white solid.
MS (m/z): MH+ (282)

¹H NMR (CDCl₃) δ7.53-6.88 (m, 7H), 3.96 (s, 3H), 3.88 (s, 2H), 3.85 (s, 3H)

EXAMPLE 55

11-ethyl-8-methoxy-6,11-dihydro-5-thia-11-aza-benzo[a]fluorene

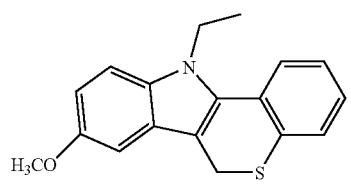

Following the procedure as in Example 33, using 8-methoxy-6,11-dihydro-5-thia-11-aza-benzo[a]fluorene (1.00 g, 3.75 mmol) and EtI (878 mg, 5.63 mmoL) as the starting material, the title compound was prepared as a white solid.
MS (m/z): MH⁻ (294)
¹H NMR (CDCl₃) δ 7.42-6.78 (m, 7H), 4.18 (q, 2H, J=6.4 Hz), 3.92 (s, 2H), 3.78 (s, 3H), 1.34 (t, 3H, J=6.4 Hz)

EXAMPLE 56

8-methoxy-5,11-dimethyl-5,11-dihydro-6H-indolo[3,2-c]quinoline

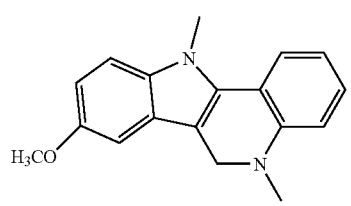

Following the procedure described in Example 33, using 8-methoxy-5,11-dihydro-6H-indolo[3,2-c]quinoline (500 mg, 2 mmol) as the starting material, the title compound was prepared as a white solid.
¹H NMR (CDCl₃) δ 8.0-6.70 (m, 7H), 3.75 (s, 3H), 3.13 (s, 2H), 3.00 (s, 3H)

EXAMPLE 57

2,8-Dimethoxy-5,11-dimethyl-5,11-dihydro-6H-indolo[3,2-c]quinoline

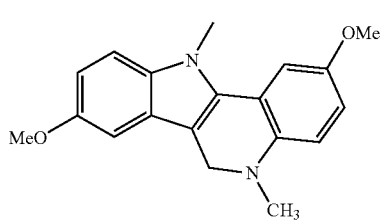

Following the procedure described in Example 33, using 2,8-Dimethoxy-5-methyl-5,11-dihydro-6H-indolo[3,2-c]quinoline (1.3 g, 4.42 mmol) as the starting material, the title compound was prepared as a white solid.
MS (m/z): MH⁺ (309)

EXAMPLE 58

6,11-dihydro-5-thia-11-aza-benzo[a]fluorene-3,8-diol

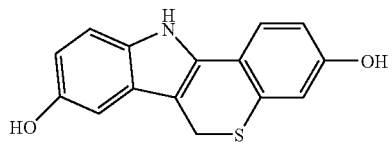

A mixture of 3,8-dimethoxy-6,11-dihydro-5-thia-11-aza-benzo[a]fluorene (805 mg, 2.69 mmol) and Py.HCl (3.11 g, 26.9 mmol, 10 eq.) was heated to 210° C. for 30 minutes. The reaction mixture was then partitioned between EtOAc and saturated NaHCO₃ aqueous solution. The aqueous layer was extracted three times with EtOAc. The combined organic layer was washed with brine, dried over anhydrous Na₂SO₄, filtered and concentrated to yield a crude material. The crude material was purified by silica gel (EtOAc to CH₂Cl₂:MeOH 5:1) to yield the title compound as a brown solid.
MS (m/z): MH⁺ (270)

EXAMPLE 59

12-methyl-6,7-dihydro-12H-5-thia-12-aza-dibenzo[a,e]azulen-9-ol

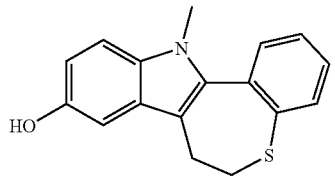

Following the procedure described in Example 58, using 9-methoxy-12-methyl-6,7-dihydro-12H-5-thia-12-aza-dibenzo[a,e]azulene (495 mg, 1.0 mmol) as the starting material, the title compound was prepared as a white solid.
MS (m/z): MH⁺ (282), MH⁻ (280)
¹H NMR (CDCl₃) δ 7.89 (br s, 1H), 7.68-6.75 (m, 7H), 3.38 (t, 2H, J=6.6 Hz), 3.18 (t, 2H, J=6.6 Hz), 1.61 (br s, 3H)

EXAMPLE 60

11-methyl-6,11-dihydro-5-thia-11-aza-benzo[a]fluorene-3,8-diol and 8-methoxy-11-methyl-6,11-dihydro-5-thia-11-aza-benzo[a]fluoren-3-ol

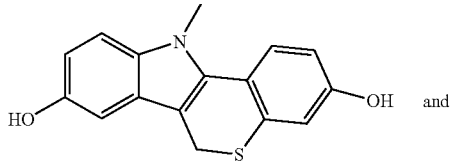 and

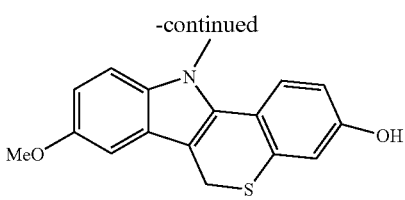

Following the procedure in Example 58, starting from 3,8-dimethoxy-11-methyl-6,11-dihydro-5-thia-11-aza-benzo[a]fluorene (95 mg, 0.304 mmol), 11-methyl-6,11-dihydro-5-thia-11-aza-benzo[a]fluorene-3,8-diol was prepared as a brown solid and 8-methoxy-11-methyl-6,11-dihydro-5-thia-11-aza-benzo[a]fluoren-3-ol was prepared as a white solid respectively.

8-methoxy-11-methyl-6,11-dihydro-5-thia-11-aza-benzo[a]fluoren-3-ol

MS (m/z): MH$^+$ (298), MH$^-$ (296)
$^1$H NMR (CDCl$_3$) δ 7.52~6.78 (m, 6H), 4.04 (s, 2H), 3.92 (s, 3H), 3.84 (s, 3H).

11-methyl-6,11-dihydro-5-thia-11-aza-benzo[a]fluorene-3,8-diol

MS (m/z): MH$^+$ (284)

EXAMPLE 61

5,11-dimethyl-5,11-dihydro-6H-indolo[3,2-c]quinoline-2,8-diol and 2-methoxy-5,11-dimethyl-5,11-dihydro-6H-indolo[3,2-c]quinolin-8-ol

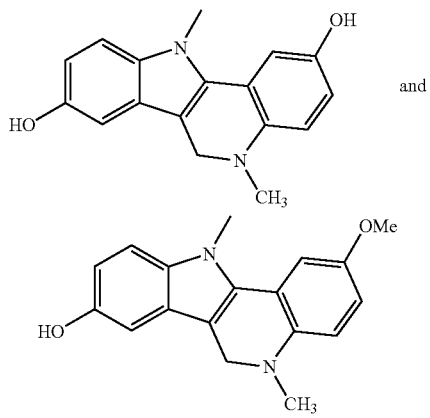

Following the procedure in Example 58, using 2,8-dimethoxy-5,11-dimethyl-5,11-dihydro-6H-indolo[3,2-c]quinoline (150 mg) as the starting material, 5,11-dimethyl-5,11-dihydro-6H-indolo[3,2-c]quinoline-2,8-diol as was obtained a brown solid and 2-methoxy-5,11-dimethyl-5,11-dihydro-6H-indolo[3,2-c]quinolin-8-ol was obtained as a white solid.

5,11-dimethyl-5,11-dihydro-6H-indolo[3,2-c]quinoline-2,8-diol

MS (m/z): MH$^+$ (299)

$^1$H NMR (CDCl$_3$) δ 7.19-6.72 (m, 6H), 3.58 (s, 3H), 3.36 (t, 2H, J=6.4 Hz), 2.89 (br s, 2H)

2-methoxy-5,11-dimethyl-5,11-dihydro-6H-indolo[3,2-c]quinolin-8-ol

MS (m/z): MH$^+$ (312)
$^1$H NMR (CDCl$_3$) δ 7.29-6.79 (m, 6H), 3.89 (s, 3H), 3.73 (s, 3H), 3.49 (t, 2H, J=6.8 Hz), 2.95 (br s, 2H)

EXAMPLE 62

11-methyl-6,11-dihydro-5-thia-11-aza-benzo[a]fluoren-8-ol

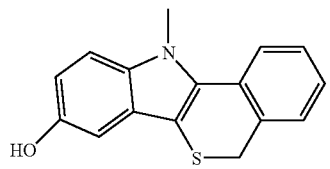

Following the procedure in Example 58, using 8-Methoxy-11-methyl-5,11-dihydro-6-thia-11-aza-benzo[a]fluorene (61 mg, 0.217 mmol) as the starting material, the title compound was prepared as a white solid.
MS (m/z): MH$^+$ (268)
$^1$H NMR (CDCl$_3$) δ 7.48-6.85 (m, 7H), 4.71 (s, 1H), 3.93 (s, 3H), 3.83 (s, 2H)

EXAMPLE 63

11-methyl-6,11-dihydro-5-thia-aza-benzo[a]fluoren-8-ol

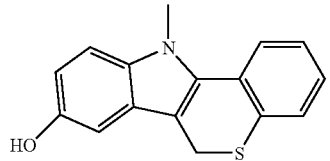

Following the procedure in Example 58, using 8-methoxy-11-methyl-6,11-dihydro-5-thia-11-aza-benzo[a]fluorene (75 mg, 0.268 mmol) as the starting material, the title compound was prepared as a white solid.
$^1$H NMR (CDCl$_3$) δ 7.32-6.85 (m, 7H), 4.02 (s, 2H), 3.93 (s, 3H).

EXAMPLE 64

2-bromo-11-methyl-6,11-dihydro-5-thia-11-aza-benzo[a]fluoren-8-ol

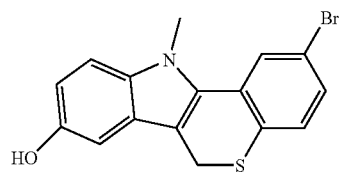

Following the procedure described in Example 33, using 2-bromo-8-methoxy-6,11-dihydro-5-thia-11-aza-benzo[a]fluorene (340 mg, 1.0 mmol), 2-bromo-8-methoxy-11-methyl-6,11-dihydro-5-thia-11-aza-benzo[a]fluorine was prepared as a crude product. The crude product was further reacted according to the procedure as described in Example 58, to yield the title compound as a brown solid.

$^1$H NMR (CDCl$_3$) δ 7.72-6.85 (m, 6H), 4.00 (s, 2H), 3.90 (s, 3H)

MS (m/z): MH+ (344)

EXAMPLE 65

2-fluoro-11-methyl-6,11-dihydro-5-thia-11-aza-benzo[a]fluoren-8-ol

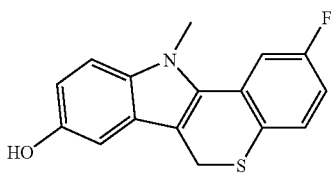

Following the procedure described in Example 33, starting from 2-fluoro-8-methoxy-6,11-dihydro-5-thia-11-aza-benzo[a]fluorene (700 mg, 2.30 mmol), 2-fluoro-8-methoxy-11-methyl-6,11-dihydro-5-thia-11-aza-benzo[a]fluorine was prepared as a crude product. The crude product was then further reacted according to the procedure described in Example 58, to yield the title compound as a brown solid.

$^1$H NMR (CDCl$_3$) δ 7.45-6.80 (m, 6H), 3.95 (s, 2H), 3.85 (s, 3H)

MS (m/z): MH+ (284)

EXAMPLE 66

11-methyl-5,11-dihydro-6H-benzo[a]carbazol-8-ol

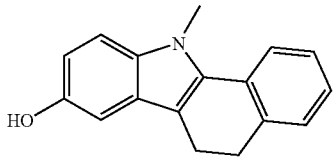

Following the procedure in Example 58, using 8-methoxy-11-methyl-5,11-dihydro-6H-benzo[a]carbazole (780 mg, 2.96 mmoL) as the starting material, the title compound was prepared as a white solid.

$^1$H NMR (CDCl$_3$) δ 7.62~6.78 (m, 7H), 4.80 (s, 3H), 3.95 (s, 3H), 2.95 (t, J=10.5 Hz, 2H), 2.80 (t, J=10.5 Hz, 2H).

MS (m/z): MH+, 250, MH−, 248.

EXAMPLE 67

12-Methyl-5,6,7,12-tetrahydro-benzo[6,7]cyclohepta[1,2-b]indol-9-ol

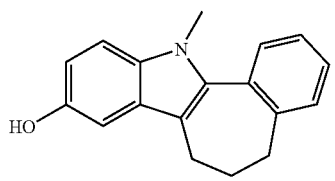

Following the procedure in Example 58, using 9-methoxy-12-methyl-5,6,7,12-tetrahydro-benzo[6,7]cyclohepta[1, 2-b]indole (896 mg, 3.23 mmoL) as the starting material, the title compound was prepared as a white solid.

$^1$H NMR (CDCl$_3$) δ 7.42~6.78 (m, 8H), 3.75 (s, 3H), 2.65 (t, J=10.5 Hz, 2H), 2.20 (m, J=10.5 Hz, 2H).

MS (m/z): MH+, 264.

EXAMPLE 68

6,6,11-trimethyl-6,11-dihydro-5-thia-11-aza-benzo[a]fluorene-3,8-diol

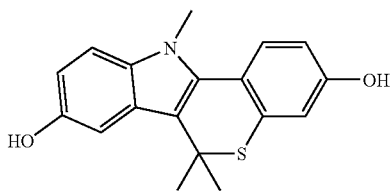

Following the procedure in Example 58, using 3,8-dimethoxy-6,6,11-trimethyl-6,11-dihydro-5-thia-11-aza-benzo[a]fluorene (720 mg, 2.12 mmoL) as the starting material, the title compound was prepared as a white solid.

$^1$H NMR (CDCl$_3$) δ 7.48~6.68 (m, 8H), 3.60 (s, 3H), 1.78 (s, 6H).

MS (m/z): MH+, 312, MH−, 310.

EXAMPLE 69

11-methyl-3-trifluoromethyl-6,11-dihydro-5-thia-11-aza-benzo[a]fluoren-8-ol

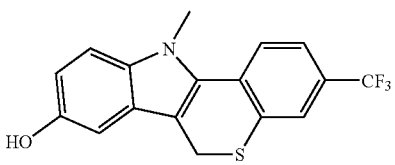

Following the procedure described in Example 58, using 8-methoxy-11-methyl-3-trifluoromethyl-6,11-dihydro-5-thia-11-aza-benzo[a]fluorene (349 mg) as the starting material, the title compound was prepared as a white solid.

$^1$H NMR (CDCl$_3$) δ 7.75-6.85 (m, 6H), 5.80 (br, 1H), 4.00 (s, 2H), 3.85 (s, 3H)

MS (m/z): MH+ (334)

EXAMPLE 70

3-fluoro-11-methyl-6,11-dihydro-5-thia-11-aza-benzo[a]fluoren-8-ol

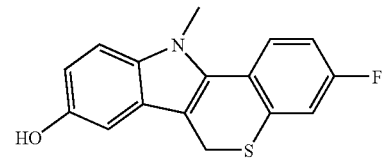

Following the procedure described in Example 58, using 3-fluoro-8-methoxy-11-methyl-6,11-dihydro-5-thia-11-aza-benzo[a]fluorine as the starting material, the title compound was prepared as a brown solid.

$^1$H NMR (CDCl$_3$) δ 7.55-6.82 (m, 6H), 5.20 (br, 1H), 3.95 (s, 2H), 3.82 (s, 3H)

MS (m/z): MH+ (285)

EXAMPLE 71

11-methyl-6,11-dihydro-5-thia-11-aza-benzo[a]fluoren-9-ol

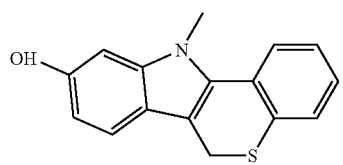

Following the procedure described in Example 58, using 9-methoxy-11-methyl-6,11-dihydro-5-thia-11-aza-benzo[a]fluorene (280 mg, 1 mmol) as the starting material, the title compound was prepared as a brown solid.

$^1$H NMR (CDCl$_3$) δ 7.62-6.70 (m, 7H), 4.08 (s, 2H), 3.85 (s, 3H)

MS (m/z): MH+ (266)

EXAMPLE 72

3-fluoro-11-methyl-6,11-dihydro-5-thia-11-aza-benzo[a]fluoren-10-ol

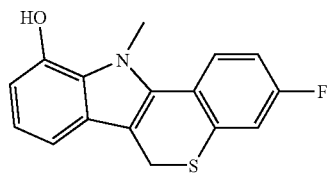

Following the procedure described in Example 58, using 3-Fluoro-10-methoxy-11-methyl-6,11-dihydro-5-thia-11-aza-benzo[a]fluorine (290 mg) as the starting material, the title compound was prepared as a brown solid.

$^1$H NMR (CDCl$_3$) δ 7.55-6.55 (m, 6H), 6.20 (br, 1H), 4.00 (s, 2H), 3.90 (s, 3H)

MS (m/z): MH+ (286).

EXAMPLE 73

3-bromo-11-methyl-6,11-dihydro-5-thia-11-aza-benzo[a]fluoren-8-ol

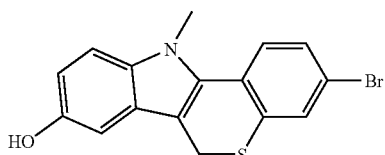

Following the procedure described in Example 58, using 3-Bromo-8-methoxy-11-methyl-6,11-dihydro-5-thia-11-aza-benzo[a]fluorine (359 mg), the title compound was prepared as a brown solid.

$^1$H NMR (CDCl$_3$) δ 7.52-6.85 (m, 6H), 4.10 (s, 2H), 3.85 (s, 3H)

MS (m/z): MH+ (346)

EXAMPLE 74

3-ethylsulfanylmethyl-2-(2-hydroxy-phenyl)-1-methyl-1H-indol-5-ol

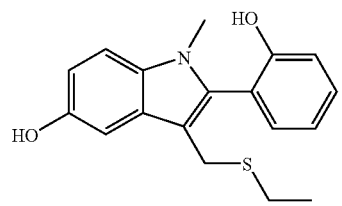

A mixture of 9-methoxy-11-methyl-6,11-dihydro-5-thia-11-aza-benzo[a]fluorine (95 mg, 0.358 mmol), EtSH (1.434 mmol. 4.0 eq.), and AlCl$_3$ (1.792 mmol, 5.0 eq.) in CH$_2$Cl$_2$ was stirred at 25° C. for 5 hours. The reaction mixture was then cooled to 0° C. and quenched with saturated aqueous NaHCO$_3$ solution. The aqueous solution was extracted with CH$_2$Cl$_2$ and the organic layers were dried and concentrated to yield a crude product. The crude product was purified by flash chromatograph to yield the title compound as a brown solid.

MS (m/z): MNa$^+$ (336), MH$^-$ (312)

$^1$H NMR (CDCl$_3$) δ 7.32-6.78 (m, 7H), 3.75 (d, 1H, J=13.1 Hz), 3.65 (d, 1H, J=13.1 Hz), 3.40 (s, 3H), 2.38 (q, 2H, J=6.5 Hz), 1.04 (t, 3H, J=6.5 Hz)

EXAMPLE 75

6,11-dihydro-5-thia-11-aza-benzo[a]fluoren-8-ol

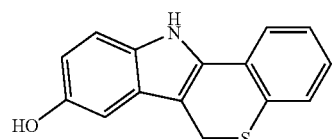

Following the procedure described in Example 58, using 8-Methoxy-6,11-dihydro-5-thia-11-aza-benzo[a]fluorene (1.76 g, 6.59 mmoL) as the starting material, the title compound was prepared as a brown solid $^1$H NMR (CDCl$_3$) δ 8.21 (br, s, 1H), 7.32~6.78 (m, 8H), 4.12 (s, 2H).

MS (m/z): MH+, 254.

EXAMPLE 76

5,11-dimethyl-5,11-dihydro-6H-indolo[3,2-c]quinolin-8-ol

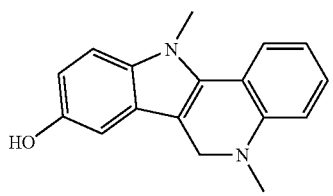

Following the procedure described in Example 58, using 8-methoxy-5,11-dimethyl-5,11-dihydro-6H-indolo[3,2-c]quinoline (410 mg) as the starting material, the title compounds was prepared as a brown solid.

$^1$H NMR (CDCl$_3$) δ 7.91-6.68 (m, 7H), 3.13 (s, 2H), 2.95 (s, 3H)

EXAMPLE 77

6,7-Dihydro-12H-5-thia-12-aza-dibenzo[a,e]azulen-9-ol

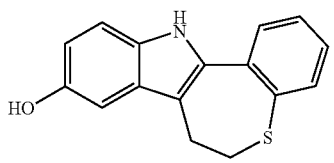

Following the procedure described in Example 58, using 9-methoxy-6,7-dihydro-12H-5-thia-12-aza-dibenzo[a,e]azulene (520 mg) as the starting material, the title compounds was prepared as a brown solid.

MS (m/z): MNa$^+$ (290), MH$^-$ (266)

EXAMPLE 78

9-methoxy-12H-5-thia-12-aza-dibenzo[a,e]azulene

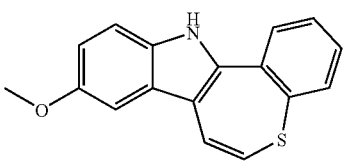

9-Methoxy-6,7-dihydro-12H-5-thia-12-aza-dibenzo[a,e]azulene (57 mg, 0.203 mmoL) in DMF (2 mL) was treated with KO$_2$ (58 mg, 0.811 mmoL) and 18-Crown-6 (54 mg, 0.203) and the reaction mixture was stirred at room temperature for 6 hours. Water was added to quench the reaction. The mixture was then partitioned between EtOAc and saturated NH$_4$Cl. The aqueous phase was extracted two times with EtOAc. The organic layer from each extraction was combined, washed with water, brine, dried over anhydrous Na$_2$SO$_4$, filtered and concentrated to yield a brown oil. The crude material (the oil) was then purified by column chromatography (silica gel, 1:1 hexanes:EtOAc as eluent) to yield the title compound as a brown solid.

$^1$H NMR (CDCl$_3$) 8.05 (br, s, 1H), δ 8.02~6.88 (m, 9H), 3.92 (s, 3H)

MS (m/z): MH+, 280.

EXAMPLE 79

Trifluoro-methanesulfonic acid, 11-methyl-6,11-dihydro-5-thia-11-aza-benzo[a]fluoren-8-yl ester

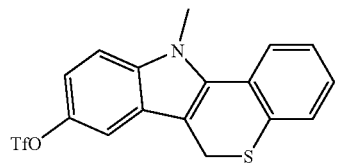

A mixture of 11-methyl-6,11-dihydro-5-thia-11-aza-benzo[a]fluoren-8-ol (780 mg, 2.90 mmol), Tf$_2$O (900 mg, 3.19 mmol, 1.1 eq.), and Et$_3$N (0.506 mL, 4.35 mmol, 1.5 eq.) in CH$_2$Cl$_2$ (10 mL) was stirred at 25° C. The reaction mixture was quenched with aqueous saturated NaHCO$_3$. The organic layer was washed with brine, dried, concentrated and purified by silica gel column (Hexane:EtOAc=4:1) to yield the title compound as a white solid.

$^1$H NMR (CDCl$_3$) δ 7.64-7.08 (m, 7H), 4.02 (s, 2H), 3.95 (s, 3H)

EXAMPLE 80 acetic acid 11-methyl-6,11-dihydro-5-thia-aza-benzo[a]fluoren-8-yl ester

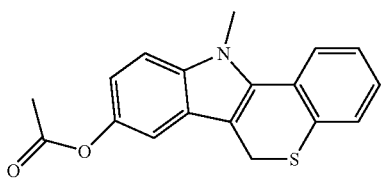

Acetyl chloride (11 mg, 0.14 mmol, 1.1 eq.) was added dropwise to a mixture of 8-methyl-6,11-dihydro-5-thia-11-aza-benzo[a]fluoren-8-ol (35 mg, 0.13 mmol) and Et$_3$N (28 µl, 0.2 mmol, 1.5 eq.) in CH$_2$Cl$_2$ (2 mL) at 0° C. The mixture was stirred at 0° C. for 2 hours and then warmed to 25° C. After being warmed, the reaction mixture was quenched by aqueous saturated NaHCO$_3$ solution. The organic layer was dried, concentrated and purified (silica gel column, 3:1 Hexane/EtOAc) to yield the title compound as a white solid.

MS (m/z): MNa$^+$ (346)

$^1$H NMR (CDCl$_3$) δ 7.59~6.95 (m, 7H), 4.03 (s, 2H), 3.94 (s, 3H), 2.32 (s, 3H)

EXAMPLE 81

Methanesulfonic acid 11-methyl-6,11-dihydro-5-thia-11-aza-benzo[a]fluoren-8-yl ester

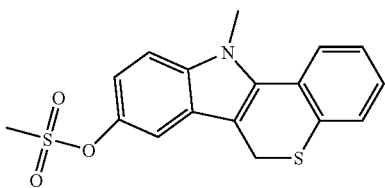

A mixture of 8-methyl-6,11-dihydro-5-thia-11-aza-benzo[a]fluoren-8-ol (35 mg, 0.131 mmol), CH$_3$SO$_2$Cl (15 μL, 0.197 mmol, 1.5 eq.), pyridine (20 mg, 0.262 mmol, 2.0 eq.) in CH$_2$Cl$_2$ (1 mL) was stirred at 25° C. for 2 hours. The mixture was then partitioned between CH$_2$Cl$_2$ and saturated NaHCO$_3$ aqueous solution. The aqueous layer was extracted three times with CH$_2$Cl$_2$. The combined organic layer was washed with brine, dried over anhydrous Na$_2$SO$_4$, filtered and concentrated to yield crude material. The crude material was purified by chromatography to yield the title compound as a white solid.

$^1$H NMR (CDCl$_3$) δ 7.66~7.14 (m, 6H), 4.05 (s, 2H), 3.98 (s, 3H), 3.12 (s, 3H)

EXAMPLE 82

1,1,2,2,3,3,4,4,4-nonafluoro-butane-1-sulfonic acid 11-methyl-6,11-dihydro-5-thia-11-aza-benzo[a]fluoren-8-yl ester

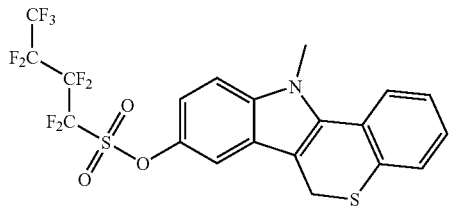

To a solution of 8-methyl-6,11-dihydro-5-thia-11-aza-benzo[a]fluoren-8-ol (180 mg, 0.711 mmol) in CH$_2$Cl$_2$ (20 mL), Et$_3$N (129 μL, 0.924 mmol) was added dropwise followed by CF$_3$(CF$_2$)$_3$SO$_2$F (153 μL, 0.853 mmol) at 0° C. The reaction mixture was slowly warmed up to 25° C. over 2 hours. Then CH$_2$Cl$_2$, water, and saturated aqueous NaHCO$_3$ solution were added to the mixture. The aqueous layer was extracted with CH$_2$Cl$_2$ and the organic layers were washed with brine, dried, and concentrated. Flash chromatography purification (12% EtOAc/Hexane) was used to yield the title as a white solid.

$^1$H NMR (CDCl$_3$) δ 7.61~7.14 (m, 7H), 4.05 (s, 2H), 3.98 (s, 3H)

EXAMPLE 83

2,2-dimethyl-propionic acid 11-methyl-6,11-dihydro-5-thia-11-aza-benzo[a]fluoren-8-yl ester

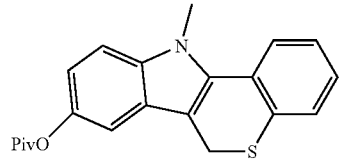

Following the procedure in Example 80, using 11-methyl-6,11-dihydro-5-thia-11-aza-benzo[a]fluoren-8-ol (105 mg, 0.393 mmol) and PivCl (71 mg, 0.59 mmol) as the starting material, the title compound was prepared as a white solid.

MS (m/z): MH$^+$ (352)

$^1$H NMR (CDOD$_3$) δ 7.65-6.91 (m, 7H), 4.05 (s, 2H), 3.96 (s, 3H), 1.40 (s, 9H)

EXAMPLE 84

8-(tert-butyl-dimethyl-silanyloxy)-11-methyl-6,11-dihydro-5-thia-11-aza-benzo[a]fluorene

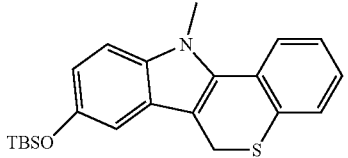

Following the procedure described in Example 80, using 11-methyl-6,11-dihydro-5-thia-11-aza-benzo[a]fluoren-8-ol (1.15 g, 3.123 mmol) and TBSCl (562 mg, 3.75 mmol) as the starting material, the title compound was prepared as a white solid.

MS (m/z): MH+ (382)

$^1$H NMR (CDCl$_3$) δ 7.50-6.78 (m, 7H), 3.92 (s, 2H), 3.75 (s, 3H), 1.05 (s, 9H), 0.18 (s, 6H)

EXAMPLE 85

8-(tert-butyl-dimethyl-silanyloxy)-6,11-dihydro-5-thia-11-aza-benzo[a]fluorene

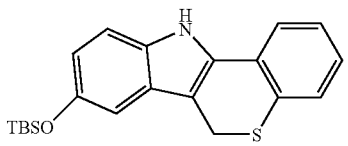

6,11-dihydro-5-thia-11-aza-benzo[a]fluoren-8-ol (820 mg, 3.24 mmoL) in DMF (10 mL) was treated with imidazole (331 mg, 4.862 mmoL) followed by TBSCl (733 mg, 4.862 mmoL) at room temperature. The reaction was stirred for 2 hours. The reaction mixture was then partitioned between CH$_2$Cl$_2$ and water. The organic layer was washed with brine, dried over anhydrous Na$_2$SO$_4$, filtered and concentrated to yield a brown oil. The crude material (the oil) was then purified by column chromatography (silica gel, hexanes:EtOAc 4:1 as eluent) to yield the title compound as a brown solid.

$^1$H NMR (CDCl$_3$) δ 8.58 (br, s, 1H), 7.35~6.75 (m, 7H), 4.18 (s, 2H), 1.09 (s, 9H), 0.23 (s, 6H).

MS (m/z): MH+, 368.

EXAMPLE 86

2,2-dimethyl-propionic acid 6,11-dihydro-5-thia-11-aza-benzo[a]fluoren-8-yl-ester

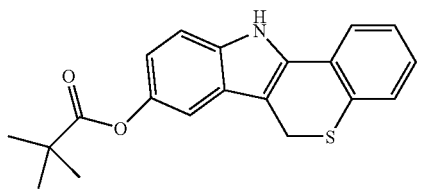

6,11-dihydro-5-thia-11-aza-benzo[a]fluoren-8-ol (1.01 g, 3.99 mmoL) in CH$_2$Cl$_2$ (5 mL) was treated with pyridine (0.387 mL, 4.788 mmoL) followed by PivCl (0.541 mL, 4.389 mmoL) at 0° C. The reaction mixture was slowly warmed to room temperature over 2 hours. The reaction mixture was then partitioned between CH$_2$Cl$_2$ and saturated NH$_4$Cl. The aqueous phase was extracted two times with CH$_2$Cl$_2$. The organic layer from each extraction was combined, washed with water, brine, dried over anhydrous Na$_2$SO$_4$, filtered and concentrated to yield a brown oil. The crude material (the oil) was then purified by column chromatography (silica gel, hexanes:EtOAc 4:1 as eluent) to yield the title compound as a pale foam.

$^1$H NMR (CDCl$_3$) δ 8.45 (br, s, 1H), 7.35~6.72 m, 7H), 4.10 (s, 2H), 1.35 (s, 9H).

MS (m/z): MH+, 338.

EXAMPLE 87

9-(tert-Butyl-dimethyl-silanyloxy)-6,7-dihydro-12H-5-thia-12-aza-dibenzo[a,e]azulene

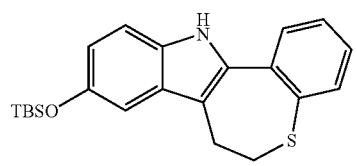

Following the procedure described in Example 80, using 6,7-Dihydro-12H-5-thia-12-aza-dibenzo[a,e]azulen-9-ol (350 mg, 1.31 mmol) and TBSCl (225 mg, 1.50 mmol) as the starting material, the title compound was prepared as a white solid.

MS (m/z): MH+ (382)

EXAMPLE 88

3,8-bis-(tert-butyl-dimethyl-silanyloxy)-6,11-dihydro-5-thia-11-aza-benzo[a]fluorene

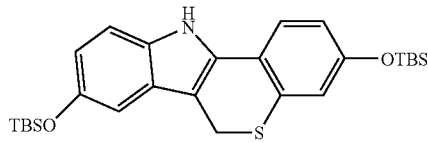

6,11-dihydro-5-thia-11-aza-benzo[a]fluorene-3,8-diol (298 mg, 1.11 mmoL) in DMF (5 mL) was treated with imidazole (188 mg, 2.77 mmoL) followed by TBSCl (417 mg, 2.77 mmoL) at room temperature. The reaction was stirred for 2 hours. The reaction mixture was then partitioned between CH$_2$Cl$_2$ and water. The organic layer was washed with brine, dried over anhydrous Na$_2$SO$_4$, filtered and concentrated to yield a brown oil. The crude material (the oil) was then purified by column chromatography (silica gel, hexanes:EtOAc 3:1 as eluent) to yield the title compound as a brown solid.

$^1$H NMR (CDCl$_3$) δ 7.85 (br, s, 1H), 7.08~6.35 (m, 6H), 3.98 (s, 2H) 0.85 (s, 9H), 0.81 (s, 9H), 0.08 (s, 6H), 0.06 (s, 6H).

MS (m/z): MNa+, 520, MH−, 496.

EXAMPLE 89

[2-(8-methoxy-6H-5-thia-11-aza-benzo[a]fluoren-11-yl)-ethyl]-dimethyl-amine

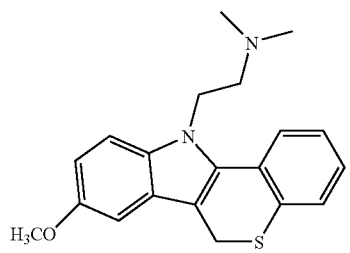

The title compound was prepared from 8-methoxy-6,11-dihydro-5-thia-11-aza-benzo[a]fluroene (1.50 g, 5.62 mmol) and ClCH$_2$CH$_2$N(Me)$_2$ (620 mg, 5.80 mmol) were reacted according to the procedure described in Example 19, wherein the procedure was slightly modified, by addition of a catalytic amount of KI ~50 mg. In this way, the title compound was prepared as a brown solid.

$^1$H NMR (CDCl$_3$) δ 7.63-6.88 (m, 7H), 4.36 (t, 2H, J=6.6 Hz), 4.01 (s, 2H), 3.83 (s, 3H), 2.72 (t, 2H, J=6.6 Hz), 2.31 (s, 6H)

MS (m/z): MH$^+$ (339)

EXAMPLE 90

11-methyl-6,11-dihydro-5-thia-aza-benzo[a]fluorene-8-carbonitrile

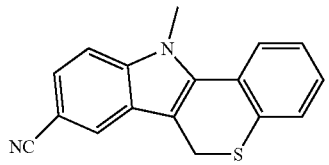

A mixture of 8-bromo-11-methyl-6,11-dihydro-5-thia-11-aza-benzo[a]fluorene (270 mg), as prepared in Example 57, and CuCN (270 mg) in DMF (25 ml) was reflux overnight at 170° C. The reaction mixture was filtered through a pad of Celite and then partitioned between saturated NaHCO$_3$ aqueous solution and EtOAc. The aqueous layer was extracted with EtOAc, the organic layers were dried and concentrated to yield crude product. The crude product was purified by chromatography (Hexane:ethyl acetate=5:1) to yield the title compound as a white solid.

$^1$H NMR (CDCl$_3$) δ 7.90 (s, 1H), 7.65-7.25 (m, 6H), 4.08 (s, 2H), 3.98 (t, 3H)

MS (m/z): MH+ (277)

EXAMPLE 91

11-methyl-6,11,dihydro-5-thia-aza-benzo[a]fluorene-8-carboxylic acid

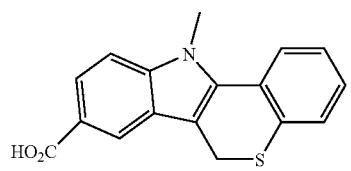

6,11-dihydro-5-thia-11-aza-benzo[a]fluorene-3,8-diol (1 mmol, 330 mg), as prepared in Example 31, in THF (15 ml) was treated with n-BuLi (2.0 M, 0.6 ml, 1.2 mmol) at −78° C. for 30 minutes. Dry ice (1 equiv.) was then added to the reaction mixture at −78° C. After slowly warming the reaction mixture to room temperature, the reaction mixture was quenched by saturated ammonium chloride, extracted by ethyl acetate, and purified by chromatography (Hexane:ethyl acetate=1:1) to yield the title compound as a white solid.

$^1$H NMR (CDCl$_3$) δ 8.50 (s, 1H), 8.05-7.20 (m, 7H), 4.15 (s, 2H), 4.00 (s, 3H)

MS (m/z): MH+ (296)

EXAMPLE 92

11-methyl-6,11-dihydro-5-oxa-11-aza-benzo[a]fluorene-8-carboxylic acid

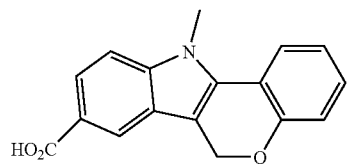

n-BuLi was added dropwise into 8-bromo-11-methyl-6,11-dihydro-5-oxa-11-aza-benzo[a]fluorene (420 mg, 1.338 mmoL) in THF (5 mL) at −78° C. After an additional 30 minutes, the reaction mixture was transferred into dry ice (~10 g). The reaction mixture was then slowly warmed to room temperature. The solvent was removed and the residue was partitioned between EtOAc and 1 N NaOH solution. The aqueous layer was then acidified to a pH of about 2 using 1N HCl and extracted three times with EtOAc. The organic phase of each extraction was combined, washed with water, brine, dried over anhydrous Na$_2$SO$_4$, filtered and concentrated to yield a clear oil. The oil was then purified by column chromatography (silica gel, hexanes:EtOAc 1:1 as eluent) to yield the title compound as a white solid.

$^1$H NMR (CDCl$_3$) δ 7.55~6.68 (m, 7H), 5.30 (s, 2H), 3.88 (s, 3H).

MS (m/z): MH+, 280.

EXAMPLE 93

11-Methyl-6,11-dihydro-5-thia-11-aza-benzo[a]fluorene-8-carboxylic acid methyl ester

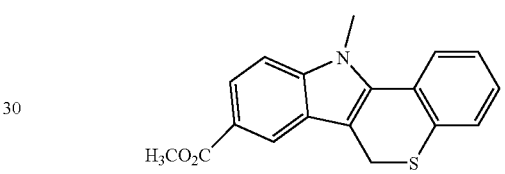

6,11-dihydro-5-thia-11-aza-benzo[a]fluorene-3,8-diol (1 mmol, 330 mg), as prepared in Example 31, in THF (15 ml) was treated with n-BuLi (2.0 M, 0.6 ml, 1.2 mmol) at −78° C. for 30 minutes, then methyl chloroformate (1 equivalent) was added drop by drop to the reaction mixture at −78° C. After slowly warming up to room temperature, the reaction mixture was quenched by saturated ammonium chloride, extracted by ethyl acetate and purified by chromatography (Hexane:ethyl acetate=5:1) to yield the title compound as a white solid.

1H NMR (CDCl$_3$) δ 8.35 (s, 1H), 7.95-7.15 (m, 7H), 4.11 (s, 2H), 3.95 (s, 3H), 4.00 (s, 3H)

MS (m/z): MH+ (309)

EXAMPLE 94

8-methoxy-11-methyl-6,11-dihydro-5-oxa-4,11-diaza-benzo[a]fluoren-6-ol

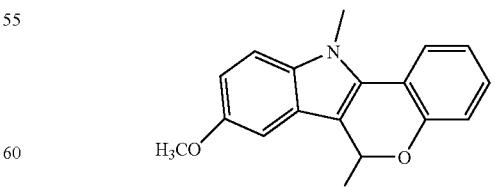

To a mixture of 8-methoxy-11-methyl-6,11-dihydro-5-oxa-4,11-diaza-benzo[a]fluorene (500 mg, 1.887 mmol) in CH$_3$CN (15 mL) was added AlCl$_3$ (378 mg, 1.5 eq.). After 60 hours at 25° C., the mixture was quenched with saturated NaHCO$_3$. The aqueous layer was extracted with EtOAc. The organic layers were dried and concentrated to yield the title compound as a brown solid.

MS (m/z): MH$^+$ (282), MNa$^+$ (304), MH$^-$ (280)

$^1$H NMR (CDCl$_3$) δ 9.58 (s, 1H), 7.81-6.94 (m, 7H), 5.96 (br s, 1H), 3.87 (s, 3H), 3.62 (s, 3H).

EXAMPLE 95

1-[8(tert-butyl-dimethyl-silanyloxy)-6H-5-thia-11-aza-benzo[a]fluoren-11-yl]-ethanone

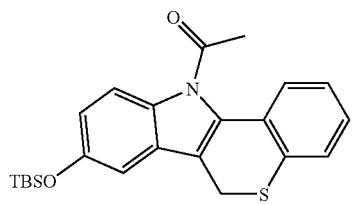

8-(tert-Butyl-dimethyl-silanyloxy)-6,11-dihydro-5-thia-11-aza-benzo[a]fluorene (170 mg, 0.462 mmoL) in DMF (2 mL) was treated with NaH (60%, 37 mg, 0.925 mmoL) at 0° C. Acetyl chloride (52 mg, 0.693 mmoL) was added dropwise into the reaction 30 minutes later. The reaction mixture was than slowly warmed to room temperature over 2 hours. The reaction was quenched with saturated NH$_4$Cl. The residue was partitioned between CH$_2$Cl$_2$ and saturated NaHCO$_3$. The aqueous phase was extracted two times with CH$_2$Cl$_2$. The organic layer from each extraction was combined, washed with water, brine, dried over anhydrous Na$_2$SO$_4$, filtered and concentrated to yield a brown oil. The oil was then purified by column chromatography (silica gel, hexanes:EtOAc 5:1 as eluent) to yield the title compound as a pale solid.

$^1$H NMR (CDCl$_3$) δ 7.88~6.62 (m, 7H), 3.70 (s, 2H), 2.15 (s, 3H), 0.81 (s, 9H), 0.05 (s, 6H).

MS (m/z): MH+, 410, MNa+, 432.

EXAMPLE 96

1-(8-hydroxy-6H-5-thia-11-aza-benzo[a]fluoren-11-yl)ethan-one

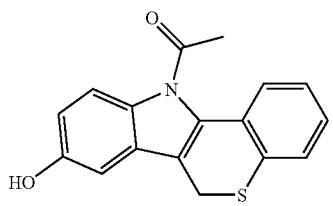

1-[8(tert-butyl-dimethyl-silanyloxy)-6H-5-thia-11-aza-benzo[a]fluoren-11-yl]-ethanone (136 mg, 0.332 mmol) in THF (5 mL) was added TBAF (332 μL, 1.0 N in THF, 0.332 mmol, 1.0 eq.). After 1 hour at 25° C., the reaction mixture was partitioned between saturated NaHCO$_3$ aqueous solution and CH$_2$Cl$_2$, the aqueous layer was extracted with CH$_2$Cl$_2$ and the organic layers were dried and concentrated to yield crude product. The crude product was purified by chromatography to yield the title compound as a yellow solid.

MS (m/z): MH$^+$ (296), MH$^-$ (294)

$^1$H NMR (CDCl$_3$) δ 8.31 (s, 1H), 7.42-6.96 (m, 7H), 4.14 (s, 2H), 2.34 (s, 3H)

EXAMPLE 97

Acetic acid 4-(8-methoxy-6H-5-oxa-11-aza-benzo[a]fluorene-11-carbonyl)-phenyl ester

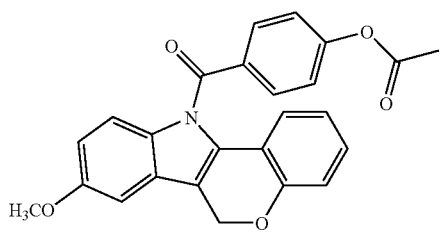

A solution of 4-acetoxy-benzoic acid (108 mg, 0.598 mmoL) in CH$_2$Cl$_2$ (5 mL) was treated with (COCl)$_2$ (0.07 mL, 0.796 mmoL) and 1 drop, a catalytic amount, of DMF at 0° C. The reaction mixture was slowly warmed to room temperature. The CH$_2$Cl$_2$ was removed and dried in vacuo. The 4-acetoxy-benzoic acyl chloride in THF (2 mL) was treated with the indole-8-Methoxy-6,11-dihydro-5-oxa-11-aza-benzo[a]fluorene (100 mg, 0.398 mmoL) followed by Et$_3$N (0.796 mmol., 0.11 mL) at 0° C. The reaction was slowly warmed to room temperature over 2 hours. THF was removed in vacuo. The residue was partitioned between CH$_2$Cl$_2$ and saturated NaHCO$_3$. The aqueous phase was extracted two times with CH$_2$Cl$_2$. The organic layers from the two extractions were combined, washed with water and brine, dried over anhydrous Na$_2$SO$_4$, filtered and concentrated to yield a brown oil. The crude material (the oil) was then purified by column chromatography (silica gel, hexanes:EtOAc 4:1 as eluent) to yield the title compound as a pale solid.

$^1$H NMR (CDCl$_3$) δ 8.02~6.75 (m, 11H), 5.52 (s, 2H), 3.98 (s, 3H), 2.55 (s, 3H).

MS (m/z): MH+, 414.

EXAMPLE 98

1-(8-methoxy-6H-5-oxa-11-aza-benzo[a]fluoren-11-yl)-ethanone

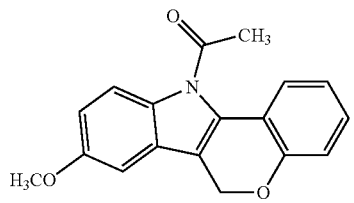

Acetyl chloride (0.064 mL, 0.896 mmoL) in CH$_2$Cl$_2$ (2 mL) was treated with 8-methoxy-6,11-dihydro-5-oxa-11-aza-benzo[a]fluorene (150 mg, 0.598 mmoL) followed by Et$_3$N (0.896 mmol., 0.125 mL) at 0° C. The reaction mixture was then slowly warmed to room temperature over 2 hours. The reaction mixture was then partitioned between CH$_2$Cl$_2$ and saturated NaHCO$_3$. The aqueous phase was extracted two times with CH$_2$Cl$_2$. The organic layers from the two extractions were then combined, washed with water and brine, dried over anhydrous Na₂SO₄, filtered and concentrated to yield a brown oil. The crude material was then purified by column chromatography (silica gel, hexanes:EtOAc 3:1 as eluent) to yield the title compound as a pale solid.

¹H NMR (CDCl₃) δ 7.98~6.80 (m, 7H), 5.25 (s, 2H), 3.88 (s, 3H), 2.58 (s, 2H).

MS (m/z): MH+, 294.

EXAMPLE 99

11-(4-benzyloxy-benzyl)-8-methoxy-6,11-dihydro-5-oxa-11-aza-benzo[a]fluorene

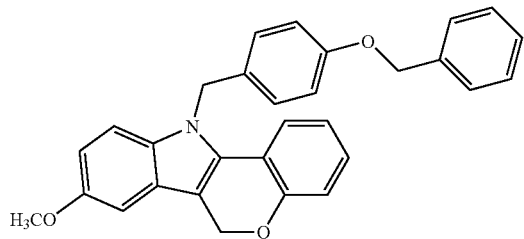

To a mixture of 8-methoxy-6,11-dihydro-5-oxa-11-aza-benzo[a]fluorene (100 mg, 0.398 mmoL) in DMF (2 mL) was added NaH (60%, 24 mg, 0.598 mmoL) at 0° C. After 10 minutes, benzyl chloride (139 mg, 0.598 mmoL) was added dropwise into the reaction mixture at 0° C. The reaction mixture was slowly warmed to room temperature over 2 hours. The reaction mixture was then partitioned between EtOAc and saturated NH₄Cl. The aqueous phase was extracted two times with EtOAc. The organic layers from the two extractions were combined, washed with water, brine, dried over anhydrous Na₂SO₄, filtered and concentrated to yield a brown oil. The oil was then purified by column chromatography (silica gel, hexanes:EtOAc 4:1 as eluent) to yield the title compound as a pale solid.

¹H NMR (CDCl₃) δ 7.40~6.78 (m, 16H), 5.08 (s, 4H), 5.02 (s, 2H), 4.55 (s, 2H), 3.88 (s, 3H).

MS (m/z): MH+, 448, MNa+, 470.

EXAMPLE 100

11-[4-(2-chloro-ethoxy)-benzyl]-8-methoxy-6,11-dihydro-5-thia-11-aza-benzo[a]fluorine and 6a-[4-(2-chloro-ethoxy)-benzyl]-8-methoxy-6,6a-dihydro-5-thia-11-aza-benzo[a]fluorine

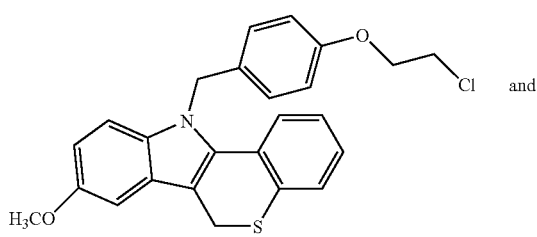

and

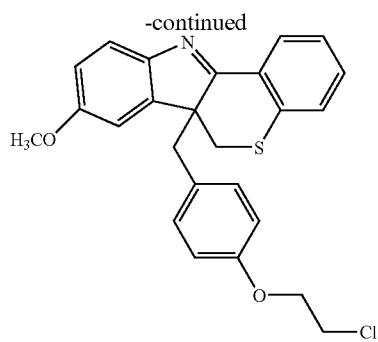

NaH (60%, 86 mg, 2.14 mmoL) was added into 8-methoxy-6,11-dihydro-5-thia-11-aza-benzo[a]fluorine (520 mg, 1.95 mmoL) in DMF (10 mL) at 0° C. After 10 minutes, the benzyl chloride (487 mg, 1.95 mmoL) was added dropwise into the reaction at 0° C. The reaction mixture was slowly warmed to room temperature over 2 hours. The reaction mixture was then partitioned between EtOAc and saturated NH₄Cl. The aqueous phase was extracted two times with EtOAc. The organic layers from the two extractions were combined, washed with water, brine, dried over anhydrous Na₂SO₄, filtered and concentrated to yield a brown oil. The crude material (the oil) was then purified by column chromatography (silica gel, hexanes:EtOAc 4:1 as eluent) to yield the both products as yellow solids.

11-[4-(2-chloro-ethoxy)-benzyl]-8-methoxy-6,11-dihydro-5-thia-11-aza-benzo[a]fluorine ¹H NMR (CDCl₃) δ 7.50~6.82 (m, 11H), 5.41 (s, 2H), 4.23 (t, J=10.5 Hz, 2H), 4.12 (s, 2H), 3.88 (s, 3H), 3.82 (t, J=10.5 Hz, 2H).

MS (m/z): MH+, 436.

6a[4-(2-chloro-ethoxy)-benzyl]-8-methoxy-6,6a-dihydro-5-thia-11-aza-benzo[a]fluorine ¹H NMR (CDCl₃) δ 8.06~6.45 (m, 11H), 4.15 (abq, J=8.5 Hz, 2H), 3.85 (t, J=8.0 Hz, 2H), 3.80 (s, 3H), 3.32 (abq, J=12.5 Hz, 1H), 3.28 (t, J=8.0 Hz, 2H), 2.90 (abq, J=12.5 Hz, 1H).

MS (m/z): MH+, 436.

EXAMPLE 101

(8-methoxy-5H-6-thia-11-aza-benzo[s]fluoren-11-yl)-[4-(2-piperidin-1-yl-ethoxy)-phenyl]-methanone

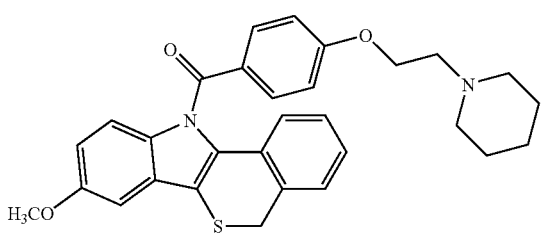

4-(2-Piperidin-1-yl-ethoxy)-benzoic acid (231 mg, 0.808 mmoL) was dissolved in THF (2 mL). SOCl₂ (0.08 mL, 1.01 mmoL) was added into the reaction at room temperature. The reaction mixture was then heated at 50° C. until it turned clear.

THF was then removed and the acyl chloride was dried in vacuo. The 8-methoxy-5,11-dihydro-6-thia-11-aza-benzo[a]fluorine (180 mg, 0.673 mmoL) in DMF (5 mL) was treated with NaH (60%, 0.076 mg, 1.884 mmoL) one portion at 0° C. After addition of NaH, the reaction mixture was stirred for additional 10 minutes. 4-(2-Piperidin-1-yl-ethoxy)-benzoic acyl chloride in DMF (2 mL) was added into the reaction mixture. The reaction was then slowly warmed to room temperature. Water and CH$_2$Cl$_2$ were added and the aqueous layer was exacted three times with CH$_2$Cl$_2$. The organic layer from each extraction was combined, washed with water, brine, dried over anhydrous Na$_2$SO$_4$, filtered and concentrated to yield a brown oil. The oil was then purified by column chromatography (silica gel, CH$_2$Cl$_2$: MeOH 6:1 as eluent) to yield the title compound as a colorless oil.

$^1$H NMR (CDCl$_3$) δ 8.05~6.78 (m, 11H), 4.20 (t, J=10.5 Hz, 2H), 4.02 (s, 2H), 3.95 (s, 3H), 2.90 (t, J=10.5 Hz, 2H0, 2.60 (m, 4H), 1.68 (m, 4H0, 1.50 (m, 2H).

MS (m/z): MH+, 499.

EXAMPLE 102

{2-[4-(7-benzyloxy-3-methoxy-benzo[4,5]furo[3,2-b]indol-10-ylmethyl)-phenoxy]-ethyl}-diethyl-amine

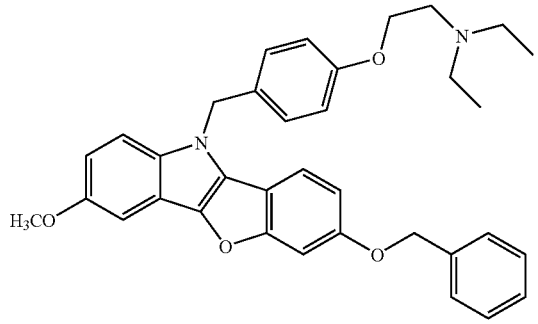

To a mixture of 7-benzyloxy-3-methoxy-10H-benzo[4,5]furo[3,2-b]indole (102 mg, 0.297 mmol) in DMF (5 mL) was added NaH (37 mg, 60% in mineral oil, 3.0 eq.) followed by [2-(4-chloromethyl-phenoxy)-ethyl]-diethyl-amine hydrochloride salt (99 mg, 0.356 mmol) at 0° C. The mixture was stirred at 0° C. for 30 minutes, warmed to 25° C., and quenched by NH$_4$Cl (solid). EtOAc and water were then added to the mixture. The reaction mixture was then partitioned between EtOAc and water. The aqueous layer was extracted three times with EtOAc. The combined organic layer was washed with brine, dried over anhydrous Na$_2$SO$_4$, filtered and concentrated to yield crude material. The crude material was purified by silica gel (EtOAc to CH$_2$Cl$_2$:MeOH 5:1) to yield the title compound as a brown solid.

MS (m/z): MH+ (549)

$^1$H NMR (CDCl$_3$) δ 7.48-6.78 (m, 15H), 5.46 (s, 2H), 5.12 (s, 2H), 3.98 (t, 2H, J=6.6 Hz), 3.88 (s, 3H), 2.82 (t, 2H, J=6.6 Hz), 2.60 (q, 4H, J=6.7 Hz), 1.05 (t, 6H)

EXAMPLE 103

Diethyl-{2-[4-(8-methoxy-6H-5-oxa-benzo[a]fluoren-11-ylmethyl)-phenoxy]-ethyl}-amine

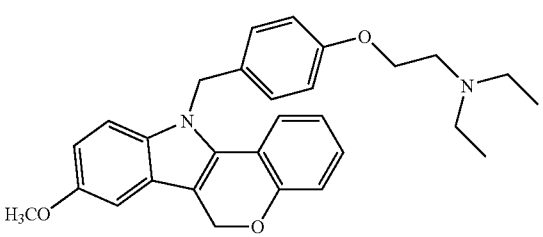

Following the procedure described in Example 102, using 8-methoxy-6,11-dihydro-5-oxa-11-aza-benzo[a]fluorene (406 mg, 1.62 mmol) and [2-(4-chloromethyl-phenoxy)-ethyl]-diethyl-amine hydrochloride salt as the starting material, the title compound was prepared as a brown solid.

MS (m/z): MH+ (457)

$^1$H NMR (CDCl$_3$) δ 7.28-6.80 (m, 7H), 5.48 (d, 2H, J=1.5 Hz), 3.97 (m, 2H), 3.89 (s, 2H), 2.85 (q, 2H, J=6.5 Hz), 2.65 (m, 4H), 1.07 (m, 6H)

EXAMPLE 104

8-Methoxy-11-[4-(2-piperidin-1-yl-ethoxy)-benzyl]-6,11-dihydro-5-oxa-11-aza-benzo[a]fluorene

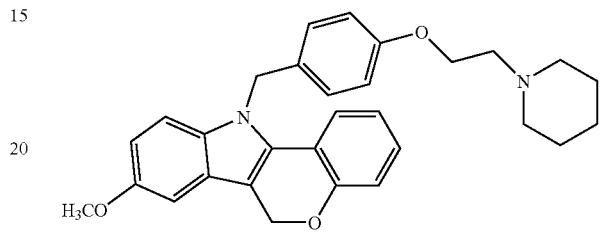

Following the procedure described in Example 102, using 8-methoxy-6,11-dihydro-5-oxa-11-aza-benzo[a]fluorene (150 mg, 0.562 mmol) and [2-(4-chloromethyl-phenoxy)-ethyl]-cyclohexanyl-amine hydrochloride salt as the starting material, the title compound was prepared as a brown solid.

MS (m/z): MH− (468)

EXAMPLE 105

6a-[4-(2-piperidin-1-yl-ethoxy)-benzyl]-6,6a-dihydro-5-thia-11-aza-benzo[a]fluoren-8-ol

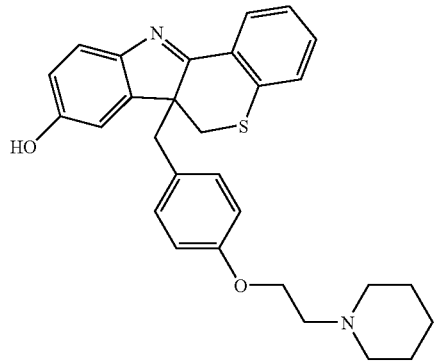

8-Methoxy-11-[4-(2-piperidin-1-yl-ethoxy)-benzyl]-6,11-dihydro-5-thia-11-aza-benzo[a]fluorene (93 mg, 0.192 mmoL) in CH$_2$Cl$_2$ (5 mL) was treated with EtSH (0.06 mL, 0.768 mmoL) followed by AlCl$_3$ (128 mg, 0.959 mmoL) at room temperature. The reaction mixture was stirred at room temperature for 5 hours. The reaction was then cooled to 0° C. and saturated NaHCO$_3$ was added to quench the reaction mixture. The residue was partitioned between CH$_2$Cl$_2$ and water. The organic layer was washed with brine, dried over anhydrous Na$_2$SO$_4$, filtered and concentrated to yield a brown oil. The crude material (the oil) was then purified by column chromatography (silica gel, CH$_2$Cl$_2$:MeOH 4:1 as eluent) to yield the title compound as a colorless oil.

$^1$H NMR (CDCl$_3$) δ 7.90~6.52 (m, 12H), 3.98 (t, J=8.5 Hz, 2H), 3.35 (abq, J=11.5 Hz, 2H), 3.10 (abq, J=10.5 Hz, 2H), 2.75 (t, J=8.5 Hz, 2H), 2.65 (m, 4H), 1.60 (m, 4H), 1.45 (m, 2H).

MS (m/z): MH+, 471.

EXAMPLE 106

10-[4-(2-diethylamino-ethoxy)-benzyl]-3-methoxy-10H-benzo[4,5]furo[3,2-b]indol-7-ol

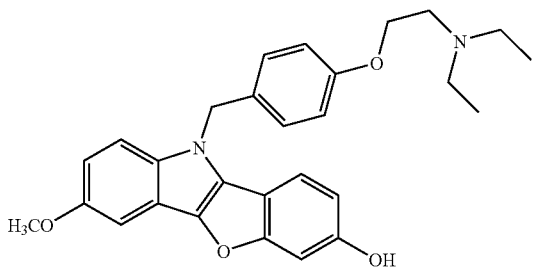

A mixture of {2-[4-(7-benzyloxy-3-methoxy-benzo[4,5]furo[3,2-b]indol-10-ylmethyl)-phenoxy]-ethyl}-diethylamine (102 mg, 0.186 mmol) and 10% Pd/C (~100 mg) in EtOH (10 mL) was stirred under a $H_2$ balloon at 25° C. overnight. The solution was filtered, concentrated and purified to yield the title compound as a yellow solid.

MS (m/z): $MH^+$ (459)

$^1$H NMR (CDCl$_3$) δ 7.18-6.54 (m, 10H), 5.22 (s, 2H), 4.01 (t, 2H, J=6.4 Hz), 3.79 (s, 3H), 2.94 (t, 2H, J=6.4 Hz), 2.75 (q, 4H, J=6.4 Hz), 1.05 (t, 6H, J=6.6 Hz)

EXAMPLE 107 diethyl-{2-[4-(3-methoxy-benzo[4,5]furo[3,2-b]indol-10-ylmethyl)-phenoxy]-ethyl}-amine

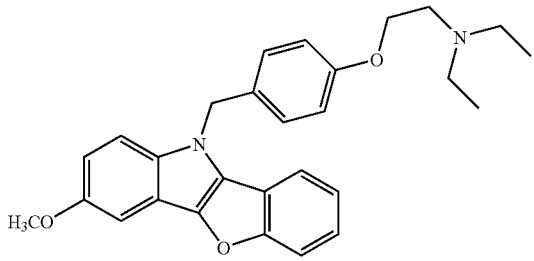

Following the procedure described in Example 102, using 3-methoxy-10H-benzo[4,5]furo[3,2-b]indole (405 mg, 1.517 mmol) and [2-(4-chloromethyl-phenoxy)-ethyl]-diethylamine hydrochloride salt as a starting material, the title compound was prepared as a brown solid.

$^1$H NMR (CDCl$_3$) δ 7.54-6.78 (m, 11H), 5.40 (s, 2H), 4.04 (t, 2H, J=6.5 Hz), 3.87 (s, 3H), 2.85 (t, 2H, J=6.6 Hz), 2.62 (q, 4H, J=6.6 Hz), 1.05 (t, 6H, J=6.6 Hz)

EXAMPLE 108

9-methoxy-12-[4-(2-pyrrolidin-1-yl-ethoxy)-benyl]-6,7-dihydro-12H-5-thia-12-aza-dibenzo[a,e]azulene

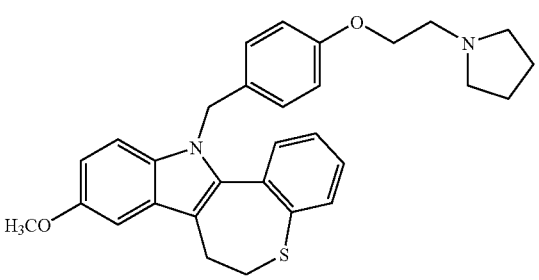

Following the same procedure in Example 102, using 9-methoxy-6,7-dihydro-12H-5-thia-12-aza-dibenzo[a,e]azulene (562 mg) and [2-(4-chloromethyl-phenoxy)-ethyl]-cyclopentyl-amine hydrochloride salt as the starting material, the title compound was prepared as a brown solid.

MS (m/z): $MH^+$ (485)

$^1$H NMR (CDCl$_3$) δ 8.12-6.63 (m, 11H), 5.02 (s, 2H), 4.15 (t, 2H, J=6.5 Hz), 3.48 (s, 3H), 3.38 (t, 2H, J=6.6 Hz), 3.23 (t, 2H, J=6.6 Hz), 2.83 (t, 2H, J=6.6 Hz), 2.68 (broad s, 4H), 1.67 (m, 4H)

EXAMPLE 109

9-(tert-Butyl-dimethyl-silanyloxy)-12-[4-(2-piperidin-1-yl-ethoxy)-benzyl]-6,7-dihydro-12H-5-thia-12-aza-dibenzo[a,e]azulene

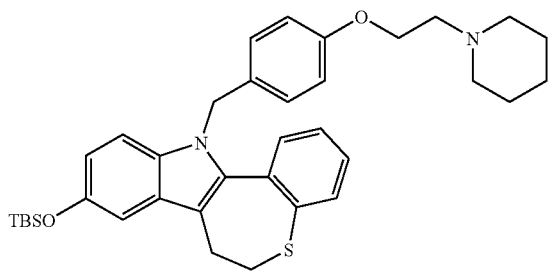

Following the same procedure in Example 102, using 9-(tert-Butyl-dimethyl-silanyloxy)-6,7-dihydro-12H-5-thia-12-aza-dibenzo[a,e]azulene (190 mg, 0.5 mmol) and [2-(4-chloromethyl-phenoxy)-ethyl]-cyclohexanyl-amine hydrochloride salt as the starting material, title compound was prepared as a brown solid. The compound was used in the next step without additional purification.

MS (m/z): $MH^+$ (586)

EXAMPLE 110

12-[4-(2-piperidin-1-yl-ethoxy)-benzyl]-6,7-dihydro-12H-5-thia-12-aza-dibenzo[a,e]azulen-9-ol

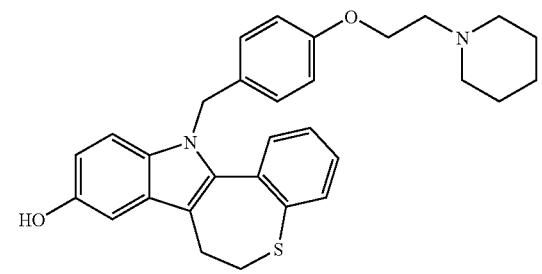

9-(tert-Butyl-dimethyl-silanyloxy)-12-[4-(2-piperidin-1-yl-ethoxy)-benzyl]-6,7-dihydro-12H-5-thia-12-aza-dibenzo[a,e]azulene (130 mg, 0.222 mmol) in 5 mL 1.0 N TBAF in THF solution was stirred for 30 min at room temperature. The reaction was worked up by $CH_2Cl_2$ extraction three times from water. The combined organic layer was dried and concentrated and purified by column using 4:1 $CH_2Cl_2$ and methanol solution to yield the title compound as a brown solid.

MS (m/z): $MH^+$ (485), $MH^-$ (483)

$^1$H NMR (CDCl$_3$) δ 8.12-8.18 (s, 1H), 7.58-6.61 (m, 11H), 4.40 (s, 1H), 4.05 (m, 2H), 3.34 (t, 2H, J=6.6 Hz), 3.13 (m, 2H), 2.72 (m, 2H), 2.53 (br s, 4H), 1.58 (br s, 4H), 1.39 (br m, 2H)

EXAMPLE 111

3-methoxy-10-[4-(2-piperidin-1-yl-ethoxy)-benzyl]-10H-benzo[4,5]furo[3,2-b]indole

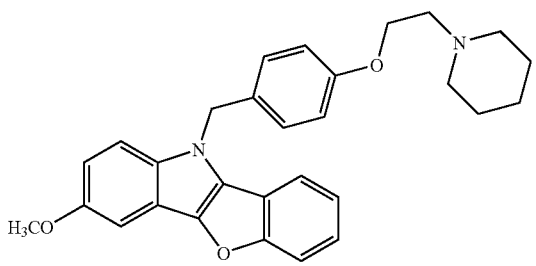

Following the same procedure in Example 102, using 8-methoxy-6,11-dihydro-5-thia-11-aza-benzo[a]fluorene (420 mg, 1.573 mmol) and 1-[2-(4-chloromethyl-phenoxy)-ethyl]-piperidine (1.2 eq.) as the starting material, the title compound was prepared as a brown solid.

MS (m/z): MH+ (485)

$^1$H NMR (CDCl$_3$) δ 7.52-6.76 (m, 11H), 5.38 (s, 2H), 4.13 (q, 2H, J=6.6. Hz), 3.84 (s, 3H), 2.78 (t, 2H, J=6.6 Hz), 2.55 (m, 4H), 1.64 (m, 4H), 1.35 (m, 2H)

EXAMPLE 112

2,2-dimethyl-propionic acid 11-[4-(2-diethylamino-ethoxy)-benzyl]-6,11-dihydro-5-thia-11-aza-benzo[a]fluoren-8-yl ester

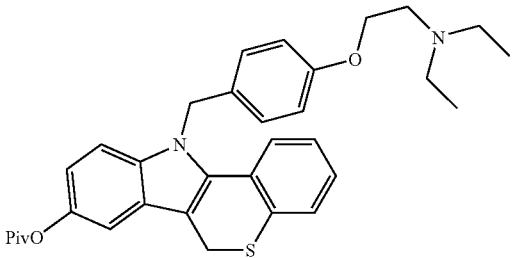

PivCl (15 uL, 0.120 mmol, 1.1 eq.) and pyridine (11 μL, 0.131 mmol, 1.2 eq.) along with a few drops of DMF were added to a mixture of 11-[4-2(diethylamino-ethoxy)-benzyl]-6,11-dihydro-5-thia-11-aza-benzo[a]fluren-8-ol (50 mg, 0.109 mmol) in CH$_2$Cl$_2$ (2 mL). The reaction mixture was partitioned between saturated NaHCO$_3$ aqueous solution and CH$_2$Cl$_2$, the aqueous layer was extracted with CH$_2$Cl$_2$ and the organic layers were dried and concentrated to yield crude product. The crude product was purified by flash chromatograph to yield the title compound as a brown solid.

MS (m/z): MH+ (543), MH− (541)

$^1$H NMR (CD$_3$OD) δ 7.44-6.74 (m, 11H), 5.41 (2H), 4.01 (t, 2H, J=6.5 Hz), 3.29 (s, 2H), 2.86 (t, 2H, J=6.5 Hz), 2.62 (q, 4H, J=6.5 Hz), 1.38 (s, 9H), 1.05 (t, J=6.8 Hz, 6H)

EXAMPLE 113

8-(tert-butyl-dimethyl-silanyloxy)-11-[4-(2-piperidin-1-yl-ethoxy)-benzyl]-6,11-dihydro-5-thia-11-aza-benzo[a]fluorine and 11-[4-(2-piperidin-1-yl-ethoxy)-benzyl]-6,11-dihydro-5-thia-11-aza-benzo[a]fluoren-8-ol

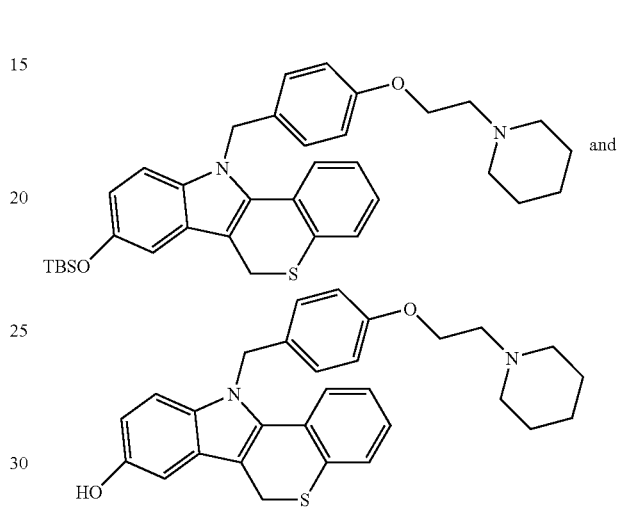

NaH (60%, 144 mg, 1.317 mmoL) was added into 8-(tert-butyl-dimethyl-silanyloxy)-6,11-dihydro-5-thia-11-aza-benzo[a]fluorene (440 mg, 1.197 mmoL) in DMF (5 mL) at 0° C. After 10 minutes, 1-[2-(4-chloromethyl-phenoxy)-ethyl]-piperidine (382 mg, 1.317 mmoL) was added dropwise into the reaction at 0° C. The reaction mixture was slowly warmed to room temperature over 2 hours. The reaction mixture was then partitioned between EtOAc and saturated NH$_4$Cl. The aqueous phase was extracted two times with EtOAc. The organic layers from the two extractions were combined, washed with water, brine, dried over anhydrous Na$_2$SO$_4$, filtered and concentrated to yield a brown oil. The crude material (the oil) was then purified by column chromatography (silica gel, first EtOAc then CH$_2$Cl$_2$:MeOH 4:1 as eluent) to yield 8-(tert-butyl-dimethyl-silanyloxy)-11-[4-(2-piperidin-1-yl-ethoxy)-benzyl]-6,11-dihydro-5-thia-11-aza-benzo[a]fluorine as a pale foam and 11-[4-(2-piperidin-1-yl-ethoxy)-benzyl]-6,11-dihydro-5-thia-11-aza-benzo[a]fluoren-8-ol as a yellow solid.

8-(tert-butyl-dimethyl-silanyloxy)-11-[4-(2-piperidin-1-yl-ethoxy)-benzyl]-6,11-dihydro-5-thia-11-aza-benzo[a]fluorine $^1$H NMR (CDCl$_3$) δ 7.28~6.52 (m, 11H), 5.16 (s, 2H), 3.88 (t, J=10.2 Hz, 2H), 2.55 (t, J=10.2 Hz, 2H), 2.31 (m, 4H), 1.41 (m, 4H), 1.22 (m, 2H), 0.81 (s, 9H), 0.03 (s, 6H).

MS (m/z): MH+, 585, MNa+, 607.

11-[4-(2-piperidin-1-yl-ethoxy)-benzyl]-6,11-dihydro-5-thia-11-aza-benzo[a]fluoren-8-ol $^1$H NMR (CDCl$_3$) δ 7.42~6.72 (m, 12H), 5.32 (s, 2H), 4.15 (t, J=10.5 Hz, 2H), 4.05 (s, 2H0, 2.85 (t, J=10.5 Hz, 2H), 2.60 (m, 4H), 1.65 (m, 4H), 1.44 (m, 2H).

MS (m/z): MH+, 471.

EXAMPLE 114

(2-{4-[8-(tert-Butyl-dimethyl-silanyloxy)-6H-5-thia-11-aza-benzo[a]fluoren-11-ylmethyl]-phenoxy}-ethyl)-diethyl-amine and 11-[4-(2-Diethylamino-ethoxy)-benzyl]-6,11-dihydro-5-thia-11-aza-benzo[a]fluoren-8-ol

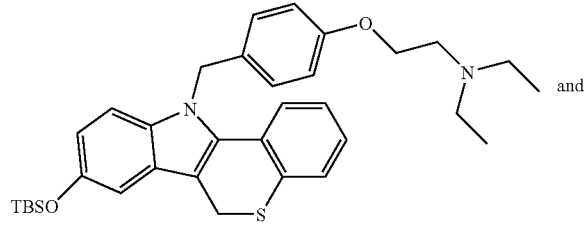

Following the procedure described in Example 113, using 8-(tert-butyl-dimethyl-silanyloxy)-6,11-dihydro-5-thia-11-aza-benzo[a]fluorene (490 mg, 1.33 mmoL) and [2-(4-chloromethyl-phenoxy)-ethyl]-diethyl-amine hydrochloride salt (370 mg, 1.33 mmoL) as the starting material, (2-{4-[8-(tert-Butyl-dimethyl-silanyloxy)-6H-5-thia-11-aza-benzo[a]fluoren-11-yl methyl]-phenoxy}-ethyl)-diethyl-amine was prepared as a pale foam and 11-[4-(2-Diethylamino-ethoxy)-benzyl]-6,11-dihydro-5-thia-11-aza-benzo[a]fluoren-8-ol was prepared as a yellow solid.

(2-{4-[8-(tert-Butyl-dimethyl-silanyloxy)-6H-5-thia-11-aza-benzo[a]fluoren-11-ylmethyl]-phenoxy}-ethyl)-diethyl-amine $^1$H NMR (CDCl$_3$) δ 7.25~6.48 (m, 11H), 5.15 (s, 2H), 3.85 (t, J=8.5 Hz, 2H), 3.84 (s, 2H), 2.73 (t, J=8.5 Hz, 2H), 2.45 (t, J=12.5 Hz, 2H), 0.88 (t, J=12.5 Hz, 2H), 0.81 (s, 9H), 0.08 (s, 6H).

MS (m/z): MH+, 573.

11-[4-(2-Diethylamino-ethoxy)-benzyl]-6,11-dihydro-5-thia-11-aza-benzo[a]fluoren-8-ol $^1$H NMR (CDCl$_3$) δ 7.45~6.68 (m, 12H), 5.30 (s, 2H), 4.10 (t, J=10.5 Hz, 2H) 4.05 (s, 2H) 2.98 (t, J=10.5 Hz, 2H), 2.70 (m, J=12.5 Hz, 4H), 1.12 (t, J=12.5 Hz, 6H).

MS (m/z): MH+, 459.

EXAMPLE 115

2,2-dimethyl-propionic acid 11-[4-(2-diethylamino-ethoxy)-benzyl]-6,11-dihydro-5-thia-aza-benzo[a] fluoren-8-yl ester

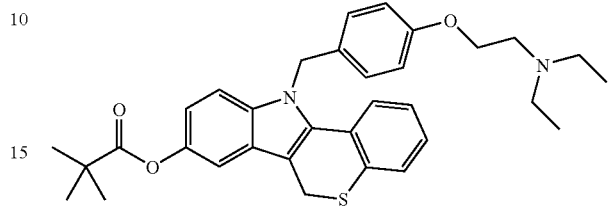

11-[4-(2-Diethylamino-ethoxy)-benzyl]-6,11-dihydro-5-thia-11-aza-benzo[a]fluoren-8-ol (50 mg, 0.109 mmoL) in CH$_2$Cl$_2$ (1 mL) was treated with pyridine (0.011 mL, 0.131 mmoL) followed by PivCl (0.015 mL, 0.120 mmoL) at 0° C. The reaction mixture was slowly warmed to room temperature over 2 hours. The reaction mixture was then partitioned between CH$_2$Cl$_2$ and saturated NH$_4$Cl. The aqueous phase was extracted two times with CH$_2$Cl$_2$. The organic layer from each extraction was combined, washed with water, brine, dried over anhydrous Na$_2$SO$_4$, filtered and concentrated to yield a brown oil. The crude material (the oil) was then purified by column chromatography (silica gel, CH$_2$Cl$_2$: MeON 4:1 as eluent) to yield the title compound as a pale foam.

$^1$H NMR (CDCl$_3$) δ 7.52~6.78 (m, 11H), 5.25 (s, 2H), 4.15 (t, J=10.5 Hz, 2H), 4.00 (s, 2H), 2.85 (t, J=10.5 Hz, 2H), 2.60 (m, J=12.5 Hz, 4H), 1.21 (s, 9H), 1.08 (t, J=12.5 Hz, 6H).

MS (m/z): MH+, 544.

EXAMPLE 116

8-methoxy-11-methyl-6,11-dihydro-5-thia-11-aza-benzo[a]fluorene 5,5-dioxide

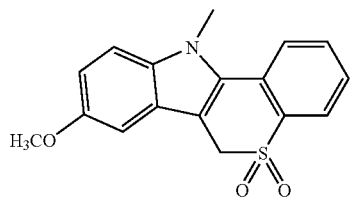

To a solution of 8-methoxy-11-methyl-6,11-dihydro-5-thia-11-aza-benzo[a]fluorene in MeOH (3 mL) and H$_2$O (5 mL) was added OXONE (1.68 g, 2.74 mmol). The reaction mixture was stirred overnight at 25° C. The solvent was removed in vacuo and the residue was then partitioned between saturated NaHCO$_3$ aqueous solution and CH$_2$Cl$_2$, the aqueous layer was extracted with CH$_2$Cl$_2$ and the organic layers were dried and concentrated to yield crude product. The crude product was then purified by flash chromatography to yield the title compound as a white solid.

MS (m/z): MNa+ (336)

¹H NMR (CDCl₃) δ 8.13~6.91 (m, 7H), 4.52 (s, 2H), 4.04 (s, 3H), 3.88 (s, 3H)

EXAMPLE 117

8-(tert-butyl-dimethyl-silanyloxy)-11-methyl-6,11-dihydro-5-thia-11-aza-benzo[a]fluorene 5-oxide and 11-methyl-5-oxo-6,11-dihydro-5H-5I4-thia-11-aza-benzo[a]fluoren-8-ol and 8-(tert-butyl-dimethyl-silanyloxy)-6,11-dihydro-5-thia-11-aza-benzo[a]fluorene 5,5-dioxide

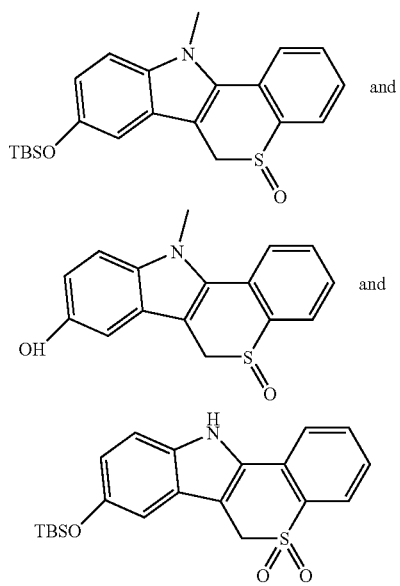

A mixture of 8-(tert-Butyl-dimethyl-silanyloxy)-11-methyl-6,11-dihydro-5-thia-11-aza-benzo[a]fluorene (490 mg, 1.286 mmol), as prepared in Example 45, and OXONE (791 mg, 1.286 mmol) in MeOH (2 mL), H₂O (2 mL) and THF (2 mL) was stirred at 25° C. After the solvent was removed in vacuo, the residue was partitioned between saturated NaHCO₃ aqueous solution and CH₂Cl₂, the aqueous layer was extracted with CH₂Cl₂ and the organic layers were dried and concentrated to yield crude product. The crude product was purified by chromatography to yield 8-(tert-butyl-dimethyl-silanyloxy)-11-methyl-6,11-dihydro-5-thia-11-aza-benzo[a]fluorene 5-oxide as a white solid, 11-methyl-5-oxo-6,11-dihydro-5H-5I4-thia-11-aza-benzo[a]fluoren-8-ol as a pale solid, and 8-(tert-butyl-dimethyl-silanyloxy)-6,11-dihydro-5-thia-11-aza-benzo[a]fluorene 5,5-dioxide as a white solid respectively.

8-(tert-butyl-dimethyl-silanyloxy)-11-methyl-6,11-dihydro-5-thia-11-aza-benzo[a]fluorene 5-oxide MS (m/z): MH⁺ (398), MNa⁺ (420)

¹H NMR (CDCl₃) δ 7.79-7.88 (m, 7H), 4.34 (d, 1H, J=13.2 Hz), 4.21 (d, 1H, J=13.1 Hz), 3.89 (s, 3H), 1.04 (s, 9H), 0.21 (s, 6H)

11-methyl-5-oxo-6,11-dihydro-5H-5I4-thia-11-aza-benzo[a]fluoren-8-ol

MS (m/z): MNa⁺ (306), MH⁻ (282)

¹H NMR (CDCl₃) δ 8.04-6.85 (m, 7H), 4.57 (s, 2H), 4.03 (s, 3H).

8-(tert-butyl-dimethyl-silanyloxy)-6,11-dihydro-5-thia-11-aza-benzo[a]fluorene 5,5-dioxide MS (m/z): MH⁺ (414), MNa⁺ (436)

¹H NMR (CDCl₃) δ 8.13-6.83 (m, 7H), 4.46 (s, 2H), 3.98 (s, 3H), 1.05 (s, 9H), 0.22 (s, 6H)

EXAMPLE 118

8-methoxy-6,11-dihydro-5-thia-11-aza-benzo[a]fluorene 5-oxide

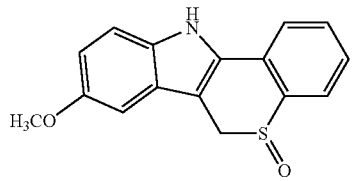

8-Methoxy-6,11-dihydro-5-thia-11-aza-benzo[a]fluorene (79 mg, 0.281 mmoL) in DMF (5 mL) was treated with KO-t-Bu (1.0 M in THF, 0.48 mL, 0.48 mmoL) under a flow of O₂ for 6 hours. The reaction mixture was then partitioned between water and EtOAc. The EtOAc layer was washed with saturated NH₄Cl, water, brine, dried over anhydrous Na₂SO₄, filtered and concentrated to yield a brown oil. The crude material (the oil) was then purified by column chromatography (silica gel, CH₂Cl₂:MeOH 9:1 as eluent) to yield the title compound as a white solid.

¹H NMR (CDCl₃) δ 8.21 (br, s, 1H0, 7.85~6.88 (m, 7H), 4.25 (abq, J=10.5 Hz, 2H), 3.85 (s, 3H).

MS (m/z): MH+, 284.

EXAMPLE 119

8-methoxy-11-methyl-6,11-dihydro-5-thia-11-aza-benzo[a]fluorene 5,5-dioxide

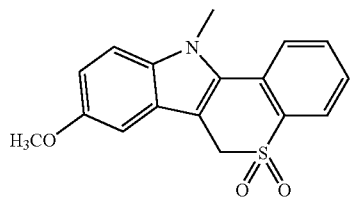

8-methoxy-6,11-dihydro-5-thia-11-aza-benzo[a]fluorene (257 mg, 0.915 mmoL) in MeOH (3 mL) and water (3 mL) was treated with OXONE (2.744 mmol., 1.68 g) at room temperature. The reaction mixture was stirred for 6 hours. The solvent was removed and the residue was partitioned between EtOAc and saturated NaHCO₃. The aqueous phase was extracted two times with EtOAc. The organic layer from each extraction was combined, washed with water, brine, dried over anhydrous Na$_2$SO$_4$, filtered and concentrated to yield a brown solid. The crude material (the oil) was then purified by column chromatography (silica gel, 1:1 hexanes: EtOAc as eluent) to yield the title compound as a white solid.

$^1$H NMR (CDCl$_3$) δ 8.10~6.85 (m, 7H), 4.45 (s, 2H), 3.95 (s, 3H), 3.80 (s, 3H).

MS (m/z): MH+, 314.

EXAMPLE 120

11-methyl-5,1-dioxo-6,11-dihydro-5H-5λ$^6$-thia-11-aza-benzo[a]fluoren-8-ol

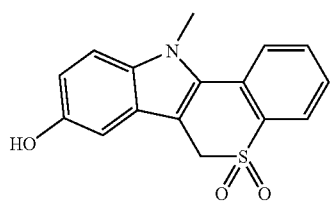

A mixture of sulfone 8-methoxy-11-methyl-6,11-dihydro-5-thia-11-aza-benzo[a]fluorene 5,5-dioxide (32 mg, 0.102 mmoL) and pyridine HCl salt (176 mg, 1.534 mmoL) was heated to 180° C. in a sealed tube for 30 minutes. The residue was dissolved in EtOAc. The reaction mixture was then filtrated through a pad of Celite to remove solids. The filtrate was partitioned between EtOAc and saturated NaHCO$_3$. The aqueous phase was extracted two times with EtOAc. The organic layer from each extraction was combined, washed with water, brine, dried over anhydrous Na$_2$SO$_4$, filtered and concentrated to yield a brown solid. The crude material (the oil) was then purified by column chromatography (silica gel, 1:1 hexanes:EtOAc as eluent) to yield the title compound as a white solid.

$^1$H NMR (d-DMSO) δ 9.05 (s, 1H), 8.00~6.82 (m, 7H, 4.82 (s, 2H), 4.05 (s, 3H).

MS (m/z): MH+, 298.

EXAMPLE 121

8-methoxy-6,11-dihydro-5-oxa-11-aza-benzo[a]fluoren-6-ol

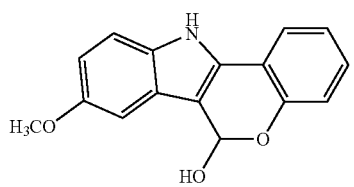

8-methoxy-6,11-dihydro-5-oxa-11-aza-benzo[a]fluorene (300 mg, 1.194 mmoL) in DMF (5 mL) was treated with KO-t-Bu (1.0 M in THF, 2.0 mL, 2.0 mmoL) under a flow of O$_2$ for 6 hours. The reaction mixture was then partitioned between water and EtOAc. The EtOAc layer was washed with saturated NH$_4$Cl, water, brine, dried over anhydrous Na$_2$SO$_4$, filtered and concentrated to yield a brown oil. The crude material was then purified by column chromatography (silica gel, hexanes:EtOAc 9:1 as eluent) to yield the title compound as a white solid.

$^1$H NMR (CDCl$_3$) δ 9.90 (s, 1H), 9.75 (br, s, 1H), 7.82~6.85 (m, 7H), 3.82 (s, 3H).

MS (m/z): MH+, 268.

EXAMPLE 122

8-methoxy-11-methyl-6,11-dihydro-5-thia-11-aza-benzo[a]fluorene 5 oxide

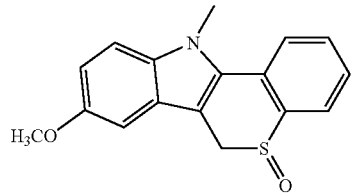

A solution of 8-methoxy-11-methyl-6,11-dihydro-5-thia-11-aza-benzo[a]fluorene 5-oxide (442 mg, 1.573 mmoL) in MeOH (3 mL) and water (3 mL) was treated with OXONE (1.573 mmol., 967 mg) at room temperature. The reaction mixture was then stirred for 6 hours. The solvent was removed and the residue was partitioned between EtOAc and saturated NaHCO$_3$. The aqueous phase was extracted two times with EtOAc. The organic layer from the two exactions was combined washed with water, brine, dried over anhydrous Na$_2$SO$_4$, filtered and concentrated to yield a brown solid. The crude material (the oil) was then purified by column chromatography (silica gel, 1:1 hexanes:EtOAc as eluent) to yield the title compound as a white solid.

$^1$H NMR (CDCl$_3$) δ 7.98~6.98 (m, 7H), 4.32 (abq, J=12.5 Hz, 2H), 4.00 (s, 3H), 3.92 (s, 3H).

MS (m/z): MH+, 298, MNa+, 320.

EXAMPLE 123

2,3-Dihydro-thiopyrano[2,3-b]pyridin-4-one

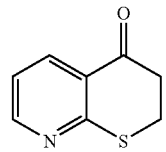

Following the procedure described in Da Settimo, Antonio; Marini, Anna Maria; Primofiore, Giampaolo; Da Settimo, Federico; Salerno, Silvia; La Motta, Concettina; Pardi, Gianluca; Ferrarini, Pier Luigi; Mori, Claudio *Journal of Heterocyclic Chemistry* 2000, 37, 379-382, the title compound was prepared as a colorless oil.

EXAMPLE 124

8-methoxy-6,11-dihydro-5-thia-4,11-diaza-benzo[a]fluorene

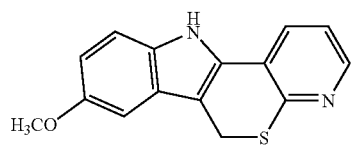

A mixture of 2,3-dihydro-thiopyrano[2,3-b]pyridin-4-one (2.24 g, 13.6 mmoL) and 4-methoxy-phenylhydrazine HCl salt (2.60 g, 14.9 mmoL) in EtOH (10 mL) was refluxed for 5 hours. The reaction mixture was cooled and filtrated through a pad of Celite to remove any solids in the mixture. The solvent was removed in vacuo. The remaining residue was partitioned between EtOAc and saturated NaHCO$_3$. The aqueous phase was extracted two times with EtOAc. The organic layer of each extraction was washed with water, brine, dried over anhydrous Na$_2$SO$_4$, filtered and concentrated to yield a brown oil. The crude material (the oil) was then purified by column chromatography (silica gel, hexanes:EtOAc1:1 as eluent) to yield the title compound as a pale solid.

$^1$H NMR (CDCl$_3$) δ 8.05 (br, s, 1H), 7.20~6.55 (m, 7H), 3.78 (s, 2H), 3.60 (s, 3H).

MS (m/z): MH+, 269.

EXAMPLE 125

8-methoxy-11-methyl-6,11-dihydro-5-thia-4,11-diaza-benzo[a]fluorene

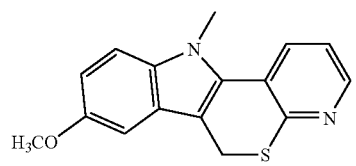

NaH (60%, 41 mg, 1.03 mmoL) was added into 8-methoxy-6,11-dihydro-5-thia-4,11-diaza-benzo[a]fluorene (250 mg, 0.933 mmoL) in DMF (3 mL) at 0° C. After 10 minutes, MeI (0.064 mL, 0.93 mmoL) was added dropwise into the reaction at 0° C. The reaction mixture was slowly warmed to room temperature over 2 hours. The reaction mixture was then partitioned between EtOAc and saturated NH$_4$Cl. The aqueous phase was extracted two times with EtOAc. The organic layer from each extraction was combined, washed with water, brine, dried over anhydrous Na$_2$SO$_4$, filtered and concentrated to yield a brown oil. The crude material (the oil) was then purified by column chromatography (silica gel, hexanes:EtOAc 1:1 as eluent) to yield the title compound as a white solid.

$^1$H NMR (CDCl$_3$) δ 8.25~6.95 (m, 6H), 4.21 (s, 2H), 3.90 (s, 3H), 3.86 (s, 3H).

MS (m/z): MH+, 283.

EXAMPLE 126

11-Methyl-6,11-dihydro-5-thia-4,11-diaza-benzo[a]fluoren-8-ol

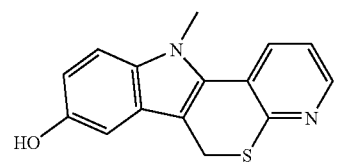

A mixture of 8-methoxy-11-methyl-6,11-dihydro-5-thia-4,11-diaza-benzo[a]fluorene (100 mg, 0.355 mmoL) and pyridine HCl salt (410 mg, 3.55 mmoL) was sealed in a tube and heated to 180° C. for 2 hours. The reaction mixture was cooled and the residue was partitioned between water and EtOAc. The EtOAc layer was washed with saturated NaHCO$_3$, water, brine, dried over anhydrous Na$_2$SO$_4$, filtered and concentrated to yield a brown oil. The crude material (the oil) was then purified by column chromatography (silica gel, hexanes:EtOAc 1:1 as eluent) to yield the title compound as a white solid.

$^1$H NMR (CDCl$_3$) δ 8.28~6.80 (m, 7H), 4.18 (s, 2H), 3.85 (s, 3H).

MS (m/z): MH+, 269.

EXAMPLE 127

1-Methyl-1,5,6,7-tetrahydro-indazol-4-one

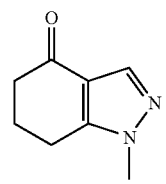

Following the procedure described in Schenone, Pietro; Mosti, Luisa; Menozzi, Giulia *Journal of Heterocyclic Chemistry* 1982, 19, 1355-61, the title compound was prepared as a colorless oil.

EXAMPLE 128

7-Methoxy-3-methyl-3,4,5,10-tetrahydro-2,3,10-triaza-cyclopenta[a]fluorene

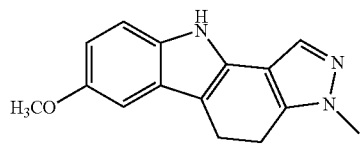

Following the procedure described in Example 124, using (2.54 g) as the starting material, the title compound was prepared as a white solid.

MS (m/z): MH+ (254)

EXAMPLE 129

7-methoxy-3,10-dimethyl-3,4,5,10-tetrahydro-2,3,10-triaza-cyclopenta[a]fluorene

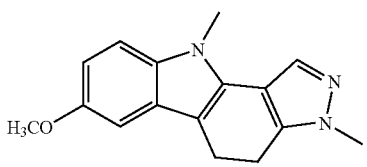

Following the procedure described in Example 125, using 7-methoxy-3,-methyl-3,4,5,10-tetrahydro-2,3,10-triaza-cyclopenta[a]fluorene (260 mg, 1.03 mmol) as the starting material, the title compound was prepared as a white solid.
MS (m/z): MH+ (268)
$^1$H NMR (DMSO-d$_6$) δ 7.71-6.59 (m, 4H), 3.79 (s, 3H), 3.75 (s, 3H), 3.72 (s, 3H), 2.89 (m, 4H)

EXAMPLE 130

7-methoxy-3,10-dimethyl-3,10-dihydro-2,3,10-triaza-cyclopenta[a]fluorene

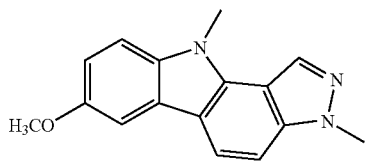

7-methoxy-3,10-dimethyl-3,4,5,10-tetrahydro-2,3,10-triaza-cyclopenta[a]fluorene (136 mg, 0.51 mmol) in DMF (2 mL) was treated with KO$_2$ (5.0 eq.) at room temperature. The reaction mixture was stirred overnight. Water was added and the reaction mixture was extracted with ethyl acetate. The organic layer was washed with brine and dried, concentrated. The crude material was purified by silica gel column to yield the title compound as a white solid.
MS (m/z): MH+ (266)
$^1$H NMR (CDCl$_3$) δ 8.32-7.09 (m, 6H), 4.18 (s, 6H), 3.96 (s, 3H)

EXAMPLE 131

3,10-dimethyl-3,10-dihydro-2,3,10-triaza-cyclopenta[a]fluoren-7-ol

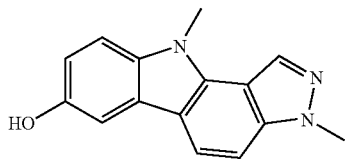

A mixture of 7-methoxy-3,10-dimethyl-3,10-dihydro-2,3,10-triaza-cyclopenta[a]fluorene (55 mg, 0.21 mmol), AlCl$_3$ (0.84 mmol, 4.0 eq.) and EtSH (0.63 mmol, 3.0 eq.) in CH$_2$Cl$_2$ (2 mL) was stirred at room temperature for 16 hours. The reaction mixture was poured into cold saturated NaHCO$_3$ solution, extracted with CH$_2$Cl$_2$, washed with brine and dried, concentrated to yield the crude product. The crude product was then purified by chromatography to yield the title compound as a white solid.
MS (m/z): MH+ (252)

EXAMPLE 132

7,8-Dihydro-6H-quinolin-5-one

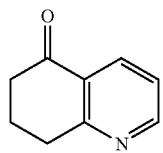

Following the procedure described in Albright, J. Donald; Du, Xuemei *Journal of Heterocyclic Chemistry* 2000, 37, 41-46, the title compound was prepared as a colorless oil.

EXAMPLE 133

8-methoxy-5,11-dihydro-6H-pyrido[3,2-a]carbazole

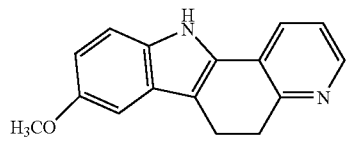

Following the procedure described in Example 124, using 7,8-dihydro-6H-quinolin-5-one (860 mg, 6.0 mmol) as the starting material, the title compound was prepared as a brown solid.
$^1$H NMR (CDCl$_3$) δ 8.20-6.75 (m, 6H), 3.80 (s, 3H), 3.15 (t, J=3.0 Hz, 2H). 3.05 (t, J=3.0 Hz, 2H)
MS (m/z): MH+ (251)

EXAMPLE 134

8-methoxy-11-methyl-5,11-dihydro-6H-pyrido[3,2-a]carbazole

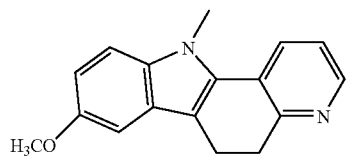

Following the procedure described in Example 125, using 8-methoxy-5,11-dihydro-6H-pyrido[3,2-a]carbazole (1.25 g, 5.0 mmol), as prepared in Example 133, as the starting material, the title compound was prepared as a white solid.
$^1$H NMR (CDCl$_3$) δ 8.35-6.85 (m, 6H), 3.90 (s, 3H), 3.85 (s, 3H), 3.20 (t, J=3.0 Hz, 2H). 3.00 (t, J=3.0 Hz, 2H)
MS (m/z): MH+ (265)

EXAMPLE 135

11-methyl-5,11-dihydro-6H-pyrido[3,2-a]carbazol-8-ol

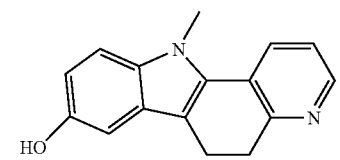

Following the procedure described in Example 126, using 8-methoxy-11-methyl-5,11-dihydro-6H-pyrido[3,2-a]carbazole (0.8 g) as the starting the material, the title compound was prepared as a brown solid,
$^1$H NMR (CDCl$_3$) δ 8.38-6.83 (m, 6H), 3.92 (s, 3H), 3.22 (t, 2H, J=6.7 Hz), 2.93 (t, 2H, J=6.7 Hz)
MS (m/z): MH+ (250)

EXAMPLE 136

7,8-Dihydro-6H-quinoxalin-5-one

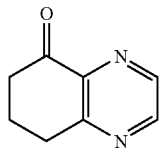

Following the procedure described in Chow, Ken; Gil, Daniel W.; Burke, James A.; Harcourt, Dale A.; Garst, Michael E.; Wheeler, Larry A.; Munk, Stephen A. PCT Int. Appl. WO 9928300 A1 19990610, the title compound was prepared as a colorless oil.

EXAMPLE 137

8-methoxy-5,11-dihydro-6H-pyrazino[2,3-a]carbazole

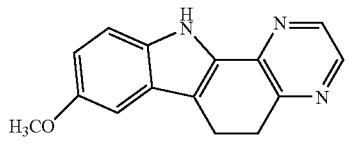

Following the procedure described in Example 124, using 7,8-dihydro-6H-quinoxalin-5-one (740 mg, 5 mmol) as the starting material, the title compound was prepared as a brown solid.

$^1$H NMR (CDCl$_3$) δ 9.15 (br. 1H), 8.20-6.90 (m, 5H), 3.85 (s, 3H), 3.35 (t, J=3.5 Hz, 2H), 3.15 (t, J=3.5 Hz, 2H)

MS (m/z): MH+ (252)

EXAMPLE 138

8-Methoxy-11-methyl-5,11-dihydro-6H-pyrido[3,2-a]carbazole

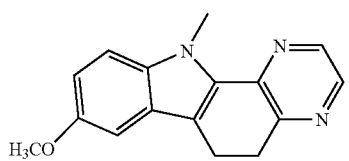

Following the procedure described in Example 125, using 8-methoxy-5,11-dihydro-6H-pyrazino[2,3-a]carbazole (500 mg, 2 mmol) as the starting material, the title compound was prepared as a pale solid.

$^1$H NMR (CDCl$_3$) δ 8.05-7.05 (m, 5H), 3.85 (s, 3H), 3.35 (t, J=3.5 Hz, 2H), 3.15 (t, J=3.5 Hz, 2H)

EXAMPLE 139

11-methyl-6,11-dihydro-5-thia-1,4,11-triaza-benzo[a]fluoren-8-ol

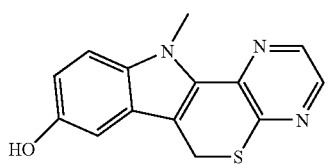

Following the procedure described in Example 126, using 8-methoxy-11-methyl-6,11-dihydro-5-thia-11-aza-benzo[a]fluorene (260 mg, 1 mmol) as the starting material, the title compound was prepared as a brown solid.

$^1$H NMR (CDCl3) δ 9.75 (br, 1H), 8.15-7.25 (m, 3H), 3.85 (s, 3H), 3.35 (t, J=3 Hz, 2H), 3.15 (t, J=3 Hz, 2H)

Ms (m/z): MH+ (252), MH− (250)

EXAMPLE 140

[2-(8-methoxy-5,6-dihydro-pyrido[3,2-a]carbazol-11-yl-ethyl]-dimethyl-amine

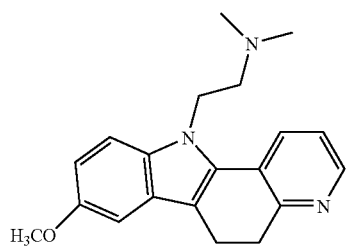

Following the procedure described in Example 125, using 8-methoxy-5,11-dihydro-6H-pyrido[3,2-a]carbazole (1.0 g, 4.0 mmol) and ClCH$_2$CH$_2$N(Me)$_2$ (1.0 eq.) as the starting material, the title compound was prepared as a brown solid.

$^1$H NMR (CDCl3) δ 8.40-6.85 (m, 6H), 4.40 (t, J=3 Hz, 2H), 3.85 (s, 3H), 3.20 (t, J=3 Hz, 2H), 2.95 (t, J=3 Hz, 2H), 2.75 (t, J=3 Hz, 2H), 2.35 (s, 6H)

MS (m/z): MH+ (323)

EXAMPLE 141

11-(2-dimethylamino-ethyl-5,11-dihydro-6H-pyrido[3,2-a] carbazol-9-ol

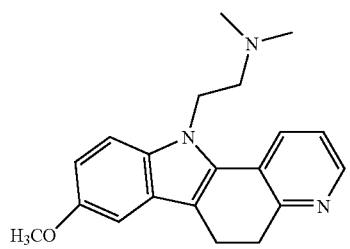

Following the procedure described in Example 126, using [2-(8-methoxy-5,6-dihydro-pyrido[3,2-a]carbazol-11-yl-ethyl]-dimethyl-amine (1.6 g, 5 mmol) as the starting material, the title compound was prepared as a brown solid.

$^1$H NMR (CDCl3) δ 8.40-6.85 (m, 6H), 4.40 (t, J=3 Hz, 2H), 3.45 (s, 1H), 3.20 (t, J=3 Hz, 2H), 2.95 (t, J=3 Hz, 2H), 2.75 (t, J=3 Hz, 2H), 2.35 (s, 6H)

MS (m/z): MH+ (309)

EXAMPLE 142

9-methoxy-5,11-dihydro-6H-pyrido[3,2-a]carbazole

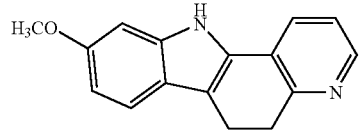

Following the procedure described in Example 124, using 7,8-dihydro-6H-quinolin-5-one (1.48 g, 10.0 mmol) as the starting material, the title compound was prepared as a brown solid.

$^1$H NMR (CDCl$_3$) δ 8.40 (br, 1H), 8.30-6.80 (m, 6H), 3.80 (s, 3H), 3.15 (t, J=3.0 Hz, 2H). 3.05 (t, J=3.0 Hz, 2H)
MS (m/z): MH+ (251)

EXAMPLE 143

9-methoxy-11-methyl-5,11-dihydro-6H-pyrido[3,2-a]carbazole

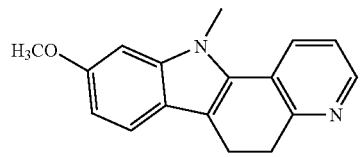

Following the procedure described in Example 125, using 9-methoxy-5,11-dihydro-6H-pyrido[3,2-a]carbazole (1.40 g, 5.6 mmol) as the starting material, the title compound was prepared as a pale yellow solid.

$^1$H NMR (CDCl$_3$) δ 8.35-6.85 (m, 6H), 3.90 (s, 3H), 3.85 (s, 3H), 3.20 (t, J=3.0 Hz, 2H). 3.00 (t, J=3.0 Hz, 2H)
MS (m/z): MH+ (265)

EXAMPLE 144

11-Methyl-5,11-dihydro-6H-pyrido[3,2-a]carbazol-9-ol

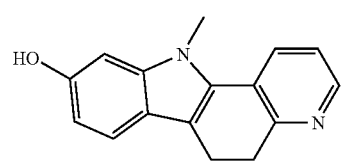

Following the procedure described in Example 126, using 9-methoxy-11-methyl-5,11-dihydro-6H-pyrido[3,2-a]carbazole (320 mg, 1.2 mmol) as the starting material, the title compound was prepared as a brown solid.

1H NMR (MeOH) δ 8.20-6.65 (m, 6H), 3.30 (s, 3H), 3.15 (t, J=3 Hz, 2H), 2.95 (t, J=3 Hz, 2H)
MS (m/z): MH+ (251), MH− (249)

EXAMPLE 145

7-methoxy-5,10-dihydro-4H-thieno[3,2-a]carbazole

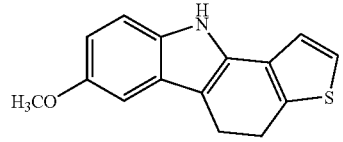

Following the procedure described in Example 124, using 4-keto-4,5,6,7-tetrahydrothianaphthlene (760 mg, 5.0 mmol) as the starting material, the title compound was prepared as a brown solid.

1H NMR (CDCl3) δ 7.90 (br, 1H), 7.25-6.80 (m, 5H), 3.85 (s, 3H), 3.10 (m, 4H)
Ms (m/z): MH+ (256)

EXAMPLE 146

7-Methoxy-10-methyl-5,10-dihydro-4H-thieno[3,2-a]carbazole

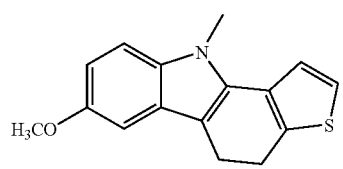

Following the procedure described in Example 125, using 7-methoxy-5,10-dihydro-4H-thieno[3,2-a]carbazole (800 mg, 3.1 mmol) as the starting material, the title compound was prepared as a brown solid.
Ms (m/z): MH+ (270)

EXAMPLE 147

10-methyl-5,10-dihydro-4H-thieno[3,2-a]carbazol-7-ol

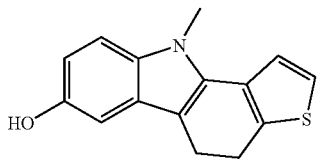

Following the same procedure described in Example 126, using 7-methoxy-10-methyl-5,10-dihydro-4H-thieno[3,2-a]carbazoleas (525 mg), the title compound was prepared as a brown solid.

$^1$H NMR (CDCl$_3$) δ 7.72 (d, J=7.5 Hz, 1H), 7.32 (d, J=1.5 Hz, 1H), 7.22 (d, J=7.5, 1H), 6.95 (m, 2H), 3.92 (s, 3H), 3.82 (t, J=8.5 Hz, 2H), 3.45 (t, J=8.5 Hz, 2H)
MS (m/z): MH+ (256).

EXAMPLE 148

7-methoxy-3,4,5,10-tetrahydro-pyrrolo[3,2-a]carbazole

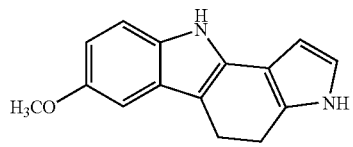

Following the procedure described in Example 124, using 1,5,6,7-tetrahydro-indol-4-one (675 mg, 5.0 mmol) as the starting material, the title compound was prepared as a brown solid.

1H NMR (CDCl3) δ 7.25-6.60 (m, 5H), 3.85 (s, 3H), 3.00 (t, J=5 Hz, 2H), 2.80 (t, J=5 Hz, 2H)
Ms (m/z): MH+ (237)

EXAMPLE 149

3,10-dimethyl-3,4,5,10-tetrahydro-pyrrolo[3,2-a]carbazol-7-ol

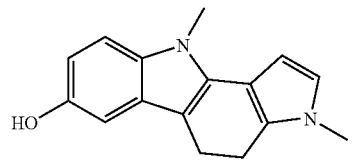

Following the procedure described in Example 125, using 7-methoxy-3,4,5,10-tetrahydro-pyrrolo[3,2-a]carbazole (474 mg, 2.0 mmol) as the starting material, 7-methoxy-3,10-dimethyl-3,4,5,10-tetrahydro-pyrrolo[3,2-a]carbazole as prepared as a crude product. The crude product was then recated according to the procedure as described in Example 126 to yield the title compound as a brown solid.

$^1$H NMR (CDCl$_3$) δ 7.72 (d, J=7.5 Hz, 1H), 7.40 (d, J=1.5 Hz, 1H), 7.22 (d, J=7.5, 1H), 6.85 (m, 2H), 4.05 (s, 3H), 3.02 (t, J=8.5 Hz, 2H), 2.85 (t, J=8.5 Hz, 2H)
MS (m/z): MH+ (280)

EXAMPLE 150

11-Ethyl-6,11-dihydro-5-thia-11-aza-benzo[a]fluoren-8-ol

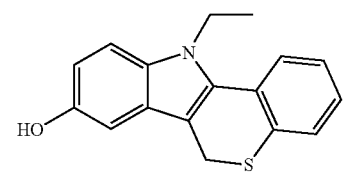

Following the procedure described in Example 58, using 11-ethyl-8-methoxy-6,11-dihydro-5-thia-11-aza-benzo[a]fluorene (756 mg, 2.56 mmol), as the starting material, the title compound was prepared as a brown solid.

MS (m/z): MH+ (282), MH− (280)
$^1$H NMR (CDCl$_3$) δ 7.96-6.82 (m, 7H), 4.28 (q, J=6.6 Hz, 2H), 4.00 (s, 2H), 1.52 (t, J=6.6 Hz, 3H)

EXAMPLE 151

6-[1,4-dithia]-8a-methyl-3,4,6,7,8,8a-hexahydro-2H-naphthalen-1-one

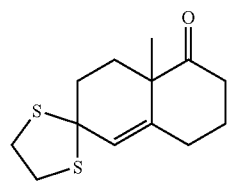

3,4,8,8a-tetrahydro-8a-methyl-1,6 (2H, 7H)-naphthalene-dione (1.78 g, 10.0 mmol) was mixed with 1,2-Bis-trimethylsilanylsulfanyl-ethane (2.38 g, 10.0 mmol) in ether (10.0 ml). The reaction was stirred at room temperature overnight and then quenched with H$_2$O, extracted with ethyl acetate. Crude product was purified on column chromatography (Hex: ethyl acetate, 1:1) to yield the title compound as a white solid.

$^1$H NMR (CDCl$_3$) δ 5.65 (s, 1H), 3.35 (m, 2H), 3.25- (m, 1H), 2.70-2.50 (m, 2H), 2.35-2.00 (m, 7H), 1.75-1.60 (m, 2H), 1.25 (s, 3H)
MS (m/z): M+Na (277)

EXAMPLE 152

3-[1,4-dithia]-8-Methoxy-11b-methyl-2,5,6,11,11b-hexahydro-1H-benzo[a]carbazole

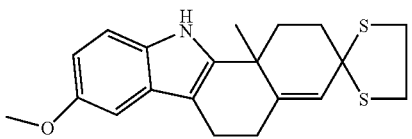

Following the procedure described in Example 4, using 4-methoxy-hydrazine 6-[1,4-dithia]-8a-methyl-3,4,6,7,8,8a-hexahydro-2H-naphthalen-1-one (1.27 g, 5.0 mmol) as the starting material, the title compound was prepared as a brown solid.

$^1$H NMR (CDCl$_3$) δ 7.60 (br, 1H), 7.35-6.70 (m, 3H), 5.70 (s, 1H), 3.80 (s, 3H), 3.40-2.30 (m, 12H), 1.40 (s, 3H)
MS (m/z): MH+ (358)

EXAMPLE 153

3-[1,4-dithia]-8-Methoxy-11,11b-methyl-2,5,6,11,11b-hexahydro-1H-benzo[a]carbazole

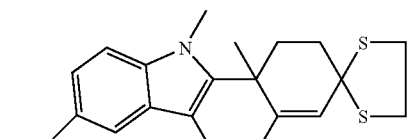

Following the procedure described in Example 33, using 3-[1,4-dithia]-8-methoxy-11b-methyl-2,5,6,11,11b-hexahydro-1H-benzo[a]carbazole from Example 152 (700 mg, 2 mmol) as the starting material, the title compound was prepared as a brown solid, $^1$H NMR (CDCl$_3$) δ 7.35-6.70 (m, 3H), 5.70 (s, 1H), 3.80 (s, 3H), 3.75 (s, 3H), 3.40-2.10 (m, 12H), 1.40 (s, 3H)

MS (m/z): MH+ (372)

EXAMPLE 154

8-methoxy-11,11b-dimethyl-1,2,5,6,11,11b-hexahydro-benzo[a]carbazol-3-one

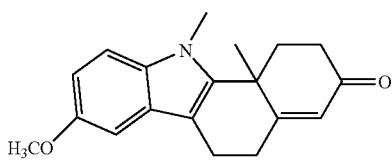

A mixture of 3-[1,4-dithia]-8-methoxy-11,11b-methyl-2,5,6,11b-hexahydro-1H-benzo[a]carbazole (700 mg, 1.9 mmol) in THF (20 ml) and water (3.0 ml) was mixed with CaCO$_3$ (0.33 g, 3 mmol) and Hg(ClO$_4$)$_2$(1.5 ml, 2.0 M solution). After 10 min at 25° C., the reaction mixture turned a black color. The reaction mixture was filtered though a pad of Celite. The solvent was removed and the residue was partitioned between EtOAc and water. The organic layer was washed with brine, dried and concentrated. The crude product was purified by chromatography to yield the title compound as a white solid.

$^1$H NMR (CDCl$_3$) δ 7.60 (br, 1H), 7.35-6.75 (m, 3H), 5.90 (s, 1H), 3.80 (s, 3H), 3.75 (s, 3H), 3.00-2.20 (m, 8H), 1.65 (s, 3H)

MS (m/z): MH+ (281)

EXAMPLE 155

8-hydroxy-11,11b-dimethyl-1,2,5,6,11,11b-hexahydro-benzo[a]carbazol-3-one

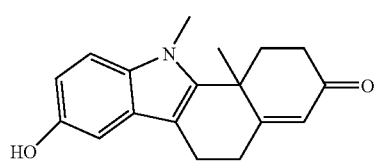

Following the procedure described in Example 58, using 8-methoxy-11,11b-dimethyl-1,2,5,6,11,11b-hexahydro-benzo[a]carbazol-3-one (500 mg, 1.8 mmol), as prepared in Example 154, as starting material, the title compound was prepared as a brown solid.

$^1$H NMR (CDCl3) δ 7.12-6.77 (m, 3H), 5.95 (s, 1H), 4.70 (br, 1H), 3.78 (s, 3H), 2.95 (m, 1H), 2.79-2.52 (m, 6H), 2.21 (m, 1H), 1.70 (s, 3H)

Ms (m/z): MH+ (267)

EXAMPLE 156

3-[1,4-dithia]-9-methoxy-11b-methyl-2,3,5,6,11,11b-hexahydro-1H-benzo[a]carbazole

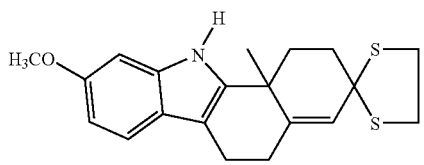

Following the procedure described in Example 4, using 3-methoxy-hydrazine and 6-[1,4-dithia]-8a-methyl-3,4,6,7,8,8a-hexahydro-2H-naphthalen-1-one (0.8 g, 3.2 mmol) as the starting materials, the title compound was prepared as a brown solid.

$^1$H NMR (CDCl$_3$) δ 7.60 (br, 1H), 7.40-6.70 (m, 3H), 5.70 (s, 1H), 3.80 (s, 3H), 3.40-2.30 (m, 12H), 1.40 (s, 3H)

MS (m/z): MH+ (358)

EXAMPLE 157

3-[1,4-dithia]-9-methoxy-11,11b-dimethyl-1,2,5,6,11,11b-hexahydro-benzo[a]carbazole

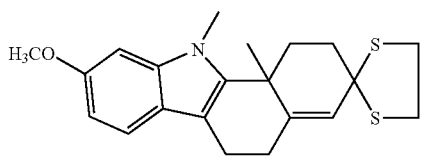

Following the procedure described in Example 33, using 3-[1,4-dithia]-9-methoxy-11b-methyl-2,3,5,6,11,11b-hexahydro-1H-benzo[a]carbazole from Example 168 (700 mg, 2 mmol) as the starting material, the title compound was prepared as a white solid.

$^1$H NMR (CDCl$_3$) δ 7.35-6.70 (m, 3H), 5.70 (s, 1H), 3.80 (s, 3H), 3.75 (s, 3H), 3.40-2.30 (m, 12H), 1.45 (s, 3H)

MS (m/z): MH+ (372)

EXAMPLE 158

9-methoxy-11,11b-dimethyl-1,2,5,6,11,11b-hexahydro-benzo[a]carbazol-3-one

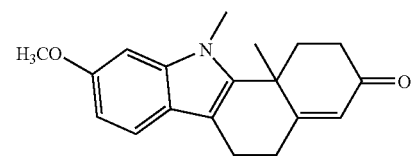

Following the procedure described in Example 154, using 3-[1,4-dithia]-9-methoxy-11,11b-dimethyl-1,2,5,6,11,11b-hexahydro-benzo[a]carbazole from Example 157 (700 mg, 1.9 mmol) as the starting material, the title compound was prepared as a white solid.

<sup>1</sup>H NMR (CDCl₃) δ 7.45-6.75 (m, 3H), 5.90 (s, 1H), 3.80 (s, 3H), 3.75 (s, 3H), 3.00-2.20 (m, 8H), 1.65 (s, 3H)
MS (m/z): MH+ (281)

EXAMPLE 159

9-hydroxy-11,11b-dimethyl-1,2,5,6,11,11b-hexahydro-benzo[a]carbazol-3-one

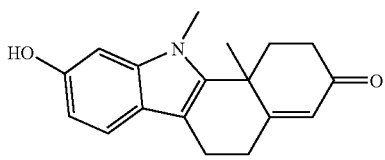

Following the procedure described in Example 58, using 9-methoxy-11,11b-dimethyl-1,2,5,6,11,11b-hexahydro-benzo[a]carbazol-3-one (150 mg, 0.5 mmol), as prepared in Example 158 as the starting material, the title compound was prepared as a white solid.
1H NMR (CDCl3) δ 7.10-6.70 (m, 3H), 5.90 (s, 1H), 4.80 (br, 1H), 3.75 (s, 3H), 2.95 (m, 1H), 2.70-2.50 (m, 6H), 2.20 (m, 1H), 1.70 (s, 3H)
Ms (m/z): MH+ (267)

EXAMPLE 160

1,4a-dimethyl-4,4a,6,7-tetrahydro-1H,3H-quinoline-2,5-dione

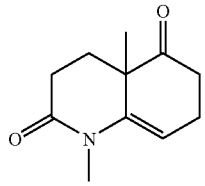

1,4a-dimethyl-4,4a,6,7-tetrahydro-1H,3H-quinoline-2,5-dione was prepared as described in WO 00/06167(PCT/US99/16829).

EXAMPLE 161

8-methoxy-4,11b-dimethyl-1,2,4,6,11,11b-hexahydro-pyrido[3,2-a]carbazol-3-one

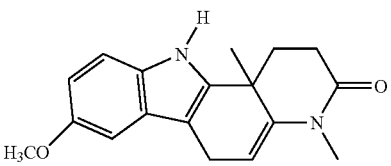

Following the procedure described in Example 4, using 1,4a-dimethyl-4,4a,6,7-tetrahydro-1H,3H-quinoline-2,5-dione (1.0 g, 5.2 mmol) as the starting material, the title compound was prepared as a white solid.

1H NMR (CDCl3) δ 7.25-6.80 (m, 3H), 5.50 (t, J=1.5 Hz, 1H), 3.85 (s, 3H), 3.50 (m, 2H), 3.35 (s, 3H), 2.70 (m, 2H), 2,10 (m, 2H), 1.50 (s, 3H)
Ms (m/z): MH+ (296)

EXAMPLE 162

8-methoxy-4,11,11b-trimethyl-1,2,4,6,11,11b-hexahydro-pyrido[3,2-a]carbazol-3-one

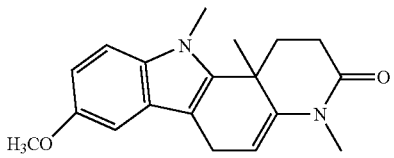

Following the procedure described in Example 33, using 8-methoxy-4,11b-dimethyl-1,2,4,6,11,11b-hexahydro-pyrido[3,2-a]carbazol-3-one (1.0 g, 3.1 mmol) as the starting material, the title compound was prepared as a white solid.
1H NMR (CDCl3) δ 7.25-6.85 (m, 3H), 5.50 (t, J=1.5 Hz, 1H), 3.85 (s, 3H), 3.75 (s, 3H), 3.50 (m, 2H), 3.35 (s, 3H), 2.70 (m, 2H), 2.10-2.35 (m, 2H), 1.50 (s, 3H)
Ms (m/z): MH+ (311)

EXAMPLE 163

8-hydroxy-4,11,11b-trimethyl-1,2,4,6,11,11b-hexahydro-pyrido[3,2-a]carbazol-3-one

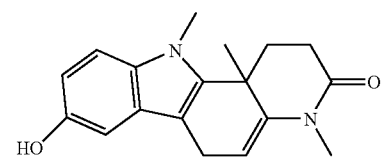

Following the procedure described in Example 58, using 8-methoxy-4,11,11b-trimethyl-1,2,4,6,11,11b-hexahydro-pyrido[3,2-a]carbazol-3-one, as the starting material, the title compound was prepared as a white solid.
<sup>1</sup>H NMR (CDCl3) δ 7.25-6.85 (m, 3H), 5.50 (t, J=1.5 Hz, 1H), 3.80 (s, 3H), 3.50 (m, 2H), 3.20 (s, 3H), 2.70 (m, 2H), 2.10-2.05 (m, 2H), 1.50 (s, 3H)
Ms (m/z): MH+ (297)

EXAMPLE 164

11-(2-Dimethylamino-ethyl)-6,11-dihydro-5-thia-11-aza-benzo[a]fluoren-8-ol

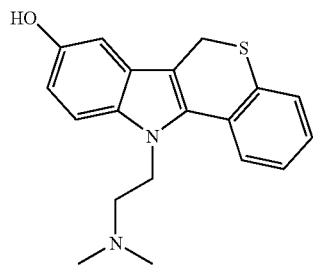

A mixture of [2-(8-methoxy-6H-5-thia-11-aza-benzo[a]fluoren-11-yl)-ethyl]-dimethyl-amine (800 mg, 2.39 mmol) and Pyridine HCl (3.01 g, 23.7 mmol, 10 eq.) was heated to 210° C. for 30 minutes. The reaction mixture was then partitioned between EtOAc and saturated NaHCO$_3$ aqueous solution. The aqueous layer was extracted three times with EtOAc. The combined organic layer was washed with brine, dried over anhydrous Na$_2$SO$_4$, filtered and concentrated to yield a crude material. The crude material was purified by silica gel (EtOAc to CH$_2$Cl$_2$:MeOH 5:1) to yield the title compound as a brown solid.

$^1$H NMR (CDCl$_3$) δ 7.75-7.01 (m, 7H), 4.54 (t, 2H, J=7.5 Hz), 4.12 (s, 2H), 2.75 (t, 2H, J=7.5 Hz), 2.38 (s, 6H); MS (m/z): MH$^+$(325), MNa$^+$(347).

EXAMPLE 165

Estrogen Receptor α Flash Plate Assay

This assay monitors binding of radiolabeled estrogen to the estrogen receptor. It is performed on a BioMek 2000 (Beckman). Plates are read in a scintillation counter (Packard Top-Count), with decreased counts an indication of binding of a compound to the receptor. The assay was run according to the procedure described by Allan, et al., *Anal. Biochem.* (1999), 275(2), 243-247.

On day one, 100 μL of Estrogen Screening Buffer (ESB, Panvera) containing 5 mM dithiothreitol (DTT, Panvera), 0.5 μg mouse anti-estrogen receptor monoclonal antibody (SRA-1010, Stressgen) and 50 ng purified human estrogen receptor α (Panvera) were added to each well of a 96 well FlashPlate Plus plate crosslinked with goat anti-mouse antibodies (NEN Life Sciences). The plate was sealed and incubated at 4° C. overnight.

On day two, each well was washed three times with 200 μL PBS, pH 7.2, at room temperature. To each well was then added 98 μL radiolabeled estrogen (0.5 nM, which equals 6 nCi for a 120 Ci/mmol batch, Amersham), diluted in ESB and 5 mM dithiothreitol (DTT). To individual wells were then added 2.5 μL test compound diluted in 30% (v/v) dimethyl sulfoxide/50 mM HEPES, pH 7.5. The wells were mixed three times by aspiration, the plate sealed and incubated at room temperature for one hour. The wells were then counted for 1 min in a TopCount scintillation counter (Packard).

EXAMPLE 166

Estrogen Receptor β Fluorescence Polarization Assay

This assay monitors binding of a fluorescent analog of estrogen (Fluormone ES2, Panvera) to the estrogen receptor. Plates are read in a fluorometer that can be set to polarization mode. A decrease in fluorescence relative to vehicle control is an indication of binding of a compound to the receptor.

It is crucial to avoid introduction of air bubbles into the reaction in each well of the 96 well plate throughout this procedure. (Bubbles on the surface of the reaction disrupt light flow, affecting the polarization reading.) However, it is also crucial to effectively mix the reaction components upon addition to the well.

On ice, a 2× standard mixture of Assay Buffer (Panvera), 10 nM DTT and 40 nM ES2 was prepared. On ice, a 2× reaction mixture of Assay Buffer (Panvera), and 20 nM hER-β (Panvera) and 40 nM ES2 was also prepared.

Dilutions of test compound were prepared in 30% (v/v) dimethyl sulfoxide/50 mM HEPES, pH 7.5. At this point, the dilutions were 40× the final required concentration.

The standard mixture at 50 μL was then added to each well. The reaction mixture at 48 μL was added to all wells. The compound dilution at 2.5 μL was added to the appropriate wells. The reaction mixtures were mixed using a manual pipette, a roll of aluminum foil adhesive cover was placed on the plate and the plate incubated at room temperature for 1 hour.

Each well on the plate was then read in an LjL Analyst with an excitation wavelength of 265 nm and an emission wavelength of 538.

EXAMPLE 167

Androgen Receptor Binding Using Rat Ventral Prostate Cytosol

Male Sprague Dawley or Wistar rats (Charles River, 200-300 g) were used for each preparation. The day before preparing the cytosol, the rats were castrated using standard surgical procedures.

The rats were euthanized by carbon dioxide asphyxiation. The rat prostates were then quickly removed and placed on ice in pre-chilled, pre-weighed 50 mL plastic tubes. No more than five prostates were placed in each tube. The tubes were then weighed and the prostate tissue wet weights calculated.

To the chilled prostate tissue was then added 1 mL/mg tissue of chilled homogenization buffer. The homogenization buffer was freshly prepared by mixing 10 mM Tris.HCl, pH 7.4, 1 mM sodium molybdate, 1.5 mM EDTA, 1 mM dithiothreitol, 10% (v/v) glycerol and 1% protease inhibitor cocktail (Sigma P 8340).

The prostate tissue was homogenized in a cold room using a pre-chilled Polytron PT3000 homogenizer (Brinkmann). Homogenization was performed at a speed setting of 20, three times for 10 sec bursts. The tubes containing the prostate tissue was kept on ice while homogenizing. The homogenate was allowed to rest on ice for 20 sec between bursts.

The homogenate was then placed into pre-chilled 3 mL polycarbonate ultracentrifuge tubes and centrifuged in the TLA-100 rotor of a TL-100 ultracentrifuge for 12 min at 100,000 rpm at 4° C. The resulting supernatant was stored in 1 mL aliquots at −80° C. until needed.

Binding to the androgen receptor was determined according to the protocol described in Example 164 using the above prepared rat cytosol.

% Inhibition was determined by testing dilutions of the test compound (usually duplicates of 10 μM) in the binding assay. Counts per well were measured and percents of inhibition determined. Androgen receptor binding IC$_{50}$s were determined by testing serial dilutions of the test compound (usually duplicate ten half-log dilutions starting at 10 μM) in the binding assay. Counts per well were measured and IC$_{50}$s determined by linear regression.

EXAMPLE 168

Progesterone Receptor Binding Assay

To a Microflour 2 Black plate (Dynex, Chantilly, Va.), PR Screening Buffer, 5 mM dithiothreitol, 40 nM human progesterone receptor ligand binding domain, and 2 nM Fluormone PL Red (all from Invitrogen, Carlsbad, Calif.) were added, along with test compound at the desired concentration. The plate was covered with aluminum foil and incubated for 1 hour at room temperature. The plate was then read on an LJL Analyst fluorescence polarization reader (Molecular Devices, Sunnyvale, Calif.).

% Inhibition was determined by testing dilutions of the test compound (usually duplicates of 10 µM) in the binding assay. Counts per well were measured and percents of inhibition determined. Progesteron receptor binding $IC_{50}s$ were determined by testing serial dilutions of the test compound (usually duplicate ten half-log dilutions starting at 10 µM) in the binding assay. Counts per well were measured and $IC_{50}s$ determined by linear regression.

EXAMPLE 169

COS-7 Whole-Cell Androgen Receptor Binding Assay, Adenovirus Transduction

Day One:

COS-7 cells were plated in 96-well plates at 20,000 cells per well, in a solution of DMEM/F12 (GIBCO) containing 10% (v/v) charcoal-treated fetal bovine serum (Hyclone) and lacking phenol red. The cells were then incubated overnight at 37° C. in 5% (v/v) humidified $CO_2$.

Day Two:

Test compound solutions were prepared by diluting the test compound in 100% (v/v) DMSO, if necessary. Each dilution yielded a solution which was 625× the final desired test concentration.

Next, 1 mL of DMEM/F12 lacking phenol red was pipetted into each of the wells of a 2-mL 96-well assay block. Then 44 µL of the 625× test compound dilutions were pipetted into each well of the assay block. The wells were carefully mixed by pipette.

In a 15 mL or 50 mL sterile centrifuge tube, a 2.5 nM dilution of tritiated methyl-trienolone in DMEM/F12 lacking phenol red ([$^3$H]R1881; Perkin-Elmer) was prepared.

In a 15 mL or 50 mL sterile centrifuge tube, a dilution in DMEM/F12 of the adenovirus AdEasy+rAR at an moi of 1:50 per well was prepared.

The medium was removed from the 96-well plates by inversion and the plates dried very briefly, inverted, on a sterile towel. As soon as possible after medium removal, 40 µL of the diluted test compound was added to each well, in duplicate. To each well was then added 40 µL of the 2.5 nM [$^3$H]R1881 and 20 µL of the diluted adenovirus. The plates were then incubated for 48 hours at 37° C. in 5% (v/v) humidified $CO_2$.

Day Four:

The medium was removed from the above incubated plates by inversion and dried. Each well was then washed with 0.35 mL of 1×PBS. The PBS was then removed from the plates by inversion and the plates dried.

To each well was then added 50 µL of 0.5% (v/v) Triton X-100 (Sigma) in 1×PBS and the plates placed on a rotary shaker for 5 min. The contents of each well were then transferred to an OptiPlate-96 (Packard) scintillation plate. To each well was then added 0.2 mL of Microscint-20 (Packard) and the wells counted on a TopCount (Packard).

Percent inhibition was determined by testing dilutions of the test compound (usually duplicates of 10 µM) in the binding assay. Counts per well were measured and percents of inhibition determined. Androgen receptor binding $IC_{50}s$ were determined by testing serial dilutions of the test compound (usually duplicate ten half-log dilutions starting at 10 µM) in the binding assay. Counts per well were measured and $IC_{50}s$ determined by linear regression.

Representative compounds of the present invention were tested according to the procedures described in Examples 165, 166, 167, 168 and 169 above for binding to the estrogen, androgen and progestin receptors, with results as listed in Table 8.

The results listed in Table 8 below, for Estrogen Receptor α and Estrogen Receptor β are listed as $IC_{50}s$ in µM or % Inhibition at 10 µM; for Androgen Receptor, Rat Cystol results are listed as $IC_{50}s$ in µM or % Inhibition at 1 µM; for Androgen Receptor Rat COS-7 Cells, results are listed as $IC_{50}s$ in µM or % Inhibition at 3 µM; and for Progestin Receptor, results are listed as $IC_{50}s$ in µM or % Inhibition at 10 µM.

TABLE 8

| ID No. | Estrogen α | Estrogen β | Androgen Rat Cystol | Androgen Rat Cos-7 | Progestin |
|---|---|---|---|---|---|
| 3 | 0.18 µM | | | | |
| 8 | 1.6 µM | 0.26 µM | 43% | <4 µM | |
| 9 | 10 µM | 0.85 µM | 20% | 0.8 µM | 3.2 µM |
| 10 | 10 µM | 10 µM | −0.2% | 7.5 µM | 54% |
| 11 | 14% | −1% | 1.5% | | 22% |
| 12 | 22% | 12% | 0.5% | 1.5 µM | 0.27 µM |
| 14 | | | | 1 µM | |
| 15 | 1.8% | 22% | | | 2.4 µM |
| 16 | | | −62% | 6 µM | |
| 17 | 4% | 8.8% | 1.5% | 0.8 µM | 18% |
| 20 | | | −16% | | |
| 22 | | | −33% | | |
| 23 | | | 3% | | |
| 24 | 0.022 µM | 0.068 µM | | | |
| 29 | | | −12% | 10 µM | |
| 30 | 2.2 µM | 10 µM | −17% | | |
| 32 | 10 µM | 5 µM | 23.5% | 4.5 µM | |
| 34 | 0.25 µM | 55% | 0.25 µM | 1.3 µM | 0.099 µM |
| 36 | | | 5.5% | | |
| 37 | 10 µM | 0.44 µM | | | |
| 39 | 0.6 µM | | | | |
| 40 | 2.6 µM | | | | |
| 42 | 5% | 8.5% | −12% | | 9 µM |
| 43 | 1% | 15% | −20% | | 8.4 µM |
| 44 | 3.2% | 20% | −9.0% | 3.7 µM | 1.6 µM |
| 47 | 2.3 µM | 0.76 µM | 56.5% | 3 µM | 1.1 µM |
| 48 | 0.45 µM | 0.013 µM | | 2.1 µM | 0.9 µM |
| 50 | 0.018 µM | 0.051 µM | | | |
| 52 | −2.5% | 2% | 9.75% | | 29% |
| 53 | 0.62 µM | 0.51 µM | 39.5% | 4 µM | 1.2 µM |
| 54 | −10% | 0.51% | −24% | | 10 µM |
| 57 | | | −20% | | 10 µM |
| 61 | 0.4 µM | 10 µM | | | |
| 63 | 4% | 5.5% | −1.6% | | 7.6% |
| 65 | 8.2% | 6.5% | 115% | 0.3 µM | 0.097 µM |
| 68 | 19.9% | 27.8% | 14.6% | 2.2 µM | 5.7 µM |
| 69 | 2.3% | 6.8% | 13.5% | | 2.2 µM |
| 70 | 0.11 µM | 0.065 µM | −11% | 3.4 µM | 3.2 µM |
| 71 | 29.5% | 30.5% | 97.5% | 0.2 µM | 2.4 µM |
| 72 | 27% | 32% | −9.0% | | 2.9 µM |
| 73 | 1.7% | 7.7% | −7.0% | | 50% |
| 74 | 7.8% | 15% | 54.5% | | 53.5% |
| 75 | 10 µM | 1.6 µM | 64.5% | 3.4 µM | 1.5 µM |
| 76 | −0.1% | 16% | 55% | 10 µM | 2.7 µM |
| 77 | 1.2% | 8.1% | −6.5% | | 3.1 µM |
| 78 | 14% | 42% | 10% | | 0.91 µM |
| 79 | 8.25 µM | 1.2 | | | 0.057 µM |
| 80 | 5.7% | 8.7% | 94.5% | 1.56 µM | 0.77 µM |
| 81 | 16% | 11% | 63% | | 1.1 µM |
| 82 | 16% | 18% | 97% | | 0.064 µM |
| 83 | 11% | 22% | | | 0.82 µM |
| 84 | 4% | 1.4% | 4.6% | | 1.7 µM |
| 85 | 14% | 46% | 71% | 0.6 µM | 0.1 µM |
| 86 | 18% | 31% | 13% | | 2.6 µM |
| 87 | 22% | 8% | 8.5% | | 10.5% |
| 88 | 21% | 2% | 4.9% | | 6.8% |
| 89 | 7.5% | 14% | 5.8% | | 0.39 µM |
| 91 | 10% | 4% | 47% | 0.5 µM | 38.5% |
| 93 | 11% | 12% | 78% | 0.3 µM | 40.3% |

TABLE 8-continued

| ID No. | Estrogen α | Estrogen β | Androgen Rat Cystol | Androgen Rat Cos-7 | Progestin |
|---|---|---|---|---|---|
| 94 | 11% | 7% | 19% | | 21.5% |
| 95 | 12% | 10% | | | 18% |
| 100 | 0.97 µM | 0.085 µM | 87% | | 0.9 µM |
| 101 | 0% | 3% | 30% | | 22% |
| 103 | 2.5% | 3.5% | −22% | | 7.65% |
| 105 | 10 µM | 0.63 µM | 88% | | 0.18 µM |
| 106 | 6.2% | 5.4% | 12% | | 1.7 µM |
| 109 | 3.4% | 22% | | 2.2 µM | 5.3 µM |
| 110 | 6.06% | 9.3% | | 0.93 | 4.34 |
| 111 | 4.4% | 7.6% | | | 14% |
| 112 | 5% | 13% | | | 2.1% |
| 118 | 2.8 µM | 0.09 µM | | | 9.1 µM |
| 119 | 0.47 µM | 0.51 µM | | | |
| 121 | 1.2 µM | | | | |
| 124 | 1.2 µM | | | | |
| 125 | 6.9% | 24% | | 5 µM | 4.6 µM |
| 126 | 4.6 µM | 0.91 µM | | | 0.99 µM |
| 133 | 10% | 7.2% | | | 50% |
| 134 | 2.35% | 5.2% | | 3 µM | 3 µM |

EXAMPLE 170

As a specific embodiment of an oral composition, 100 mg of the compound prepared as in Example 163 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim
1. A compound of formula (II)

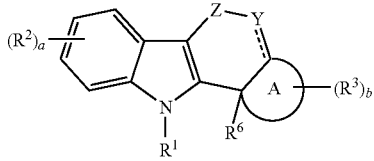

wherein
Y is selected from the group consisting of —N═, —NH— and —N(CH$_3$)—;
and Z is —CH$_2$—;

is phenyl;
a is 1;
b is an integer selected from 0 to 1;
provided that when R$^1$ is hydrogen or methyl; then b is other than 0;
R$^1$ is selected from the group consisting of hydrogen, hydroxy, methyl, and ethyl,
R$^2$ is selected from the group consisting of hydroxy, and methoxy, and
R$^3$ is selected from the group consisting of hydroxy, and methoxy,
or a pharmaceutically acceptable salt thereof.

2. A pharmaceutical composition comprising a pharmaceutically acceptable carrier and a compound of claim 1.

* * * * *